(12) United States Patent
Rosenberg et al.

(10) Patent No.: US 6,486,872 B2
(45) Date of Patent: *Nov. 26, 2002

(54) METHOD AND APPARATUS FOR PROVIDING PASSIVE FLUID FORCE FEEDBACK

(75) Inventors: Louis B. Rosenberg, Pleasanton; Bruce M. Schena, Menlo Park; Richard B. Gillespie, Redwood City, all of CA (US)

(73) Assignee: Immersion Corporation, San Jose, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/028,082

(22) Filed: Feb. 23, 1998

(65) Prior Publication Data

US 2002/0113771 A1 Aug. 22, 2002

Related U.S. Application Data

(63) Continuation of application No. 08/489,068, filed on Jun. 9, 1995, now Pat. No. 5,721,566.

(51) Int. Cl.$^7$ ................................................. G09G 5/08
(52) U.S. Cl. .................. 345/161; 74/471 XY; 200/6 A
(58) Field of Search ................... 345/156, 157, 345/161, 162, 179; 74/471 XY; 200/6 A; 341/21; 318/568.1, 568.16, 568.17

(56) References Cited

U.S. PATENT DOCUMENTS

| | | |
|---|---|---|
| 2,906,179 A | 9/1959 | Bower |
| 3,490,059 A | 1/1970 | Paulsen et al. |
| 3,531,868 A | 10/1970 | Stevenson |

(List continued on next page.)

FOREIGN PATENT DOCUMENTS

| | | |
|---|---|---|
| GB | 2254911 A | 10/1992 |
| JP | 4-34610 | 2/1992 |
| WO | WO95/02233 | 1/1995 |
| WO | WO9502801 | 1/1995 |
| WO | WO95/10080 | 4/1995 |
| WO | WO9520787 | 8/1995 |
| WO | WO95/20788 | 8/1995 |
| WO | WO9520877 | 8/1995 |
| WO | WO 95/32459 | 11/1995 |
| WO | WO9616397 | 5/1996 |
| WO | WO9622591 | 7/1996 |

OTHER PUBLICATIONS

"3D Human Interface Tool," Immersion Probe™, Immersion Human Interface Corporation 1994.
"Call it Palpable Progress," Science & Technology, Business Week, Oct. 9, 1995, pp. 93.
"Cursor Waldo", Designer's Corner, Useful Technology for Your Idea Life, Design News, Mar. 7, 1994, pp. 63.

(List continued on next page.)

Primary Examiner—Dennis-Doon Chow
(74) Attorney, Agent, or Firm—Philip H. Albert; Townsend and Townsend and Crew, LLP

(57) ABSTRACT

A method and apparatus for interfacing the motion of an object with a digital processing system includes a sensor for detecting movement of the object along a degree of freedom. A passive pneumatic or hydraulic damper is coupled to the object to provide a damping resistance to the object along the degree of freedom and resist a movement of the object. The damping resistance is provided by regulating the control of a fluid with a digital computing apparatus, thus providing a low-cost, low-power force-feedback interface that is safe for the user. The damper and sensor provide an electromechanical interface between the object and the electrical system. A gimbal or other interface mechanism can be coupled between the damper and the object. The interface is well suited for simulations or video games in which an object such as a joystick is moved and manipulated by the user.

18 Claims, 18 Drawing Sheets

U.S. PATENT DOCUMENTS

| | | | |
|---|---|---|---|
| 3,795,150 | A | 3/1974 | Eckhardt |
| 3,832,895 | A | 9/1974 | Strandh |
| 3,875,488 | A | 4/1975 | Crocker et al. |
| 3,890,958 | A | 6/1975 | Fister et al. |
| 3,903,614 | A | 9/1975 | Diamond |
| 3,919,691 | A | 11/1975 | Noll |
| 3,944,798 | A | 3/1976 | Eaton |
| 4,148,014 | A | 4/1979 | Burson |
| 4,216,467 | A | 8/1980 | Colston |
| 4,227,319 | A | 10/1980 | Guy et al. |
| 4,391,282 | A | 7/1983 | Ando et al. |
| 4,398,889 | A | 8/1983 | Lam et al. |
| 4,436,188 | A | 3/1984 | Jones |
| 4,448,083 | A | 5/1984 | Hayashi |
| 4,477,043 | A | 10/1984 | Repperger |
| 4,477,973 | A | 10/1984 | Davies |
| 4,489,304 | A | 12/1984 | Hayes |
| 4,550,221 | A | 10/1985 | Mabusth |
| 4,550,617 | A | 11/1985 | Fraignier et al. |
| 4,560,983 | A | 12/1985 | Williams |
| 4,571,834 | A | 2/1986 | Fraser et al. |
| 4,593,470 | A | 6/1986 | Davies |
| 4,601,206 | A | 7/1986 | Watson |
| 4,604,016 | A | 8/1986 | Joyce |
| 4,632,341 | A | 12/1986 | Repperger et al. |
| 4,638,798 | A | 1/1987 | Shelden et al. |
| 4,653,011 | A | 3/1987 | Iwano |
| 4,654,648 | A | 3/1987 | Herrington et al. |
| 4,676,002 | A | 6/1987 | Slocum |
| 4,679,331 | A | 7/1987 | Koontz |
| 4,688,983 | A | 8/1987 | Lindbom |
| 4,689,449 | A | * 8/1987 | Rosen ........................ 200/6 A |
| 4,703,443 | A | 10/1987 | Moriyasu |
| 4,704,909 | A | 11/1987 | Grahn et al. |
| 4,750,487 | A | 6/1988 | Zanetti |
| 4,758,692 | A | 7/1988 | Roeser et al. |
| 4,769,763 | A | 9/1988 | Trieb et al. |
| 4,782,327 | A | 11/1988 | Kley et al. |
| 4,787,051 | A | 11/1988 | Olson |
| 4,791,934 | A | 12/1988 | Brunnett |
| 4,794,388 | A | 12/1988 | Matthews |
| 4,798,919 | A | 1/1989 | Miessler et al. |
| 4,800,721 | A | 1/1989 | Cemenska et al. |
| 4,803,413 | A | 2/1989 | Kendig et al. |
| 4,811,608 | A | 3/1989 | Hilton |
| 4,819,195 | A | 4/1989 | Bell et al. |
| 4,823,634 | A | 4/1989 | Culver |
| 4,839,838 | A | 6/1989 | LaBiche et al. |
| 4,849,692 | A | 7/1989 | Blood |
| 4,861,269 | A | 8/1989 | Meenen, Jr. |
| 4,879,556 | A | 11/1989 | Duimel |
| 4,888,877 | A | 12/1989 | Enderle et al. |
| 4,891,889 | A | 1/1990 | Tomelleri |
| 4,907,970 | A | 3/1990 | Meenen, Jr. |
| 4,907,973 | A | 3/1990 | Hon |
| 4,942,545 | A | 7/1990 | Sapia |
| 4,945,305 | A | 7/1990 | Blood |
| 4,945,501 | A | 7/1990 | Bell et al. |
| 4,949,119 | A | 8/1990 | Moncrief et al. |
| 4,961,038 | A | 10/1990 | MacMinn |
| 4,961,138 | A | 10/1990 | Gorniak |
| 4,961,267 | A | 10/1990 | Herzog |
| 4,962,448 | A | 10/1990 | DeMaio et al. |
| 4,962,591 | A | 10/1990 | Zeller et al. |
| 4,982,504 | A | 1/1991 | Söderberg et al. |
| 4,983,786 | A | 1/1991 | Stevens et al. |
| 4,994,669 | A | 2/1991 | Stern |
| 5,007,085 | A | 4/1991 | Greanias et al. |
| 5,007,300 | A | 4/1991 | Siva |
| 5,040,306 | A | 8/1991 | McMurtry et al. |
| 5,044,956 | A | 9/1991 | Behensky et al. |
| 5,050,608 | A | 9/1991 | Watanabe et al. |
| 5,072,361 | A | 12/1991 | Davis et al. |
| 5,076,517 | A | 12/1991 | Ferranti et al. |
| 5,088,046 | A | 2/1992 | McMurtry |
| 5,088,055 | A | 2/1992 | Oyama |
| 5,095,303 | A | 3/1992 | Clark et al. |
| 5,103,404 | A | 4/1992 | McIntosh |
| 5,107,080 | A | 4/1992 | Rosen |
| 5,116,051 | A | 5/1992 | Moncrief et al. |
| 5,128,671 | A | 7/1992 | Thomas, Jr. |
| 5,131,844 | A | 7/1992 | Marinaccio et al. |
| 5,132,672 | A | 7/1992 | Clark |
| 5,139,261 | A | 8/1992 | Openiano |
| 5,142,506 | A | 8/1992 | Edwards |
| 5,142,931 | A | 9/1992 | Menahem |
| 5,143,505 | A | * 9/1992 | Burdea et al. ............... 244/234 |
| 5,146,566 | A | 9/1992 | Hollis, Jr. et al. |
| 5,148,377 | A | 9/1992 | McDonald |
| 5,178,012 | A | 1/1993 | Culp |
| 5,181,181 | A | 1/1993 | Glynn |
| 5,182,557 | A | 1/1993 | Lang |
| 5,184,306 | A | 2/1993 | Erdman et al. |
| 5,184,319 | A | 2/1993 | Kramer |
| 5,185,561 | A | 2/1993 | Good et al. |
| 5,186,629 | A | 2/1993 | Rohen |
| 5,187,874 | A | 2/1993 | Takahashi et al. |
| 5,189,806 | A | 3/1993 | McMurtry et al. |
| 5,193,963 | A | 3/1993 | McAffee et al. |
| 5,204,824 | A | 4/1993 | Fujimaki |
| 5,209,131 | A | 5/1993 | Baxter |
| 5,216,948 | A | 6/1993 | Mitchell et al. |
| 5,220,260 | A | 6/1993 | Schuler |
| 5,223,776 | A | 6/1993 | Radke et al. |
| 5,228,356 | A | 7/1993 | Chuang |
| 5,230,623 | A | 7/1993 | Guthrie et al. |
| 5,243,266 | A | 9/1993 | Kasagami et al. |
| 5,251,127 | A | 10/1993 | Raab |
| 5,251,156 | A | 10/1993 | Heier et al. |
| 5,259,120 | A | 11/1993 | Chapman et al. |
| 5,259,894 | A | 11/1993 | Sampson |
| 5,262,777 | A | 11/1993 | Low et al. |
| 5,264,768 | A | 11/1993 | Gregory et al. |
| 5,275,565 | A | 1/1994 | Moncrief |
| 5,277,281 | A | 1/1994 | Carlson et al. |
| 5,284,330 | A | 2/1994 | Calrson et al. |
| 5,286,203 | A | 2/1994 | Fuller et al. |
| 5,296,846 | A | 3/1994 | Ledley |
| 5,351,692 | A | 10/1994 | Dow et al. |
| 5,354,162 | A | * 10/1994 | Burdea et al. ................. 414/5 |
| 5,379,663 | A | 1/1995 | Hara |
| 5,384,460 | A | 1/1995 | Tseng |
| 5,389,865 | A | 2/1995 | Jacobus et al. |
| 5,390,296 | A | 2/1995 | Crandall et al. |
| 5,396,266 | A | 3/1995 | Brimhall |
| 5,396,267 | A | 3/1995 | Bouton |
| 5,397,323 | A | 3/1995 | Taylor et al. |
| 5,402,582 | A | 4/1995 | Raab |
| 5,405,152 | A | 4/1995 | Katanics et al. |
| 5,412,880 | A | 5/1995 | Raab |
| 5,414,337 | A | 5/1995 | Schuler |
| 5,417,696 | A | 5/1995 | Kashuba et al. |
| 5,428,748 | A | 6/1995 | Davidson et al. |
| 5,429,140 | A | 7/1995 | Burdea et al. |
| 5,436,542 | A | 7/1995 | Petelin et al. |
| 5,436,640 | A | 7/1995 | Reeves |
| 5,440,183 | A | 8/1995 | Denne |
| 5,445,166 | A | 8/1995 | Taylor |
| 5,451,924 | A | 9/1995 | Massimino et al. |
| 5,459,382 | A | 10/1995 | Jacobus et al. |
| 5,467,763 | A | 11/1995 | McMahon et al. |

| | | |
|---|---|---|
| 5,489,812 A | 2/1996 | Furuhata et al. |
| 5,492,312 A | 2/1996 | Carlson |
| 5,496,174 A | 3/1996 | Garner ........................ 434/114 |
| 5,512,919 A | 4/1996 | Araki |
| 5,513,100 A | 4/1996 | Parker et al. |
| 5,570,111 A | 10/1996 | Barrett et al. |
| 5,576,727 A * | 11/1996 | Rosenberg et al. ......... 345/161 |
| 5,587,937 A | 12/1996 | Massie et al. |
| 5,589,828 A * | 12/1996 | Armstrong .................. 345/161 |
| 5,589,854 A * | 12/1996 | Tsai ........................... 345/156 |
| 5,591,082 A | 1/1997 | Jensen et al. |
| 5,591,924 A | 1/1997 | Hilton |
| 5,623,582 A * | 4/1997 | Rosenberg .................. 345/161 |
| 5,625,576 A * | 4/1997 | Massie et al. .............. 318/628 |
| 5,629,594 A | 5/1997 | Jacobus et al. |
| 5,642,469 A | 6/1997 | Hannaford et al. |
| 5,643,087 A | 7/1997 | Marcus et al. |
| 5,661,446 A | 8/1997 | Anderson et al. |
| 5,666,138 A | 9/1997 | Culver |
| 5,701,140 A | 12/1997 | Rosenberg et al. |
| 5,709,219 A | 1/1998 | Chen et al. |
| 5,721,566 A * | 2/1998 | Rosenberg et al. ......... 345/161 |
| 5,724,068 A | 3/1998 | Sanchez et al. |
| 5,731,804 A | 3/1998 | Rosenberg |
| 5,734,373 A | 3/1998 | Rosenberg et al. |
| 5,739,811 A | 4/1998 | Rosenberg et al. |
| 5,742,278 A | 4/1998 | Chen et al. |
| 5,755,577 A | 5/1998 | Gillio |
| 5,767,839 A | 6/1998 | Rosenberg |
| 5,781,172 A | 7/1998 | Engel et al. |
| 5,790,108 A | 8/1998 | Salcudean et al. |
| 5,805,140 A | 9/1998 | Rosenberg et al. |
| 5,816,105 A | 10/1998 | Adelstein |
| 5,821,920 A | 10/1998 | Rosenberg et al. |
| 5,823,876 A | 10/1998 | Unbehand |
| 5,828,363 A | 10/1998 | Yaniger et al. |
| 5,831,596 A | 11/1998 | Marshall et al. |
| 5,872,438 A | 2/1999 | Roston |
| 5,880,714 A | 3/1999 | Rosenberg et al. |
| 5,889,670 A | 3/1999 | Schuler et al. |
| 5,889,672 A | 3/1999 | Schuler et al. |
| 6,004,134 A | 12/1999 | Marcus et al. |
| 6,154,198 A | 11/2000 | Rosenberg |
| 6,201,533 B1 | 3/2001 | Rosenberg et al. |

OTHER PUBLICATIONS

"Foot–Operated Mouse," IBM Technical Disclosure Bulletin, Apr. 1986, vol. 28, No. 11.

"High Performance Model of the Immersion Probe," Immersion Probe™, Immersion Human Interface Corporation.

"Proceedings of the IFIP Congress 65," International Federation for Information Processing, Information Processing 1965, vol. 3, New York, May 24–29, 1965, pp. 506.

"The Personal Digitizer™," Immersion Human Interface Corporation, 1994.

"Useful Technology for Your Idea File," Design News, Mar. 7, 1994, pp. 63.

Adachi, Yoshitaka, et al., Sensory Evaluation of Virtual Haptic Push–Buttons, Technical Research Center Suzuki Motor Corporation.

Adelstein Bernard D. et al., "A High Performance Two Degree–of–Freedom Kinesthetic Interface," Massachusetts Institute of Technology 1992, pp. 108–112.

Adelstein, Bernard D. et al., "Design and Implementation of a Force Reflecting Manipulandum for Manual Control Research," 1992, pp. 1–24.

Atkinston, William D. et al, "Computing with Feeling," Comput. & Graphics, vol. 2, No. 2–E, pp. 97–103.

Batter, James J. et al., "Grope–1: A Computer Display to the Sense of Feel," pp. TA–4–188–TA–4–192.

Bejczy, Antal K., "The Phantom Robot: Predictive Displays for Teleoperation with Time Delay," IEEE 1990, pp. 546–550.

Burdea, Grigore et al., "A Portable Dextrous Master With Force Feedback," Rutgers–The State University of New Jersey.

Burdea, Grigore et al., "Dextrous Telerobotics with Force Feedback–An Overview," Robotica 1991, vol. 9.

Burdea, Grigore et al., "Distributed Virtual Force Feedback," IEEE, May 2, 1993, pp. 25–44.

Buttolo, Pietro et al., "Pen–Based Force Display for Precision Manipulation in Virtual Environments," IEEE Mar. 1995, pp. 1–8.

Colgate J. Edward et al., "Implementation of Stiff Virtual Walls in Force–Reflecting Interfaces," Sep. 22, 1993.

Colgate, J. Edward et al., "Implementation of Stiff Virtual Walls in Force–Reflecting Interfaces," 1993, pp. 1–9.

Ellis, R.E. et al., "Design and Evalusation of a High–Performance Prototype Planar Haptic Interface," ASME Dec. 3, 1993, DSC–vol. 49, pp. 55–64.

Fischer, Patrick et al., "Specification and Design of Input Devices for Teleoperation," 1990.

Fisher, S.S. et al., "Virtual Environment Display System," ACM 1986 Workshop on Interactive 3D Graphics, Oct. 1986.

Gotow, J.K., et al., "Perception of Mechanical Properties at the Man–Machine Interface," IEEE 1987, pp. 688–689.

Hannaford, Blake et al., "Performance Evaluation of a Six–Axis Generalized Force–Reflecting Teleoperator," IEEE May/Jun. 1991, vol. 21, No. 3, pp. 620–633.

Herndon , J.N. et al., "The State–of–the–Art Model M–2 Maintenance System," Proceedings of the 1984 National Topical Meeting on Robotics and Remote Handling in Hostile Environments, American Nuclear Society, pp. 59–65.

Howe, Robert D., "Task Performance with a Dextrous Teleoperated Hand System," Proceedings of SPIE, Nov. 1992, vol. 1833, pp. 1–9.

Iwata Hiroo et al, Volume Haptization, IEEE 1993, pp. 16–18.

Iwata, Hiroo, "Pen–based Haptic Virtual Environment," Institute of Engineering Mechanics, University of Tsukuba, Japan, pp. 287–292.

Jacobsen, S.C. et al., "High Performance, High Dexterity, Force Reflective Teleoperator II," ANS Topical Meeting on Robotics & Remote Systems, Albuquerque, New Mexico Feb. 24–27, 1991, pp. 1–10.

Jones, L.A. et al., "A Perceptual Analysis of Stiffness," Experimental Brain Research, Springer–Verlag 1990, pp. 151–156.

Kim, Won S. et al., A Teleoperation Training Simulator with Visual and Kinesthetic Force Virtual Reality.

Kim, Won S. et al., "Graphics Displays for Operator Aid in Telemanipulation," IEEE 1991, pp. 1059–1067.

Kotoku, Tetsuo et al., "Environment Modeling for the Interactive Display (EMID) Used in Telerobotic Systems," IEEE Nov. 3–5, 1991, pp. 99–1004.

Kotoku, Tetsuo, A Predictive Display with Force Feedback and its Application to Remote Manipulation System with Transmission Time Delay, Jul. 7–10, 1992, Proceedings of the 1992 IEEE/RSJ International Conference on Intelligent Robots and Systems.

Krueger, Myron W., Artificial Reality 1988, pp. 54–75.

McAffee, Douglas A., "Teleoperator System/Telerobot Demonstrator: Force Reflecting Hand Controller Equipment Manual," JPL Jan. 1988, pp. 3–8, 11, and A–34.

Meyer, Kenneth et al., "A Survey of Position Trackers," Presence, vol. 1, No. 2, Spring 1992, pp. 173–200.

Minsky, Margaret et al., "Feeling and Seeing: Issues in Force Display," ACM 1990, pp. 235–242.

Noll, A. Michael, "Man–Machine Tactile Communication Dissertation," Polytechnic Institute of Brooklyn, Jun. 1971, pp. 1–88.

Ouh–young, Ming et al., "Force Display Performs Better than Visual Display in a Simple 6–Docking Task," IEEE 1989, pp. 1462–1466.

Ouh–young, Ming et al., "Using a Manipulator for Force Display in Molecular Docking," IEEE 1988, pp. 1824–1829.

Ouh–Young, Ming, "Force Display in Molecular Docking," Chapel Hill 1990, pp. 1–85.

Rosenberg, Louis B. et al., "Perceptual Decomposition of Virtual Haptic Surfaces," IEEE, Oct. 1993.

Rosenberg, Louis B., "Perceptual Design of a Virtual Rigid Surface Contact," Center for Design Research Stanford University, Air Force Material Command, Apr. 1993, pp. 1–41.

Rosenberg, Louis B., "The Use of Virtual Fixtures as Perceptual Overlays to Enhance Operator Performance in Remote Environments," Air Force Material Command, Sep. 1992, pp. 1–42.

Rosenberg, Louis B., "The Use of Virtual Fixtures to Enhance Operator Performance in Time Delayed Teleoperation," Crew Systems Directorate Biodynamics and Biocommunications Division Wright–Patterson, Air Force Material Command, Mar. 1993, pp. 1–45.

Rosenberg, Louis B., "Virtual Fixtures as Tools to Enhance Operator Performance in Telepresence Environments," SPIE Telemanipulator Technology, 1993.

Rosenberg, Louis B., "Virtual Haptic Overlays Enhance Performance in Telepresence Tasks," SPIE 1994.

Russo, Massimo Andrea, "The Design and Implementation of a Three Degree–of–Freedom Force Output Joystick," Department of Mechanical Engineering, May 11, 1990, pp. 9–40 & 96 & 97.

Russo, Massimo, The Design and Implementation of a Three Degree–of–Freedom Force Output Joystick, 1990.

Schmult, Brian et al., "Application Areas for a Force–Feedback Joystick," ASME 1993, DSC–vol. 49, pp. 47–54.

Schmult, Brian, et al., Application Areas for a Force–Feedback Joystick, 1993, DSC–vol. 49, Advances in Robotics, Mechatronics, and Haptic Interfaces.

Smith, Geoffrey, "Call It Palpable Progress," Business Week, Oct. 9, 1995. pp. 93, 96.

Snow, E. et al., "Compact Force–Reflecting Hand Controller, "JPL, Apr. 1991, vol. 15, No. 3, Item No. 153, pp. 1–15a.

Su, S. Augustine, et al., The Virtual Panel Architecture: A 3D Gesture Framework, 01/93, IEEE Communications.

Tan, Hong Z et al., "Manual Resolution of Compliance When Work and Force Cues are Minimized," ASME 1993, DSC–vol. 49, pp. 99–104.

Tan, Hong Z. et al., "Human Factors for the Design of Force–Reflecting Haptic Interfaces," Tan, Srinivasan, Eberman & Chang, ASME WAM 1994, pp. 1–11.

Tavkhelidze, D.S. et al., "Kinematic Analysis of Five–Link Spherical Mechanisms" Mechanism and Machine Theory, Pergamon Press, 1974, vol. 9, pp. 181–190.

Wiker, Steven F. et al., "Development of Tactile Mice for Blind Access to Computers: Importance of Stimulation Locus, Object Size, and Vibrotactile Display Resolution," Proceedings of the Human Factors Society 35th Annual Meeting 1991, pp. 708–712.

Yamakita, M. et al., Tele–Virtual Reality of Dynamic Mechanical Model, IEEE Jul. 7–10, 1992, pp. 1103–1110.

Hasser, Christopher John, "Tactile Feedback for a Force–Reflecting Haptic Display" Thesis Submitted to the School of Engineering of the University of Dayton, pp. 1–98, Dec. 1995.

Bostrom, M. et al., "Design of An Interactive Lumbar Puncture Simulator with Tactile Feedback," IEEE 0–7803–1363–1, 1993, pp. 280–286.

Kelley, A. et al., "MagicMouse: Tactile and Kinesthetic Feedback in the Human–Computer Interface using an Electromagnetically Actuated Input/Output Device," Dept. of Elec. Eng., Univ. of Brit. Columbia, 1993, pp. 1–27.

Millman, P. et al., "Design of a Four Degree–of–Freedom Force–Reflecting Manipulandum with a Specified Force/Torque Workspace," IEEE CH2969–4, 1991, pp. 1488–1492.

Brooks, F. et al., "Project GROPE—Haptic Displays for Scientific Visualization," Computer Graphics, vol. 24, No. 4, 1990, pp. 177–185.

* cited by examiner

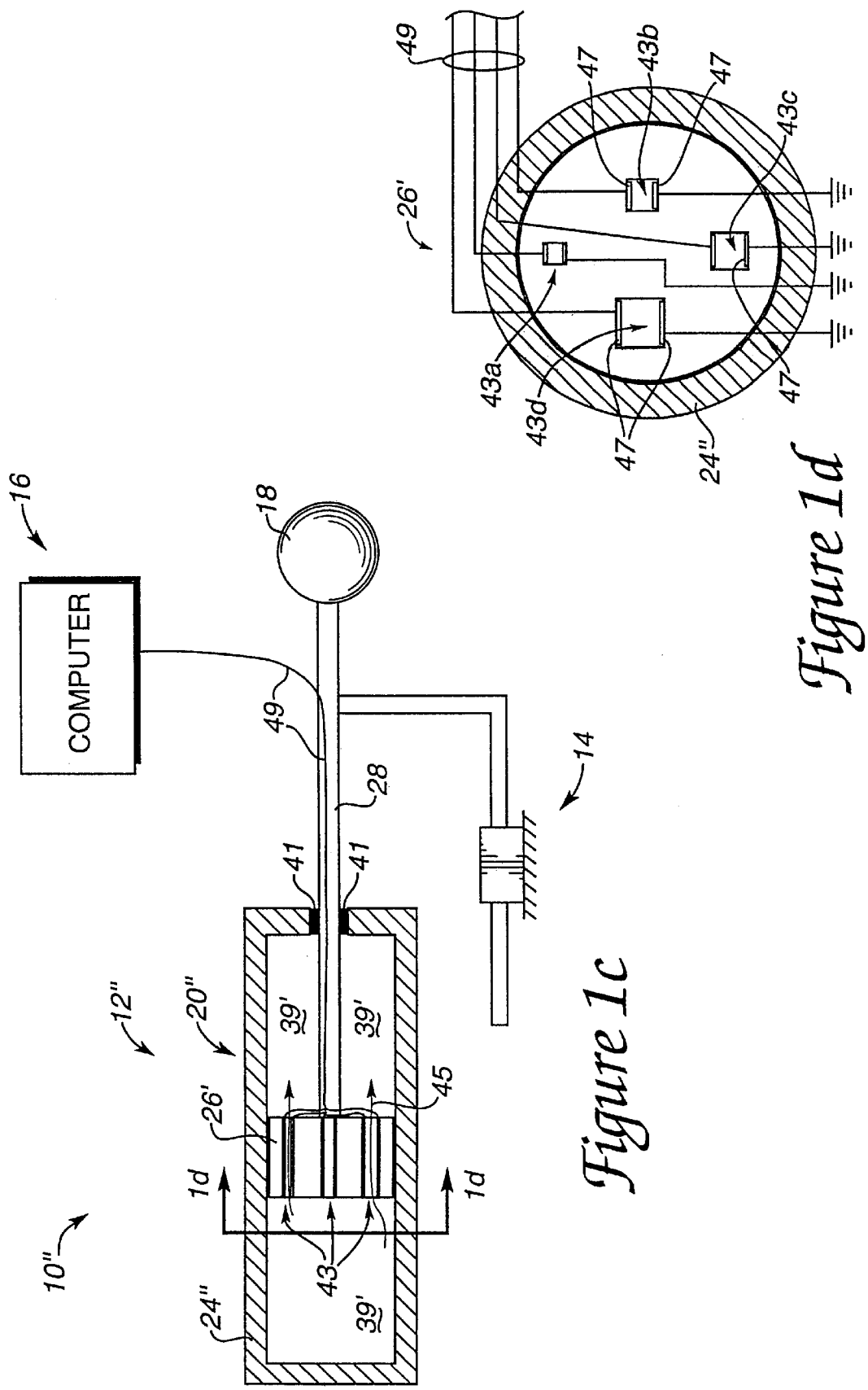

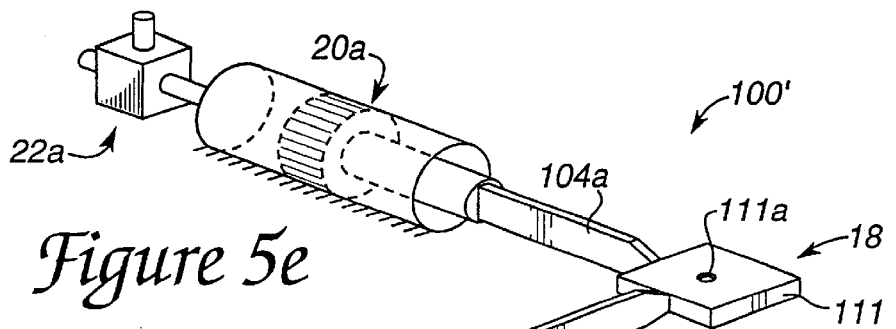
Figure 5e
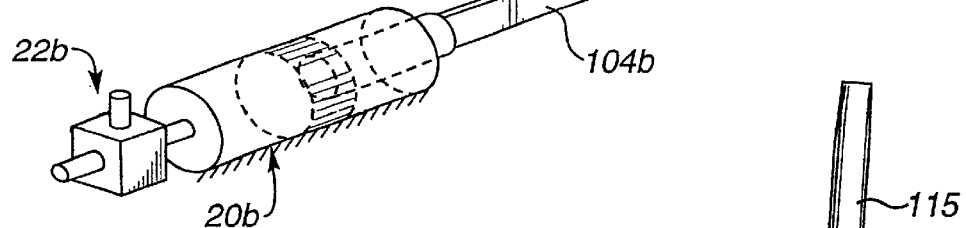
Figure 5f
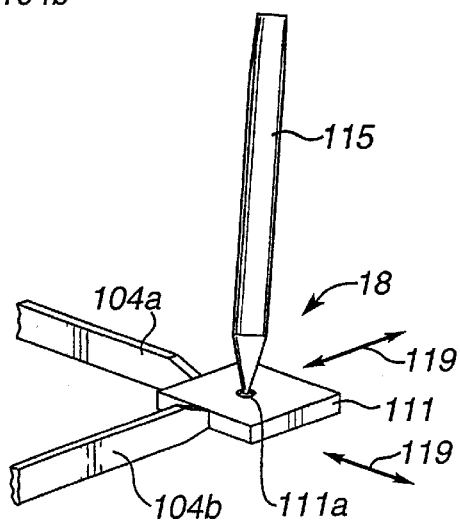
Figure 5g
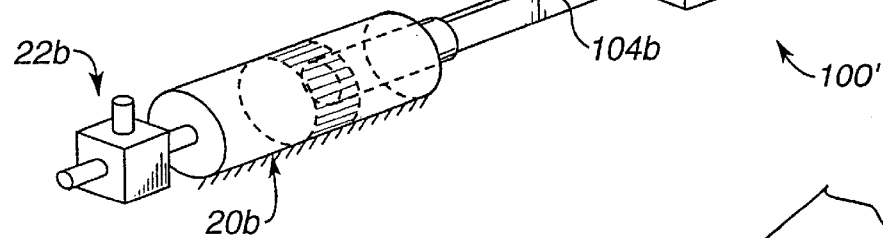
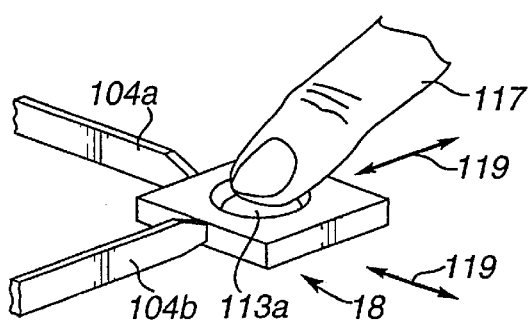
Figure 5h

METHOD AND APPARATUS FOR PROVIDING PASSIVE FLUID FORCE FEEDBACK

"This is a application of copending prior application Ser. No. 08/489,068 filed on Jun. 9, 1995, now No. 5,721,566 the disclosure of which is incorporated herein by reference."

CROSS REFERENCE TO RELATED APPLICATION

This application is a continuation application of copending prior application Ser. No. 08/489,068 filed on Jun. 9, 1995, the disclosure of which is incorporated herein by reference, which is a continuation-in-part of co-pending parent patent application Ser. No. 08/400,233, filed Mar. 3, 1995, on behalf of Louis B. Rosenberg, entitled, "Method and Apparatus of Providing Passive Force Feedback to Human/Computer Interface Systems," assigned to the assignee of the present application.

BACKGROUND OF THE INVENTION

The present invention relates generally to interface devices between humans and computers, and more particularly to computer input devices that provide force feedback to the user.

Computer systems are used extensively in the home entertainment industry to implement video games, video simulations, and the like. In the video game industry, a video game computer system displays a visual game environment to a user on a display screen or other visual output device. Users can interact with the displayed environment to play a game, experience a simulation or "virtual reality" environment, or otherwise influence events depicted on the screen. Such user interaction is implemented through the use of a human-computer interface device, such as a joystick, "joypad" button controller, mouse, stylus and tablet, or the like, that is connected to the computer system controlling the game environment.

One common interface device to game environments is a joystick controller. A joystick usually includes a member for the user to grasp and move in one or more degrees of freedom. The user's manipulations of the joystick are input to the computer system and the results or effects of these manipulations are typically displayed to the user on the display screen. While a standard joystick is effective in allowing a user to input commands to a game environment, it is limited to providing only input to the game computer system. The user can receive feedback about the results of his, or her actions only through the visual medium of the display screen and, usually, the auditory medium. A standard joystick cannot itself provide feedback information to the user. For example, if the simulated aircraft that the user is controlling in a game environment collides with another aircraft, the user only receives the visual and auditory feedback that such a collision occurred. The standard joystick has no means of conveying such collision information to the user.

Joysticks and other input devices have been developed to provide tactile ("haptic") feedback to a user, more generally known as "force feedback." These types of joysticks can provide physical sensations to the user manipulating the joystick. Typically, motors are coupled to the joystick and are connected to the controlling computer system. The computer system can provide forces on the joystick in conjunction with gaming events by controlling the motors. Through such a joystick, the computer system can convey to the user the physical sensation of colliding into a wall, moving through a liquid, driving over a bumpy road, and other sensations. The user can thus experience an entire sensory dimension in the gaming experience that was previously absent. Force feedback joysticks can provide a whole new modality for human-computer interaction.

Force feedback input devices of the prior art have concentrated on providing maximum haptic fidelity, i.e., the realism of the tactile feedback was desired to be optimized. This is because most of the force feedback devices have been targeted at the specific needs of highly industrial applications. To attain such realism, important design concerns such as size, weight, complexity, power consumption, programming compatibility, cost, aesthetics, and safety have been sacrificed. As a result, typical force feedback mechanisms are complex robotic mechanisms which require precision components, high speed interface electronics, and expensive actuators.

To provide realistic force feedback, the devices of the prior art typically use servo motors under computer control. Pneumatic and hydraulic devices are also used as actuators in force feedback devices. In pneumatic and hydraulic devices, a source of pressurized fluid is usually coupled to a piston in a cylinder, and the flow of the pressurized fluid is controlled by a computer system to provide active forces to the user. For example, a pneumatic system is described by Burdea et al. in U.S. Pat. No. 5,143,505, in which active pneumatic actuators are provided on an interface glove to provide force feedback to a user's fingers. These systems regulate pressurized air to generate active forces to the user.

While the potential market and applications of force feedback controllers in the home video game industry is immense, a number of concerns face the potential providers of force feedback joysticks to the general public for video game and similar applications. Foremost among these concerns is the issue of user safety. Because a force feedback device can impart physical forces upon the user, the potential for injury must be carefully addressed. One type of potential injury is an impact injury, which is caused by a driving blow to the user from the joystick handle. Equally as important are repetitive motion injuries, which are debilitative injuries that are caused by moderate jarring of the user's hand over an extended period of game play. Such injury issues must be resolved before force feedback joysticks can be practically sold to the general public.

In the prior art feedback controllers, active forces are directly applied to the user to provide an inherently unsafe controller. In addition, high accelerations are usually produced to provide a wide range of force signal frequencies and achieve the desired high realism. However, such accelerations are even more unsafe for a user operating the device. These joysticks and other devices are thus unfit for the home market of video games and the like.

Other concerns regarding force feedback joysticks include the efficiency of manufacturing and marketing the joysticks. The cost, complexity, reliability, and size of a force feedback joystick for home use should be practical enough to mass produce the devices. In addition, aesthetic concerns such as compactness and operating noise level of a force feedback device are of concern in the home market. Since the prior art feedback controllers are mainly addressed to specific applications in industry, most force feedback mechanisms are costly, large, heavy, have significant power requirements, are difficult to program for applications. The prior art devices require high speed control signals from a controlling computer for stability, which usually requires more expensive and complex electronics. In addition, the prior art force feedback devices are typically large and noisy. These factors provide many obstacles to the would-be manufacturer of force feedback joysticks to the home video game market.

For example, the pneumatic force feedback device of Burdea et al. mentioned above includes many disadvantages to a would-be provider of force feedback devices in the home video game industry. The force feedback interface of Burdea et al. requires a large interface box including bulky pressure regulators, pressurized air supply, and a large 24-volt power supply. The active pneumatic actuators of Burdea et al. require high speed control signals to operate effectively and provide stability. Finally, Burdea et al's pneumatic actuators can potentially be dangerous for a user when strong or unexpected forces are generated on a user of the interface.

Therefore, a safer, less expensive, less complex, more compact, more reliable, easier programmed, more aesthetic alternative to force feedback interface devices is desired for certain applications.

SUMMARY OF THE INVENTION

The present invention provides a human/computer fluid-resistance interface device that provides force feedback to a user operating the device. The device includes computer-controlled pneumatic or hydraulic dampers that provide a modulated passive damping resistance to the motion of an object that is controlled by a user. The interface device of the present invention is inherently safer for a user, requires lower power, and is less costly to produce than active actuators and other types of pneumatic/hydraulic actuators.

More particularly, an apparatus of the present invention for interfacing the motion of an object with an electrical system includes a sensor, such as a digital encoder, that detects movement of an object along a degree of freedom and develops an electrical sensor signal for the electrical system. The sensor is coupled to the object in the preferred embodiment. The apparatus also includes a passive fluid-resistance mechanism, such as a pneumatic or hydraulic damper, coupled to the object to transmit a drag to the object along the degree of freedom and resist a movement of the object. The damper is responsive to an electrical resistance signal provided by the electrical system and, with the sensor, provides an electromechanical interface between the object and the electrical system. In the preferred embodiment, the object is a joystick controller.

In the preferred embodiment, the passive damper uses air (or a different gas) flow to control the damping resistance output by the damper. In alternate embodiments, the passive damper can be a hydraulic brake utilizing liquid flow. The passive damper includes a cylinder and a piston operative to move within the cylinder. A valve is included for regulating a flow of a fluid through the cylinder, the valve being controlled by a digital computing apparatus to transmit a variable drag to the movement of the object. The valve can be an on-off valve which provides only two magnitudes of drag to the object. These two magnitudes include negligible drag when the valve is open, and maximum drag when the valve is closed to allow substantially no movement of the object along the degree of freedom. The valve can alternatively be a variable valve that provides multiple magnitudes of drag to the object. A solenoid can be coupled to the valve to control the opening and closing of the valve from the digital computing apparatus. A gimbal mechanism or slotted yoke mechanism can be coupled between the object and the damper. A play mechanism can also be coupled between the damper and the object for providing a desired amount of play between the damper and the object along the degree of freedom. The play can include rotary backlash provided by a coupling coupled to the object and having a keyed bore which is smaller than a keyed shaft that is received by the keyed bore. The keyed shaft is coupled to the damper. The desired play allows the sensor to detect movement of the object even when maximum resistive force is applied to the object.

Another apparatus for interfacing the motion of an object with an electrical system in accordance with the present invention includes a gimbal mechanism providing a first revolute degree of freedom to an object engaged with the gimbal mechanism about an axis of rotation. The gimbal mechanism includes a closed loop five member linkage in a preferred embodiment. A sensor is rigidly coupled to the gimbal mechanism for sensing positions of the object along the first degree of freedom. A braking mechanism is coupled to the gimbal mechanism to create a passive damping resistance to movement of the object along the first degree of freedom. The braking mechanism provides the damping resistance by regulating the flow of a fluid. The braking mechanism and the sensor provide an electromechanical interface between the object and the electrical system. This electrical system preferably includes a digital processing system for providing a braking signal to the braking mechanism and for receiving an electrical signal from the sensor.

The gimbal mechanism preferably provides a second degree of freedom to the object about a second axis of rotation, and a second sensor senses positions of the object along the second degree of freedom. A second braking mechanism creates a passive damping resistance along the second degree of freedom by regulating the flow of a second fluid. The braking mechanism preferably includes a piston assembly and a valve, where the piston assembly includes a cylinder and a piston operative to move within the cylinder. A piston rod couples the piston to the object and includes two ends, each end connected by a ball joint.

A method for interfacing motion of an object with an electrical system includes providing an object having a degree of freedom. Positions of the object along the degree of freedom are sensed with a sensor and electrical signals are produced from the sensor. A resistance to movement of the object is created along the degree of freedom by controlling the flow of a fluid. The degree of freedom, can be a rotary degree of freedom or a linear degree of freedom. The step of creating a resistance to the object's movement includes coupling a passive brake to the object. The passive brake can include a piston assembly and a valve to control the flow of the fluid. In an alternate embodiment, the brake can include a piston assembly having a cylinder and a piston. An electrorheological fluid is provided in the cylinder, and a voltage is applied to electrodes in the cylinder. The voltage induces an electric field, which, in turn, controls a viscosity of the electrorheological fluid and thereby allows the flow of the fluid to be regulated. A gimbal mechanism or slotted yoke mechanism can also be included to provide two or more degrees of freedom to the object. The gimbal mechanism can be a closed loop five member linkage.

In yet another embodiment of the present invention, a system for controlling an electromechanical interface apparatus manipulated by a user includes a digital computer system for receiving an input control signal and for providing an output control signal which updates a process, such as a simulation or video game process, in response to the input control signal. A passive damper for receiving the output control signal provides a resistive force along a degree of freedom to an object coupled to the passive damper. The object is preferably grasped and moved by the user. The resistive force is based on a flow of a fluid within the passive damper, and the flow of the fluid is based on information in the output control signal. The force resists a user force applied to the object by the user along the degree of freedom. A sensor detects motion of the object and outputs the input control signal including information representative of the position and motion of the object to the digital computer system.

Preferably, the digital computer updates a simulation process in response to the input control signal and displays a simulation (or video game) to the user on a display screen. The passive damper is a pneumatic or hydraulic brake that includes a piston assembly and valve for regulating the flow of the fluid. The digital computer system preferably regulates the fluid flow by controlling the valve. Preferably, a local processor is coupled between the digital computer system and the damper/sensor that receives the output control signal from said digital computer system and provides a second output control signal to the passive damper. The local processor also receives a second input control signal from the sensor and outputs the input control signal to the digital computer system. The local processor can provide the second output control signal to the passive damper in response to the position and motion of the object. This can be accomplished independently of the output control signal from the digital computer system in a "reflex process. A serial interface can output the output control signal from the computer system and can receive the input control signal to the computer system. A digital to analog converter can receive the output control signal, convert the output control signal to an analog control signal, and output the analog control signal to the passive damper. The output control signal can control the resistive force on the object to simulate the object moving into an obstacle, moving over a textured surface, or moving through a damping environment in accordance with the simulation or video game.

The force feedback of the present invention is provided by passive dampers, which do not generate forces on a user but instead provide a damping resistance to the motion of a joystick moved by a user. The present invention is thus inherently safe for a user to operate, In addition, the dampers require less power and slower control signals than active actuators such as active pneumatic or hydraulic actuators and motors. In addition, the dampers are less costly and require simpler computer control electronics than other types of passive actuators. These improvements allow a computer system to have accurate control over a low-cost, safe interface providing realistic force feedback.

These and other advantages of the present invention will become apparent to those skilled in the art upon a reading of the following specification of the invention and a study of the several figures of the drawing.

BRIEF DESCRIPTION OF THE DRAWINGS

FIG. 1c is a schematic diagram of an alternate transducer system of FIG. 1a for use in hydraulic systems;

FIG. 1d is a side sectional view of the piston assembply of FIG. 1c;

FIG. 2 is a schematic diagram of a first alternate embodiment of the transducer system of FIG. 1a;

FIG. 3a is a schematic diagram of a second alternate embodiment of the transducer system of FIG. 1a;

FIG. 4b is a perspective view of the interface system of FIG. 4a;

FIG. 5a is a schematic diagram of an alternate interface system including transducer systems of FIG. 1a;

FIGS. 5b and 5c are schematic diagrams showing the movement of a user object in the interface system of FIG. 5a;

FIG. 5d is a perspective view of the interface system of FIG. 5a;

FIG. 5e is a perspective view of the interface system of FIG. 5a having a stylus-receiving user object;

FIG. 5f is a perspective view of the stylus-receiving user object of FIG. 5e and a stylus;

FIG. 5g is a perspective view of the interface system of FIG. 5a having a finger-receiving user object;

FIG. 5h is a perspective view of the finger-receiving object of FIG. 5g and a user's finger;

FIG. 6c is a sectional side view of the damper shaft and a play mechanism of the transducer system of FIG. 6a;

FIG. 7 is a schematic diagram of an alternate embodiment of the transducer system as shown in FIG. 6a;

FIG. 8 is a schematic diagram of an interface system including the transducer system of FIG. 6a;

FIG. 11 is a perspective view of a slotted yoke mechanical apparatus used with the transducer system of FIG. 6a;

DETAILED DESCRIPTION OF PREFERRED EMBODIMENTS

Figure 1A:
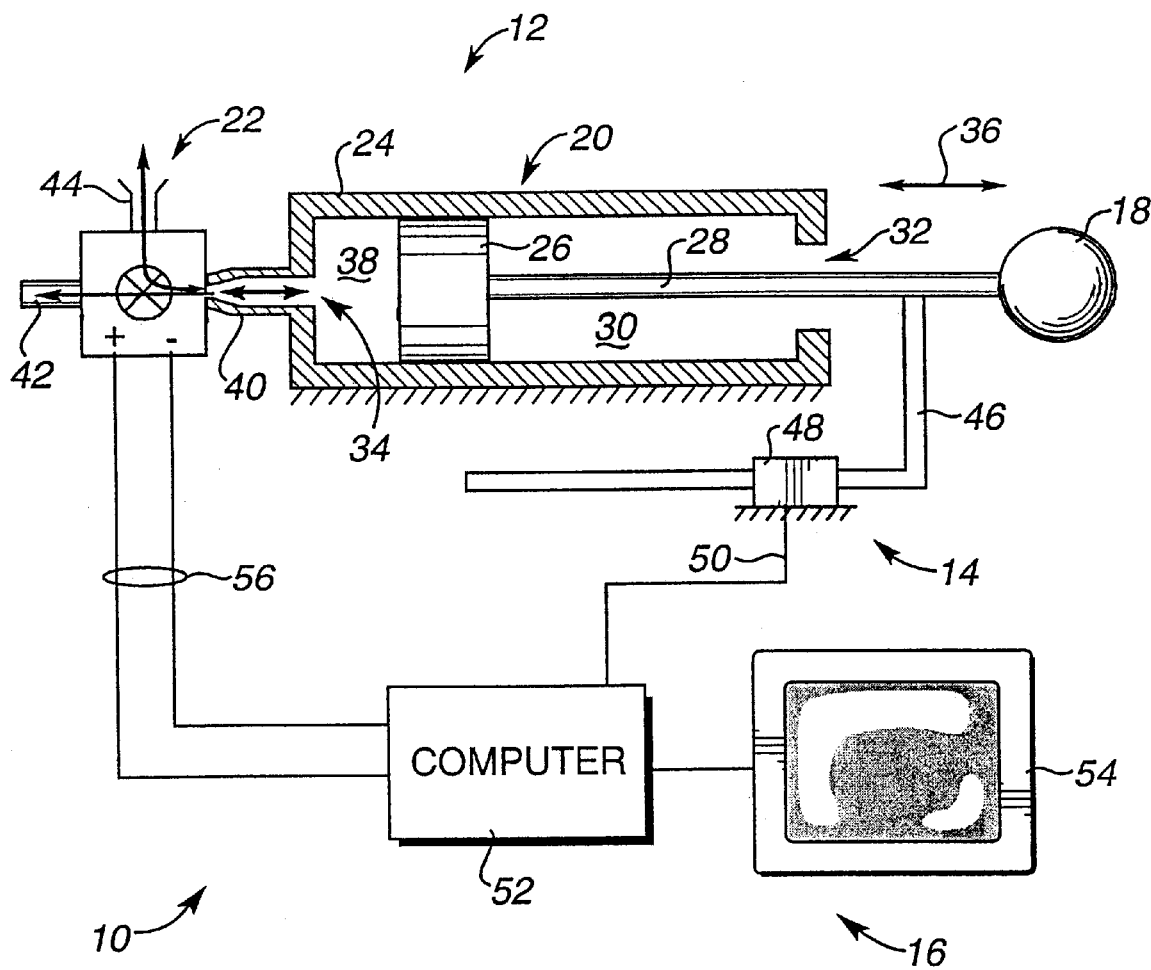
FIG. 1a is a schematic diagram of a transducer system in accordance with the present invention for providing passive force feedback to an object in a linear degree of freedom.

In FIG. 1a, a schematic diagram of a transducer system 10 for providing computer-controlled force feedback in accordance with the present invention is shown. Transducer system 10 includes a damper assembly 12 and a sensor 14. A user object 18 is preferably coupled to damper assembly 12 and sensor 14 to allow the user to interface with a computer system 16. In the preferred embodiments, a user grasps user object 18 and moves the object in one or more provided degrees of freedom. Transducer system 10 is also considered an interface system to computer system 16; in other embodiments, described subsequently, an interface system includes additional mechanical components. The transducer system of the present invention both senses the position of the object and provides passive force feedback in the provided degrees of freedom, as described below. Thus, as used herein, "transducer system" refers to a system that both senses positions and provides force feedback. "Damper" refers to a passive resistance mechanism that provides a damping resistance to motion of an object coupled to the mechanism.

Damper assembly 12 is coupled to object 18 to provide a passive damping resistance to the movement of object 18. Preferably, a user generates a force on object 18, which causes the object to move in one or more provided degrees of freedom. In the embodiment of FIG. 1a, a single linear degree of freedom is provided for object 18. The damping resistance generated by damper assembly 12 dampens or resists the motion of object 18 in that degree of freedom, as described below.

Damper assembly 12 is a "fluid-resistance" device which provides a damping resistance based on the regulation of fluid flow within the device. In the preferred embodiment, the fluid is a gas, such as air. Damper assembly 12 can also be referred to as a "pneumatic brake." In alternate embodiments, hydraulic passive devices can be used to provide resistance based on the regulation of liquid flow. However, pneumatic devices with gas flow, specifically air flow, are more appropriate for the embodiment of FIG. 1a. Damper assembly 12 preferably includes a piston assembly 20 and a valve 22. Piston assembly 20 includes a housing or cylinder 24, a piston 26, and a piston rod 28. Cylinder 24 is an elongated structure having a hollow interior 30, a rod opening 32 positioned at one end, and a valve orifice 34 positioned at the opposite end. The cylinder is preferably cylindrical, but can be rectilinear or have a cross section of other shapes in other embodiments. Preferably, cylinder 24 is made out of glass, graphite, plastic, or a similar smooth material.

Piston 26 is positioned within the interior of cylinder 24 and is constrained to be moved along the degree of freedom designated by axis 36. Piston 26 is preferably also made out of a material such as graphite, glass or plastic and thus has a smooth outer surface. Piston 26 has a cross sectional shape equivalent to cylinder 24 so that a minimum gap between its outer edge and the inner edge of the interior 30 exists and no substantial amount of fluid may escape between the gap. Implementing a moving piston within a cylinder is well known to those skilled in the art. Piston assemblies or similar dapshot devices available from several manufacturers can be used in the present invention. For example, a suitable pneumatic device is the Precision Air Dapshot available from Airpot of Norwalk, Conn. Piston rod 28 couples piston 26 to user object 18 such that when object 18 is moved by a user in the degree of freedom 36, piston 26 is also moved in that degree of freedom.

The motion of piston 26 is dependent on the flow of a fluid 38 through valve orifice 34 in cylinder 24. As stated above, fluid 38 is preferably a gas such as air, but can be a liquid in other embodiments. As is well known to those skilled in the art, a piston may move when valve orifice 34 is unrestricted, which allows the fluid to flow through the orifice. For example, if the fluid is air in a pneumatic system, then the piston 26 can move toward orifice 34 if the piston is allowed to force air from the portion of interior 30 in "front" of the piston, through orifice 34, and to the atmosphere outside cylinder 24. Similarly, piston 26 can move toward opening 32 if air is allowed to flow from the atmosphere into the "front" portion of interior 30 of the cylinder. As referenced herein, the term "free movement" or "freely move" refers to the piston's movement when valve orifice 34 is completely open, allowing unrestricted fluid flow to and from interior 30 through orifice 34. The term "cannot move" or "substantially no movement" refers to the piston's movement when no fluid (actually a negligible amount of fluid) can flow to and from interior 30. In actuality, some movement of piston 26 is typically possible due to the compressible nature of air and other fluids, and due to small fluid leakages in the system.

Fluid 38 is used in damper assembly to provide a damping resistance or drag to the motion of object 18. That is, energy can be removed from the system such that when the user moves object 18, a passive resistance to the object's motion is created. The motion of the object can be resisted by controlling the amount of fluid flow through orifice 34. In the described embodiment, the fluid flow through orifice 34 is controlled by valve 22. Valve 22 is coupled to a duct 40 of cylinder 24 which allows fluid 38 to flow from interior 30, through orifice 34, and into a passage in valve 22. As is well known to those skilled in the art, a valve can be controlled to vary the size of the valve's passage to provide a selectable amount of fluid flow through the valve. The valve shown in FIG. 1a, for example, can be an "on-off valve" or "open-close valve" that provides two amounts of fluid flow through orifice 34. The first is no fluid flow (closed valve), in which the valve is selected to connect a closed port 42 to duct 40. This allows substantially no fluid to enter or leave the interior 30 and stops the movement of piston 26 within cylinder 24 (as explained above, some movement is actually still allowed due to compressibility and leakage of fluids). This provides the maximum damping resistance (i.e., maximum amount of drag) to piston 26 and user object 18.

The second amount of fluid flow is full flow (open valve), in which valve 22 connects open port 44 to duct 40. Open port 44 allows fluid 38 to be vented to the atmosphere or otherwise flow freely. This provides the minimum damping resistance (i.e., minimum amount of drag or "free" movement) to piston 26 and user object 18 in the described embodiment. For example, if a gas such as air is being used as a fluid, then open port 44 can vent the gas to the atmosphere; damper assembly 12 would thus be an "open-loop" system. A suitable on-off valve suitable for use in the present invention is the Minimatic Valve available from Clippard of Cincinnati, Ohio.

The fluid flow through orifice 34 can thus be controlled by adjusting the size of orifice 34 or the size of a passage connected to orifice 34. In the current embodiment, this is accomplished by controlling a valve to select one of multiple provided ports, where each port has an orifice of a different size. As described below, multiple valves can be used to provide a greater variety of different fluid flows through orifice 34.

In an alternate embodiment, a servo valve can be used to provide a desired fluid flow. Such a valve receives an analog voltage signal for incrementally controlling the size of the valve's passageway based on the analog voltage, thus allowing fluid flow to be controlled to a finer resolution than when using on-off valves. A suitable servo valve for use in the present invention is QBI available from Proportion Air of McCordsville, Ind.

Passive dampers, such as damper assembly 12, can provide realistic force feedback to a user operating an interface apparatus in a simulated environment. Passive dampers impose a resistance to the motion of an object 18 manipulated by the user. Thus, a user who manipulates an interface having passive dampers will feel forces only when he or she actually moves an object of the interface.

Passive dampers/actuators 12 provide several advantages when compared to active actuators. Passive dampers are much less expensive and complex than active actuators. For example, a substantially lower current is required to drive passive dampers than active actuators. This allows a less expensive power supply to drive a passive damper system, and also allows a force feedback mechanism to be smaller and more lightweight due to the smaller power supply. Also, in the active pneumatic and hydraulic devices of the prior art, a supply of pressurized air must be regulated to provide active forces, requiring more complex and expensive components and controllers.

In addition, passive dampers require substantially slower control signals to operate effectively in a simulation environment than do active dampers such as motors. This is significant if the controller of an interface mechanism is a computer system that includes only a standard, low-speed input/output port, such as a serial port. Serial ports are quite common to personal computers but do not communicate quickly enough to perform real-time, stable control of most active actuators. When an interface controller with slower control signals is used, passive dampers can provide stable force feedback to the user. Another advantage of passive dampers is that they do not generate forces on the interface and the user and are thus more safe for the user. A user will not experience unexpected and possibly injurious forces from the interface object 18, since the user is inputting all the energy into the system and providing all the active forces.

The fluid dampers of the present invention (i.e., pneumatic and/or hydraulic) provide even greater advantages to a low-cost, safe force feedback interface than do other types of passive actuators or dampers. Since the resistance applied to the user object 18 is provided by the flow of a fluid, only valves or other devices for controlling the size of orifices are needed to change the resistance felt by the user. This allows simple solenoids and other low-power components to be used to control the valves, instead of more complex components used in other passive and active actuators. In a damping system, signals are output by a controlling computer to control a valve or change the size of an orifice only when a change in resistive force occurs, allowing real-time stable control of force feedback even for very slow electronics systems and input/output ports. In addition, the piston assemblies are very low cost and safer compared to other passive actuator devices.

Sensor 14 is coupled to object 18 in the described embodiment and senses the position of the object in a degree of freedom. The object 18 in the embodiment of FIG. 1a is provided with only a single linear degree of freedom such that sensor 14 senses the position of the object in that single degree of freedom. A sliding member 46 is coupled to piston rod 28 or to object 18 and moves through sensor 14, which in the embodiment of FIG. 1a can be a linear pot, linear digital encoder, LVDT, or similar device for sensing an object's position in a linear degree of freedom. For example, part number 0243-0000 available from Transtek of Ellington, Conn. can be used. In alternate embodiments, sensor 14 can be used to detect rotary motion of object 18, as described in greater detail below with reference to FIG. 4a. Sensor 14 is coupled to computer system 16 by a bus 50, which carries electrical signals that are representative of the position of object 18 along the provided degree of freedom from sensor 14 to computer system 16.

Valve 22 is preferably controlled by a digital processing system or other electrical system. Preferably, the digital processing system is a computer system 16, which can include a computer apparatus 52 and a display screen 54. Numerous other peripherals and interface devices can be coupled to computer system 16 as well. Computer system 16 is coupled to valve 22 by bus 56 and provides electrical signals to the valve to control the valve. For example, when using the on-off valve described above, a solenoid can be coupled to the valve to cause the valve to open or close when specific electrical signals are applied to the solenoid, as is well known to those skilled the art. Computer apparatus 52 can include an interface to provide the signals to a solenoid; examples of such an interface circuit are described below with reference to FIGS. 12 and 13. Alternately, computer apparatus 52 can provide an analog voltage signal to control a servo valve, as described above and with reference to FIG. 13.

Display 54 can be used to display a virtual reality environment for the user to view. Display 54 can be a standard display screen or CRT, 3-D goggles, or any other visual interface. For example, the user object 18 can control a computer-generated object displayed on a two-dimensional screen, such as a picture of a instrument, a joystick, a cursor, etc. The user can interact with the simulation by viewing the screen. The computer system 16 receives input from sensor 14 to influence the position and movement of computer-generated objects that are controlled by object 18, and the computer system 16 outputs signals to damper assembly 12 when computer-generated objects interact or a haptic effect is to be transmitted to the user. For example, if a user-controlled object displayed on display 54 collides with a "wall" in the simulation, that collision can be viewed on the screen and appropriate force feedback can be applied to user object 18 as well.

User object 18 is preferably grasped or otherwise controlled by a user. By "grasp", it is meant that users may releasably engage a grip portion of the object in some fashion, such as by hand, with their fingertips, or even orally in the case of handicapped persons. In the described embodiment, object 18 is a handle, such as a control handle on a joystick for manipulating the A movement of computer-controlled objects or a steering wheel, palm grip, etc. Computer apparatus 52 can display objects on display screen 54 and the user can interface with the objects by moving the handle to affect the view displayed, the position of a displayed object, the view of an object, etc. Other types of objects are also suitable for the present invention, such as a pool cue, a stylus, a joystick, a steering wheel, a knob, a grip, a medical instrument (laparoscope, catheter, etc.), and so on.

Additional mechanical apparatuses can be coupled between transducer system 10 and user object 18 to provide additional stability to the motion of object 18. Also, mechanical apparatuses can add additional degrees of freedom to object 18. In such an embodiment, each provided degree of freedom preferably includes its own transducer system 10.

Figure 1B:
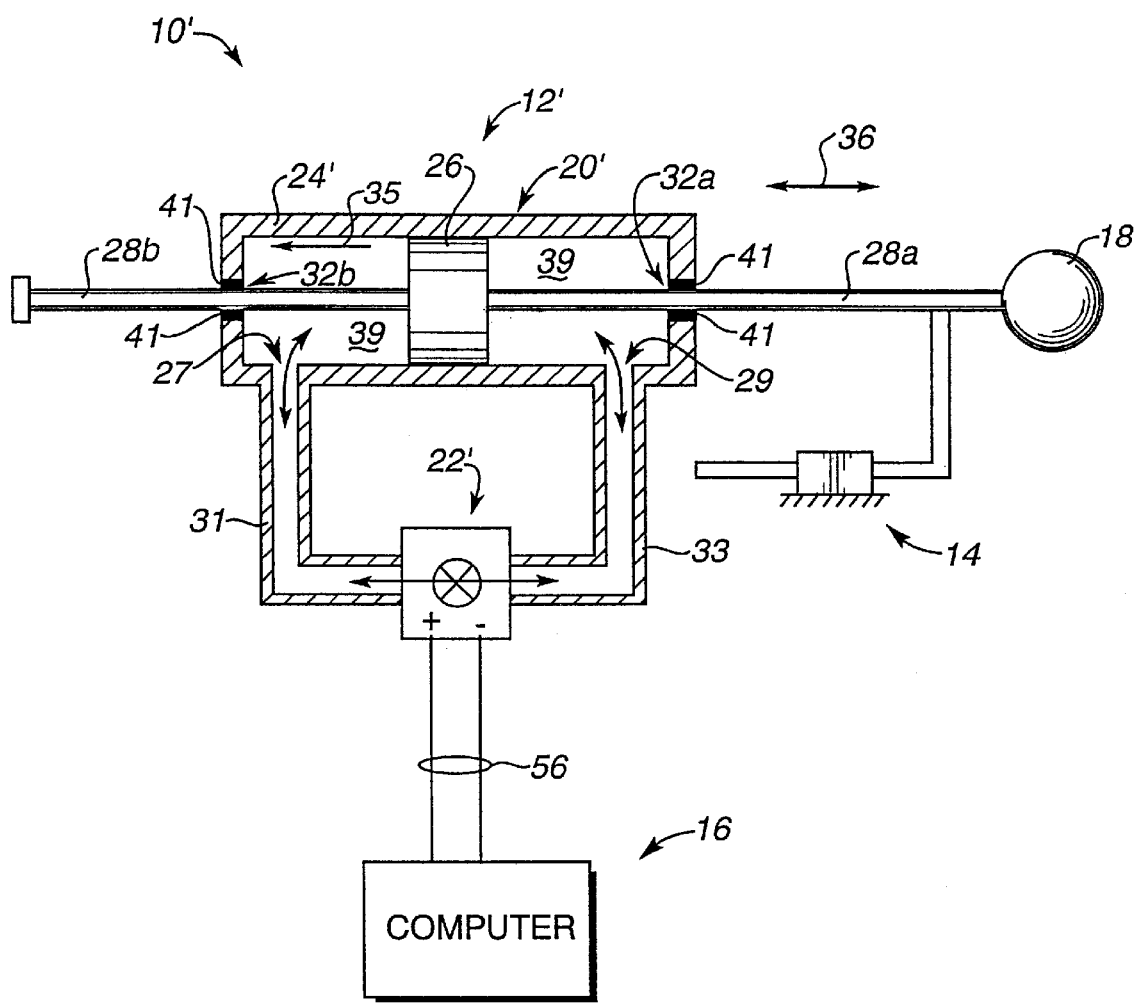
FIG. 1b is a schematic diagram of an alternate transducer system of FIG. 1a for use in hydraulic systems.

FIG. 1b is a schematic illustration of an alternate embodiment 10' of the transducer system shown in FIG. 1a. System 10' is more applicable for fluids such as liquids and gases other than air. System 10' includes a damper assembly 12', sensor 14, and user object 18 for interfacing with computer system 16. Sensor 14, computer system 16, and user object 18 are substantially similar to the corresponding components of system 10 as described with reference to FIG. 1a.

Damper assembly 12' includes a piston assembly 20' and a valve 22'. Piston assembly 20' includes cylinder 24', piston 26, piston rod 28a, piston rod 28b, orifice 27, and orifice 29. The piston 26 and piston rod 28a operate substantially the same as described with reference to FIG. 1a. Piston rod 28b is additionally coupled to the opposite side of piston 26 from rod 28a and extends through an aperture 32b in cylinder 24'. Rod 29b is provided to balance the volume of fluid 39 on both sides of piston 26 within cylinder 24' and thus allow an equal damping resistance to be provided to object 18 in both directions along axis 36. Since system 10' typically is used for closed systems in which a fluid is not desired to escape from cylinder 24', seals 41 are preferably provided between apertures 32a and 32b and the piston rods 28a and 28b, respectively, to prevent any fluid leakages through apertures 32a and 32b.

Cylinder 24' includes two orifices 27 and 29 instead of the single orifice 34 of FIG. 1a. Orifice 27 leads to duct 31, which extends from cylinder 24' to valve 22'. Duct 31 is preferably coupled to a first port of valve 22'. Similarly, orifice 29 leads to duct 33, which extends from cylinder 24' to the second port of valve 22'. Orifices 27 and 29 are arranged such that one of the orifices is near one end of cylinder 24', and the other orifice is positioned near the opposite end of the cylinder. The space between the cylinders is the allowed movement range for piston 26 along the linear degree of freedom indicated by axis 36, as explained below.

Damper assembly 12' functions as a closed loop system, i.e., a fluid is allowed to flow in a closed loop. When piston 26 is moved by the user in a direction indicated by arrow 35, fluid 39 can flow from the interior of cylinder 24' at the "front" of the cylinder, through orifice 27, through valve 22' (when the valve is open), and into the interior at the "back" of the cylinder through orifice 29. Likewise, when piston 26 is moved in a direction opposite to that of arrow 35, fluid 39 moves from the interior of cylinder 24', through orifice 29, through valve 22', through orifice 27, and back into the cylinder 24'. The piston is thus "double acting" in that fluid on both sides of the piston is caused to flow when the piston is moved.

Valve 22' is can be controlled by computer system 16 to alter the amount of fluid flowing to adjust the size of an orifice in valve 22' by preferably controlling a solenoid or other electromechanical device. In one embodiment, valve 22' is an on-off valve having two states: full fluid flow (open) and substantially no fluid flow (closed). In the open valve state, fluid is allowed to freely flow from duct 31 to duct 33 or vice-versa. In the closed valve state, the passage between the ducts is blocked, allowing no fluid flow. Thus, piston 26 and handle 18 can be moved in the provided degree of freedom if the computer system controls valve 22' to open, and the piston/handle are provided with maximum damping resistance when valve 22' is closed.

As described with reference to FIG. 1a, valve 22' can also be implemented as a servo valve that can more finely control the size of its orifice. An analog voltage signal (or sampled digital signal) can be applied by computer system 16 for incrementally controlling the cross-sectional size of the valve's passageway/orifice based on the voltage, thus allowing fluid flow to be controlled to a finer resolution than when using on-off valves.

The closed-loop embodiment of FIG. 1b is especially suitable for hydraulic dampers in which fluid 39 is a liquid (including an electrorheological liquid, as described below in FIG. 1c), as well as dampers in which fluid 39 is a gas other than air. In such damper systems, the fluid 39 is normally provided in a closed system so that the fluid does not continually have to be replaced with new fluid from a fluid source.

FIG. 1c is a schematic illustration of an alternate embodiment 10" of the transducer system shown in FIG. 1b. System 10" includes a damper assembly 12", sensor 14, and user object 18 for interfacing with computer system 16. Sensor 14, computer system 16, and user object 18 are substantially similar to the corresponding components of system 10 as described with reference to FIGS. 1a and 1b.

Damper assembly 12" includes a piston assembly 20". Piston assembly 20" includes cylinder 24", piston 26', and piston rod 28. Cylinder 24" is provided with one aperture 32, which is closed to fluid leakage by seals 41. No valve is included in damper assembly 12", for his reasons described below. Piston 26' is preferably provided with at least one aperture 43. A fluid 39' flows through the aperture(s) 43 when piston 26' is moved along axis 36, as indicated by arrows 45. Apertures 43 can have a rectangular, circular, or other cross-sectional shape. Each aperture preferably includes electrodes 47, as described below with reference to FIG. 1d. Wires 49 coupled to the electrodes can be routed from piston 26', along (or inside) piston rod 28, and out to computer system 16.

Damper assembly 12" is a closed system, and is therefore appropriate for non-air fluids such as liquids. Preferably, the transducer system 10" of FIG. 1c can control the damping resistance provided to the motion of user object 18 without changing the size of apertures 43. Instead, the flow of the fluid can be controlled by changing the properties of the fluid itself. More specifically, fluid 39' provided within cylinder 24" is preferably an "electrorheological fluid", which is a fluid that has a viscosity that can be changed electronically. If an electric field is applied to an electrorheological fluid, the viscosity of the fluid can be changed. By changing the viscosity of fluid 39', the fluid will flow at a different rate through apertures 43 when the piston 26' is moved by the user, thus allowing the damping resistance to user object 18 to be controlled. Electrorheological fluids are well known to those skilled in the art. For example, these fluids are described by W. Winslow in U.S. Pat. No. 2,417,850 and U.S. Pat. No. 3,047,507.

FIG. 1d is a side view along line 1d—1d of FIG. 1c and shows an example of using apertures and electric fields to control the viscosity of an electrorheological fluid. Piston 26' can include a single aperture or multiple apertures 43a, 43b, 43c, and 43d. Electrodes 47 are positioned within each aperture 43a–d. Computer system 16 can be coupled to electrodes 47 by buses 49 and send an analog or digital voltage to the electrodes to apply an electric field to the apertures 43a–d. The electric field, in turn, raises the viscosity of fluid 39' flowing through the apertures 43. This will increase the damping resistance applied to user object 18 in an on-off type of resistance, similar to on-off valves described above. In addition, the computer system can vary the voltage applied to electrodes 47 to vary the viscosity of the fluid through an aperture 43 to a desired degree, similar to the servo valve described above.

The multiple apertures 43a–d can be provided in piston 26' to dampen the motion of object 18 in discrete magnitudes. For example, an electric field can be applied to small aperture 43a to cause only the fluid flowing through aperture 43a to raise its viscosity. An electric field can also be applied to large aperture 43d to raise the viscosity of the fluid only flowing through aperture 43d. Since aperture 43d is larger than aperture 43a, more fluid can flow with the same electric field applied, so that the user will feel a lesser damping resistance when the electric field is applied to aperture 43d. Various apertures 43a–d and various voltage levels can be used to greatly vary the damping resistance to object 18.

It should be noted that no external ducts or other orifices are required for the system 10" of FIG. 1c. However, electrorheological fluids can also be used in the embodiment of FIG. 1b with ducts 31 and 33. Electrodes can be used within valve 22' or in place of valve 22' to control the viscosity of the fluid and thus control fluid flow.

In an alternative embodiment, the apertures 43a–d in piston 26' can be altered in size, for example, by using valves similar to valve assembly 22 as described above or other electromechanical devices.

Figure 2:
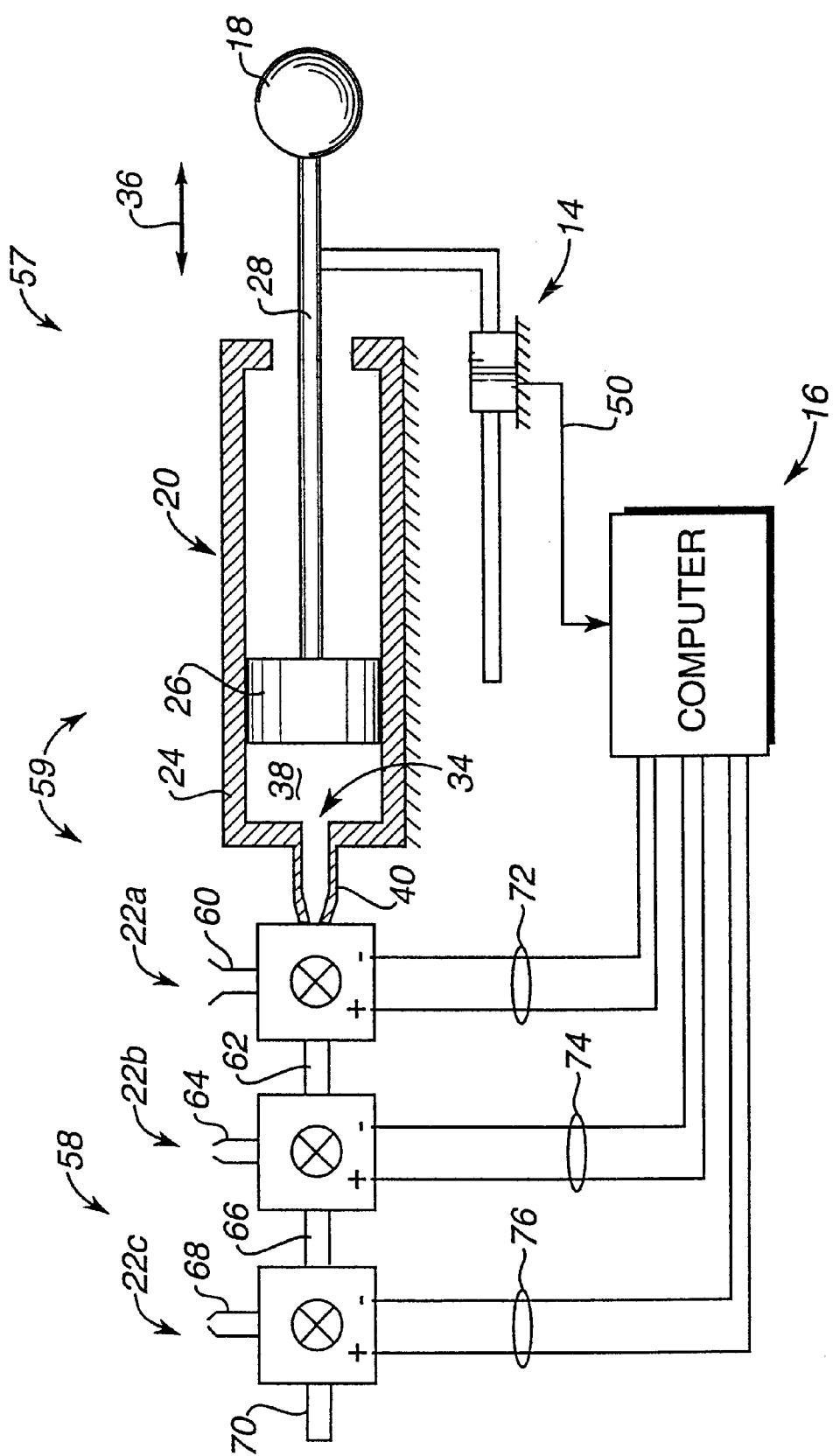

FIG. 2 is an illustration of a transducer system 57 similar to the system 10 shown in FIG. 1a. System 57 includes a damper assembly 59, sensor 14, and user object 18, similar to system 10, for interfacing with computer system 16. Sensor 14, computer system 16, and user object 18 are substantially similar to the corresponding components of system 10 as described with reference to FIG. 1a.

Damper assembly 59 includes a piston assembly 20 and a valve assembly 58. Piston assembly 20 is substantially similar to the piston assembly described with reference to FIG. 1a and includes cylinder 24, piston 26, piston rod 28, and orifice 34 in cylinder 24. Object 19 is coupled to piston 26 by piston rod 28 to provide a single linear degree of freedom to the object. This degree of freedom is indicated by axis 36. Fluid 38 flows through orifice 34 and duct 40 of cylinder 34 when piston 26 moves in the degree of freedom.

Valve assembly 58 includes valves 22a, 22b, and 22c. These valves aide coupled in a series arrangement such that all three of the valves can be controlled to channel fluid 38 through a desired port. In the described example, each valve 22a, 22b, and 22c is an on-off valve that guides fluid 38 to one of two ports. Valve 22a is coupled to duct 40 and either guides fluid 38 to open port 60 or to coupling port 62. Open port 60 provides an orifice of maximum size so that if the fluid is guided through port 60, piston, 26 moves freely with the least damping resistance. If open port 60 is not selected, then coupling port 62 is selected, and fluid 38 is channeled to valve 22b.

Valve 22b is coupled to port 62 and guides fluid 38 either through restricted port 64 or to coupling port 66. Valve 22b is only operative to adjust fluid flow if coupling port 62 of valve 22a is selected. Restricted port 64. of valve 22b has a smaller, partially-closed orifice than the orifice of port 60 so that the flow of fluid 38 through the port is more restricted that the flow through open port 60. This provides a greater degree of damping resistance to the movement of piston 26 and thus user object 18. If restricted port 64 is not selected, then coupling port 66 is selected, and fluid 38 is channeled to valve 22c.

Valve 22c is coupled to port 66 and guides fluid 38 either through restricted port 68 or allows no fluid flow with closed port 70. Valve 22c is operative to adjust fluid flow only if coupling port 62 of valve 22a is selected and coupling port 66 of valve 22b is selected. Restricted port 68 has a partially-closed orifice that has a smaller opening than restricted port 64 of valve 22b. The flow of fluid 38 through port 68 is thus restricted to a greater degree than the flow through port 64, so that port 68 causes a greater degree of damping resistance than port 64 to the movement of piston 26 and user object 18. If closed port 70 is instead selected with valve 22c, then the flow of fluid 38 is completely halted, providing the maximum damping resistance to the movement of piston 26 and object 18. Ideally, piston 26 would not be able to move if closed port 70 were selected; however, due to fluid leakages and fluid compression in the components of the system, piston 26 may have a small (negligible) amount of movement when closed port 70 is selected.

Computer system 16 is coupled to valves 22a, 22b, and 22c by buses 72, 74, and 76, respectively. As described above with reference to FIG. 1a, computer system 16 can provide electrical signals to valves 22a, 22b, and 22c to control the selected ports of the valves. Preferably, a solenoid for each valve is controlled by computer system 16 to switch between the two ports of each valve. In other embodiments, additional valves can be coupled in series to the closed port 70 of valve 22c, for example, to provide additional ports with different orifice sizes. Fluid flow and thus the damping resistance to piston 26 can thus be controlled with greater resolution. In still other embodiments, a servo valve (as described above) can be used for one or more of valves 22a, 22b, and 22c to provide a variably-sized port orifice and thus a higher resolution in adjusting the flow of fluid 38.

Figure 3A:
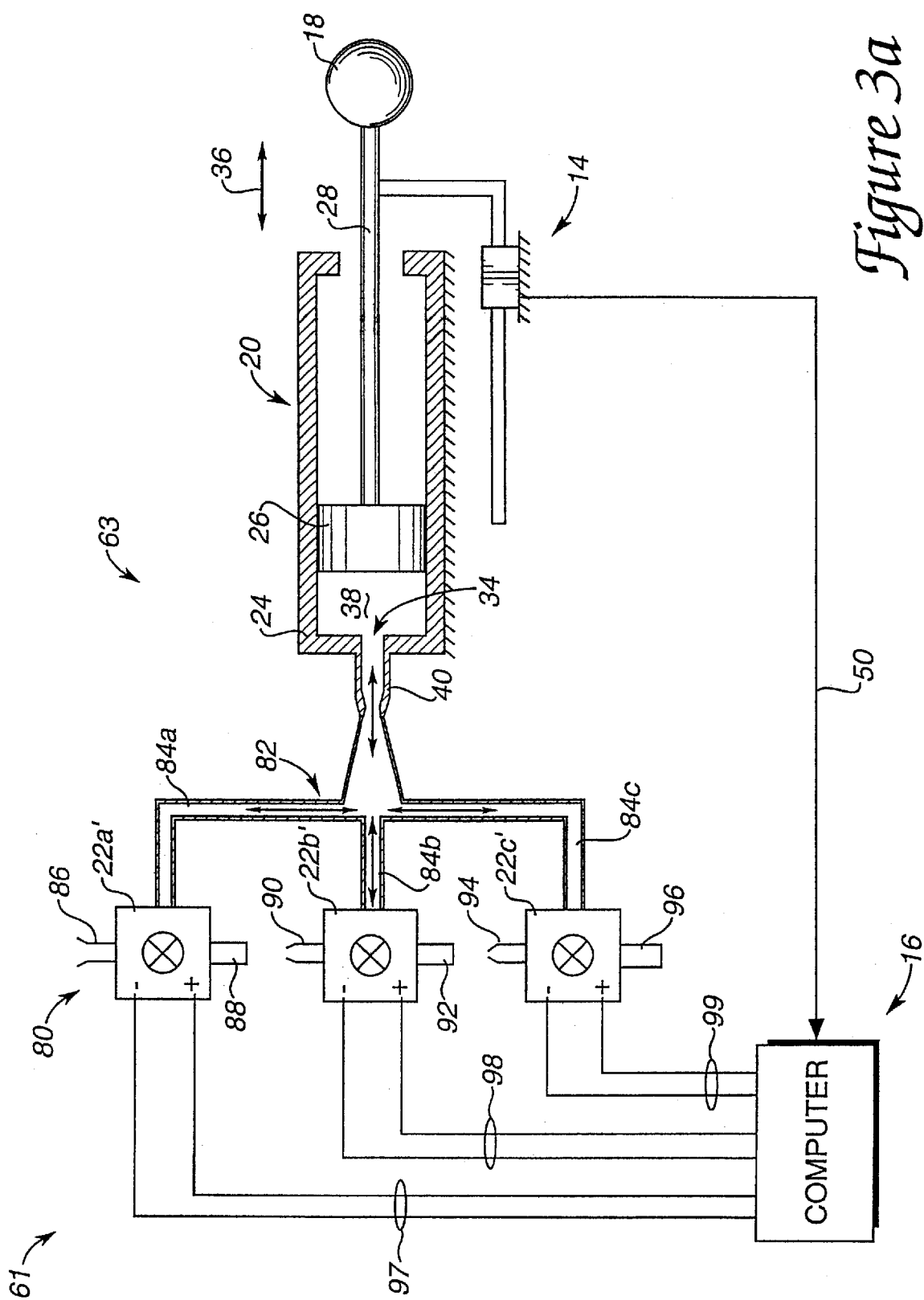

FIG. 3a is an illustration of a transducer system 61 similar to the systems 10 and 57 shown in FIGS. 1a and 2, respectively. System 61 includes a damper assembly 63, sensor 14, and user object 18 interfaced with computer system 16, similar to system 10. Sensor 14, computer system 16, and user object 18 are substantially similar to the corresponding components of system as described with reference to FIG. 1a.

Damper assembly 63 includes a piston assembly 20 and a valve assembly 80. Piston assembly 20 is substantially similar to the piston assembly described with reference to FIGS. 1a and 2 and includes cylinder 24, piston 26, piston rod 28, and orifice 34 in cylinder 24. Object 18 is coupled to piston 26 by piston rod 28 to provide a single linear degree of freedom to the object, as indicated by axis 36. Fluid 38 flows through orifice 34 and duct 40 of cylinder 34 when piston 26 moves in the degree of freedom.

Valve assembly 80 includes valves 22a', 22b', and 22c'. These valves are coupled in a parallel arrangement such that all three of the valves can be controlled to guide fluid 38 to a desired port. This is in contrast to the series arrangement of valves shown in FIG. 2.

In the described example, fluid 38 flows through duct 40 and through a junction 82. Junction 82 is a three-way junction in the described embodiment; generically, junction 82 can be an n-way junction, where n is the number of valves being used in valve assembly 80. Junction 82 routes a portion of fluid 38 into through valves 22a', 22b', and 22c' through corresponding channels 84a, 84b, and 84c, respectively. The size of the portion of fluid 38 that flows through each channel 82 is dependent on the amount of fluid flow allowed through each valve, as described below.

Valves 22a', 22b', and 22c' are shown as on-off valves that guides fluid 38 to one of two ports on each valve. Valve 22a' is coupled to channel 84a and either guides fluid 38 to open port 86 or stops fluid flow with closed port 88. Open port 86 has an orifice of maximum size so that if the fluid is guided through port 86, and the other salves 22b' and 22c' are closed, piston 26 moves freely with the least damping resistance. Otherwise, if valve 22a' is closed (i.e. closed port 88 is selected), the fluid 38 does not flow through valve 22a.'

Valve 22b' is coupled to channel 94b and either guides fluid 38 through restricted port 90 or stops fluid flow with closed port 92. Restricted port 90 has a partially-closed orifice, similar to port 64 of FIG. 2, which restricts fluid flow through valve 22b' to a greater extent than open port 86 restricts fluid flow through valve 22a'. Thus, if fluid is guided through port 90, and valves 22a' and 22b' are closed, a greater damping resistance is generated on the movement of piston 26. Otherwise, the fluid does not flow through valve 22b' if closed port 92 is selected.

Valve 22c' is coupled to channel 84c and guides fluid 28 either through restricted port 94 or stops fluid flow with closed port 96. Restricted port 94 has a partial-closed orifice that is smaller than the orifice of restricted port 90 of valve 22b'. Thus, port 94 restricts the flow of fluid 38 to a greater extent than port 90. When valves 22a' and 22b' are closed, port 94 creates a greater damping resistance on the movement of piston 26. If closed port 96 of valve 22c' is selected, no fluid flows through valve 22c'.

Valves 22a', 22b', and 22c' can be set to operate singly or in conjunction with all valves. When operating singly, a selected valve can be opened while all other valves can be closed. This causes all of the fluid 38 to be routed to the open valve only. Flour flow rates can be selected using this method (where the selected port is fully open, restricted, more restricted, or closed). Alternatively, one or more valves can be opened simultaneously to provide additional flow rates. A total of eight different flow rates can thus be selected. For example, valves 22a' and 22b' can be opened while valve 22c' is closed, causing a damping resistance to piston 26 having a magnitude between the magnitudes of resistance generated by open valve 22a' alone and open valve 22b'alone.

Computer system 16 preferably controls valves 22a', 22b', and 22c' similarly as described with respect to FIG. 2. Electrical signals can be output on buses 97, 98, and 99 to control valves 22a', 22b', and 22c', respectively. Valves 22a', 22b' and 22c' can each be controlled by a solenoid that opens/closes the valve. Computer system 16 also receives an electrical sensor signal on bus 50 from sensor 14 to detect the position of object 14 in the provided degree of freedom.

In alternate embodiments, as described above, additional valves can be included in valve assembly 80, where a junction having the appropriate number of channels is provided. Also, the series arrangement of valves in FIG. 2 and the parallel arrangement of valves in FIG. 3a can be combined into a single embodiment for a greater variety of selectable flow rates. In addition, one or more of valves 22a', 22b' and 22c' can be implemented as servo valves that respond to an analog voltage and vary the size of orifices of the valves with a much higher resolution.

Figure 3B:
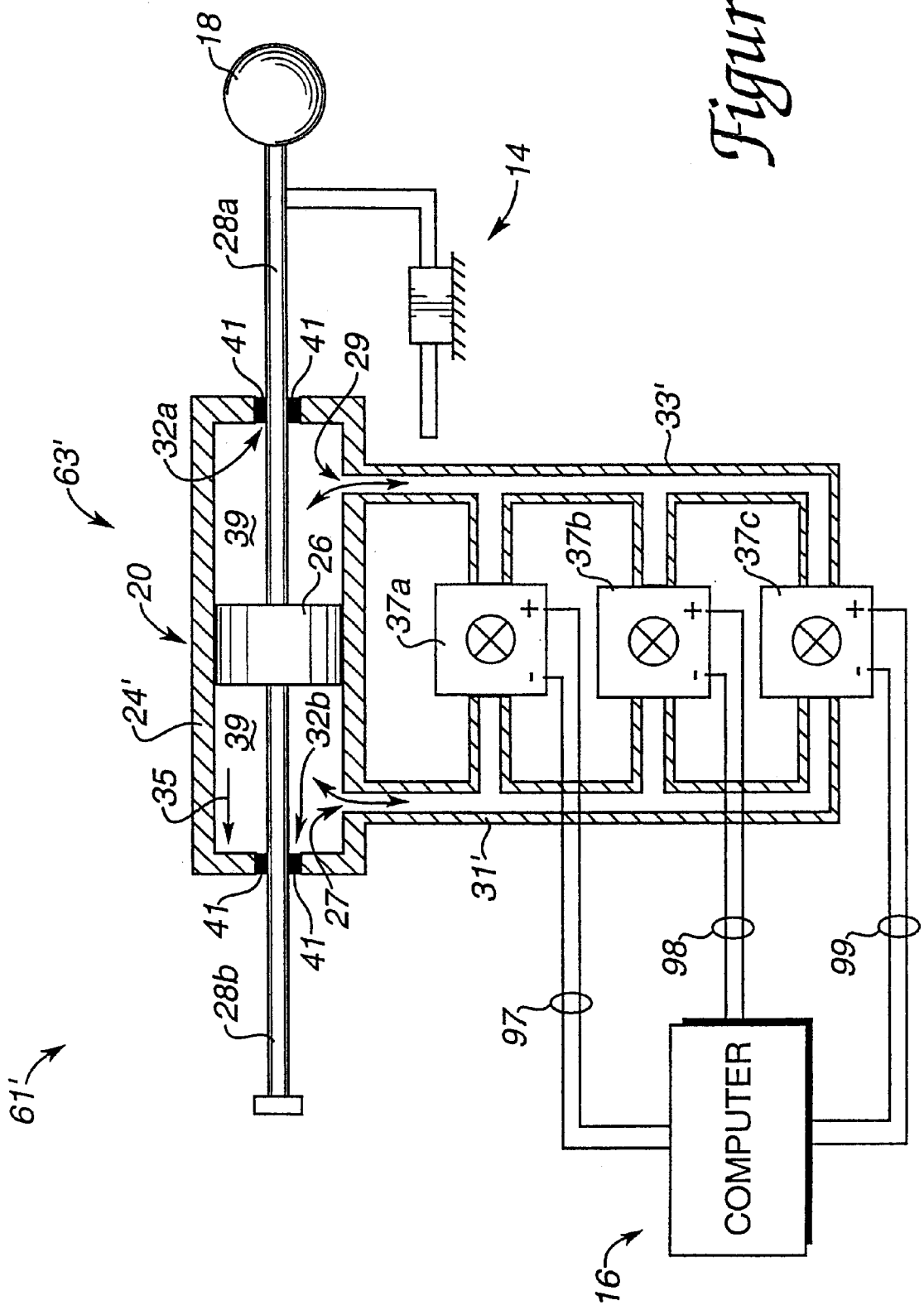
FIG. 3b is a schematic diagram of an alternate transducer system of FIG. 3a for use in hydraulic systems.

FIG. 3b is a schematic illustration of an alternate embodiment 61' of the transducer systems 10' and 61 shown in FIGS. 1b and 3a. System 61' is a closed loop system and includes a damper assembly 63', sensor 14, and user object 18 for interfacing with computer system 16. Sensor 14, computer system 16, and user object 18 are substantially similar to the corresponding components of system 61 as described with reference to FIGS. 1a and 3a.

Damper assembly 63' includes a piston assembly 20' and a valve assembly 80'. Piston assembly 20' includes cylinder 24', piston 26, piston rod 28a, piston rod 28b, orifice 27, and orifice 29. The piston 26 and piston rods 28a and 28b operate substantially the same as described with reference to FIGS. 1a and 1b and include seals 41 to prevent fluid leakages through apertures 32a and 32b. Like transducer system 10' of FIG. 1b, cylinder 24' includes two orifices 27 and 29 instead of a single orifice. Orifice 27 leads to duct 31', which extends from cylinder 24' to valve assembly 80', which includes valves 37a, 37b, and 37c. Duct 31' is an n-way junction that is preferably coupled to a first port of n valves 37a, 37b, and 37c. Similarly, orifice 29 leads to duct 33', which extends from cylinder 24' to the second port of valves 37a, 37b, and 37c. Orifices 27 and 29 are arranged such that one of the orifices is near one end of cylinder 24', and the other orifice is positioned near the opposite end of the cylinder, as described with reference to FIG. 1b.

Damper assembly 12' functions as a closed loop system as in FIG. 1b. When piston 26 is moved by the user in a direction indicated by arrow 357 fluid 39 can flow from the interior of cylinder 24' at the "front" of the cylinder, through orifice 27, through valves 37a, 37b, and/or 37c (if the particular valve is open), and into cylinder 24' through orifice 29. Likewise, when piston 26 is moved in a direction opposite to that of arrow 35, fluid 39 moves from the interior of cylinder 24', through orifice 29, through valves 37a, 37b, and 37c, through orifice 27, and back into the cylinder 24'. As described with reference to FIG. 1b, the closed loop system of FIG. 3b is most suitable for damping systems using fluids other than air.

Valves 37a, 37b and 37c of valve assembly 80' can be controlled by computer system 16 to alter the amount of fluid flowing through each of the valves. Computer system 16 can send signals over buses 97, 98, and 99, to adjust the size of an orifice in valves 37a, 37b, and 37c, respectively. In an embodiment where the valves are on-off valves, each valve 37a, 37b, and 37c can be provided with a differently-sized orifice. The amount of fluid flow can thus be controlled similarly as described with reference FIG. 3a by opening valves 37a, 37b, and 37c singly or in conjunction to provide eight different possible flow rates. In other embodiments, servo valves can be used as described above to provide a much greater selection of flow rates. In yet other embodiments, more valves 37 can be added to provide additional flow rates.

In an alternate embodiment, a electrological fluid 39' as described with reference to FIG. 1c can be provided within cylinder 24'. Electrodes can be included in valves 37a–c (or in place of valves 37a–c) to allow computer system 16 to control the viscosity of the fluid 39' and thus the damping resistance to the movement of object 18.

Figure 4A:
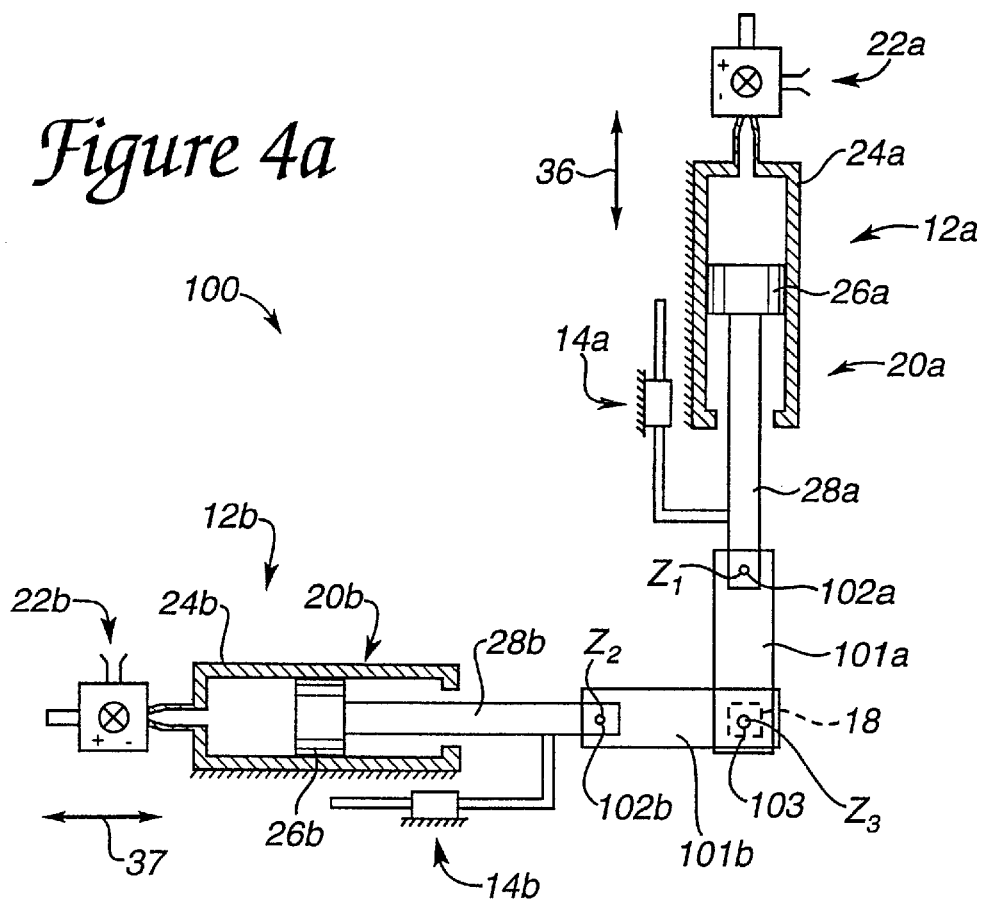
FIG. 4a is a schematic diagram of an interface system including transducer systems of FIG. 1.

FIG. 4a is a schematic illustration of an interface system 100 in which two degrees of freedom are provided to user object 18. Two transducer systems 10a and 10b as shown in FIG. 1a are included to provide two linear degrees of freedom to the object. Transducer system 10a includes a damper assembly 12a and a sensor 14a, and transducer system 10b includes a damper assembly 12b and a sensor 14b. A computer system 16 (not shown) is preferably coupled to the transducer systems 10a and 10b as shown in FIG. 1a.

As in FIG. 1a, each damper assembly 12a and 12b preferably includes a piston assembly 20a and 20b and a valve 22a and 22b. Piston assemblies 12a and 12b and sensors 14a and 14b are grounded. A piston 26a and 26b moves along a linear degree of freedom, indicated by arrows 36 and 37, respectively, within cylinders 24a and 24b, respectively. Valves 22a and 22b are preferably controlled by computer system 16 to change the damping resistance to the motion of piston 26a and 26b, respectively.

A first end of piston rod 28a is coupled to piston 26a, and a second end of piston rod 28a is coupled to a first end of joint member 101a. A rotary joint 102a couples the piston rod 28a to joint member 101a that allows joint member 101a to rotate about floating axis $Z_1$, as described below. A second end of joint member 101a is rotatably coupled to a second end of joint member 101b by a rotary joint 103. User object 18 is preferably coupled to joint member 101b (or 101a).

Piston assembly 20b has equivalent components to piston assembly 20a. Piston 26b is coupled to piston rod 28b, which is rotatably coupled to a first end of joint member 101b by a rotary joint 102b. Joint member 101b can thus rotate about floating axis $Z_2$. The second end of joint member 101b is rotatably coupled to the second end of joint member 101a by a rotary joint 103, which provides an axis of rotation $Z_3$.

Object 18 can be moved by a user along linear axis 36 or linear axis 37. When object 18 is moved along axis 36 toward or away from valve 22a, then piston 26a, piston rod 28a, and joint member 101a are correspondingly moved toward or away from valve 22a and retain the same relative position as shown in FIG. 4a. However, joint member 101b rotates about floating axis $Z_2$ and floating axis $Z_3$ in accordance with the movement of joint member 101a. Likewise, when object 18 is moved along axis 37 toward or away from valve 22b, then piston 26b, piston rod 28b, and joint member 101b are correspondingly moved toward or away from valve 22b and retain the positions as shown in FIG. 4a. Joint member 101a rotates about floating axes $Z_1$ and $Z_3$ in accordance with the movement of joint member 101b. When object 18 is moved simultaneously along both axis 36 and 37 (e.g., object 18 is moved diagonally), then both joint members 101a and 101b rotate about their respective axes.

Figure 4B:
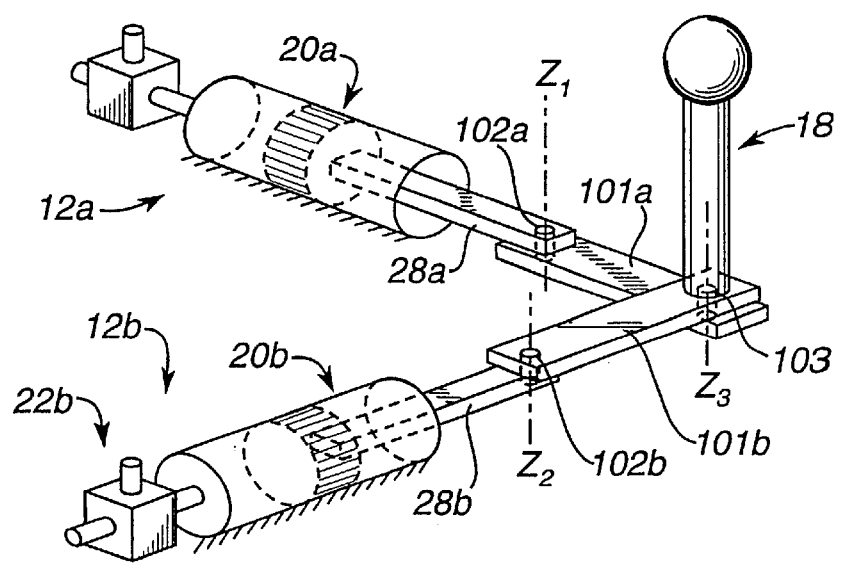

FIG. 4b is a perspective view of the interface system 100 of FIG. 4a. Piston rods 28a and 28b and joint members 101a and 101b are preferably rectilinear members that may be rotatably coupled to each other at flat surfaces of the members with rotary couplings or hinges 102a, 102b, and 103. In the described embodiment, one joint member 101a is coupled under piston rod 28a and the other joint member 101b is coupled over piston rod 28b. Alternatively, the piston rods and joint members can be coupled together in many different configurations. Object 18 can be many types of objects, and is shown as a joystick in FIG. 4b that is coupled to joint member 101b. Sensors 14a and 14b are preferably coupled to joint members 101a and 101b, respectively, but are not shown in FIG. 4b.

Figure 5A:
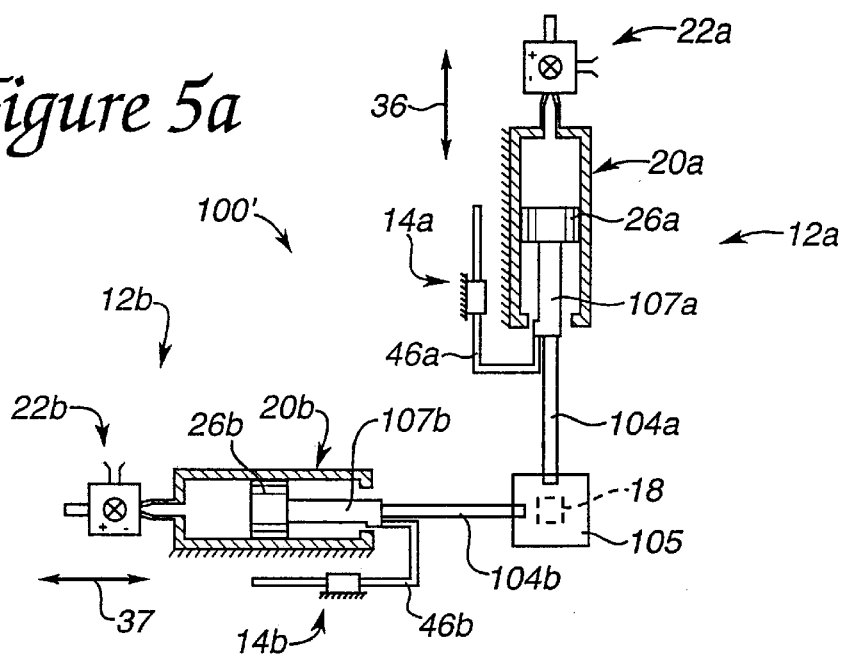

FIG. 5a is a schematic diagram of an alternate embodiment 100' of the interface system 100 shown in FIG. 4a using transducer system 10 of FIG. 1a. In FIG. 5a, two transducer systems 10a and 10b as shown in FIG. 1a are included to provide two linear degrees of freedom to object 18. Transducer system 10a includes a damper assembly 12a and a sensor 14a, and transducer system 10b includes a damper assembly 12b and a sensor 14b. A computer system 16 (not shown) is preferably coupled to the transducer systems 10a and 10b as shown in FIG. 1a.

As in FIG. 4a, each damper assembly 12a and 12b of FIG. 5a preferably includes a piston assembly 20a and 20b and a valve 22a and 22b. Piston assemblies 12a and 12b and sensors 14a and 14b are grounded. A piston 26a and 26b moves along a linear degree of freedom, indicated by arrows 36 and 37, respectively, within cylinders 24a and 24b, respectively. Valves 22a and 22b are preferably controlled by computer system 16 to change the damping resistance to the motion of piston 26a and 26b, respectively.

Piston rod 104a is a flexible member, preferably made of a resilient material such as flexible plastic, rubber, metal, or the like. As shown below in FIG. 5d, piston rods 104a and 104b are preferably narrow in the dimension that the rod is to flex, and wide in the dimensions in which the rod is to remain rigid. A rigid member 107a couples piston rod 104a to piston 26a. Rigid member 107a provides a rigid surface to couple sliding member 46a of sensor 14a to the piston 26a. In other embodiments, sensor 14a can be placed in other positions without having to use sliding member 46a (such as inside cylinder 24a ), thus permitting rigid member 107 at to have a shorter length. Piston rod 104a is rigidly coupled to an object member 105 at the other end of the piston rod. Member 105 can be a part of object 18 or a platform or other base for supporting object 18.

Damper assembly 12b is coupled to object 18 in a similar manner. Flexible piston rod 104b is coupled to piston 26b by rigid member 107b, and sliding member 46b of sensor 14b is coupled to rigid member 107b. Flexible piston rod 28b is coupled to object member 105 at its other end.

Object 18 can be moved by a user along linear axis 36 or linear axis 37. Piston rods 28a and 28b flex appropriately as the object is moved, as shown below in FIGS. 5b and 5c.

Figure 5B:
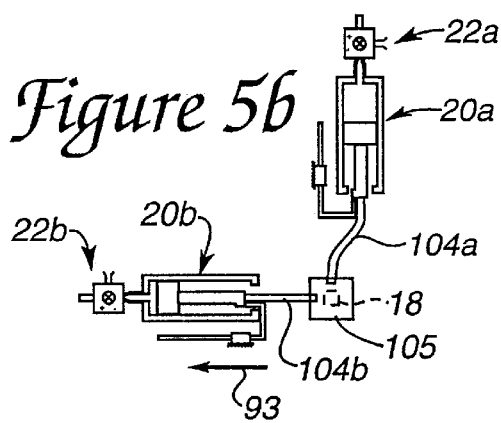

FIG. 5b shows the movement of object 18 in a single linear degree of freedom using interface system 100'. Object 18 and member 105 are moved in the direction of arrow 93. Piston rod 104b does not flex since the direction of movement is directed down (substantially parallel to) the longitudinal axis of the piston rod. However, since piston assembly 20a is grounded and fixed in place, piston rod 28a bends as shown in FIG. 5b. This occurs when the direction of movement of object 18 is substantially perpendicular to the longitudinal axis of piston rod 28a, i.e. when object 18 is moved in the linear degree of freedom indicated by arrow 37 in FIG. 5a.

Figure 5C:
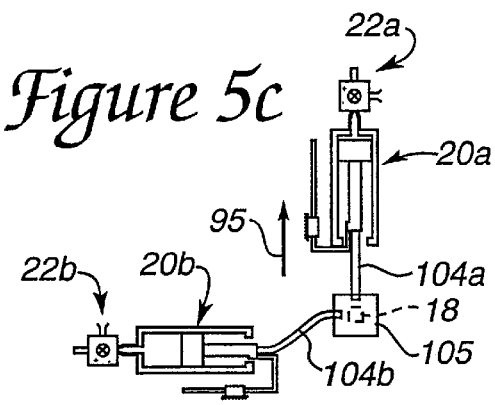

FIG. 5c shows the movement of object 18 in the other linear degree of freedom using interface system 100'. Object 18 and member 105 are moved in the direction of arrow 95. Similarly as described in FIG. 5b, piston rod 104a does not flex since the direction of movement is directed substantially parallel to the longitudinal axis of piston rod 104a. Piston rod 28a, however, bends as show,a when the direction of movement of object 18 is substantially perpendicular to the longitudinal axis of piston rod 28b, i.e. when object 18 is moved in the linear degree of freedom indicated by arrow 36 in FIG. 5a.

When object 18 is moved simultaneously along both axis 36 and 37 (e.g., object 18 is moved diagonally), then both piston rods 28a and 28b flex in conjunction with the movement.

Figure 5D:
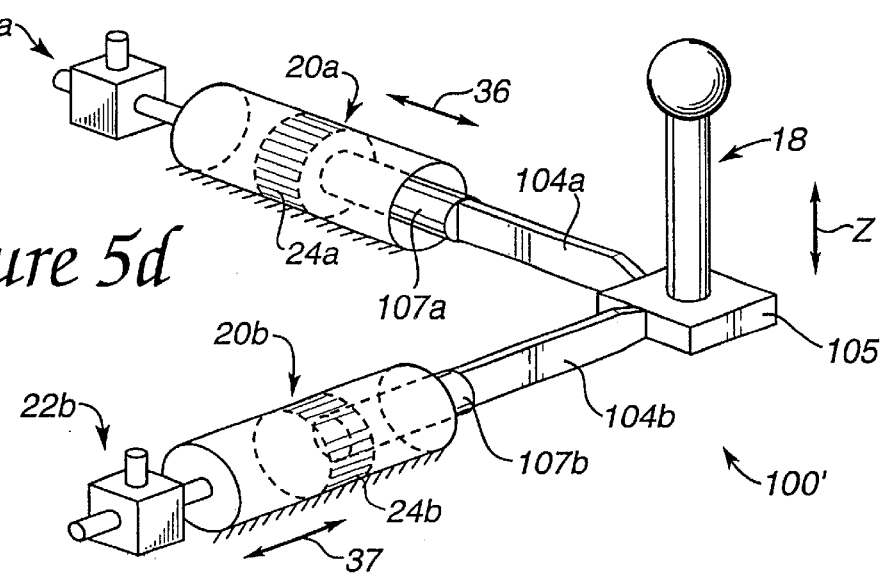

FIG. 5d is a perspective view of the interface system 100' of FIG. 5a. Piston rods 28a and 28b and rigid members 107a and 107b can be rectilinear members or have cross sections of other shapes. Preferably, piston rods 104a and 104b are narrow in the dimension in which the rod is to flex when object 18 is moved, and wide in the dimensions in which the rod is to remain rigid. For example, piston rod 104a has a relatively small width in the dimension of axis 37, since rod 104a flexes in that dimension. Correspondingly, rod 104a has a realatively large width in the dimension of axis 36 and in the dimension of axis Z, since rod 104a preferably does not flex in those dimensions. Piston rods 104a and 104b are rigidly coupled to member 105 at one end. Object 18 is shown as a joystick in FIG. 5d that is coupled to object member 105. Sensors 14a and 14b are preferably coupled to rigid members 107a and 107b, respectively, but are not shown in FIG. 5d.

FIG. 5e is a perspective view of interface system 100' of FIG. 5a in which a stylus-receiving user object 18 is provided. The interface system of FIG. 5e functions as described with reference to FIGS. 5a–5d. However, user object 18 is implemented as a stylus-receiving object 111, which is preferably a flat, small object that includes a recess, such as a stylus aperture 111a. As shown in FIG. 5f, a stylus 115 or a similar pointed article can be inserted into aperture 111a by a user. The user can then move the stylus 115 along a provided degree of freedom indicated by arrows 119, which causes object 111 to accordingly move in the same direction. Alternatively, stylus 115 can be permanently coupled to object 111.

The embodiment of FIG. 5e can be used in a writing interface where the user uses the interface to write words input to a computer system, or in a pointing interface to direct and move computer-implemented objects. The object 111 alone can be considered the "user object" 18 in this embodiment. Alternatively, both stylus 115 and object 111 can collectively be considered user object 18, particularly in embodiments where stylus 115 is permanently fixed to object 111.

FIG. 5g is a perspective view of interface system 100' of FIG. 5a in which a finger-receiving user object 18 is provided. The interface system of FIG. 5g functions as described with reference to FIGS. 5a–5d. In this embodiment, user object 18 is implemented as a finger-receiving object 113, which includes a recess, such as a divot 113a. As shown in FIG. 5h, a user may insert his or her finger into divot 113a and thereby move object 113 in the provided degrees of freedom as indicated by arrows 119. Divot 113a allows the user's finger to cling to the object 113 when the user's finger is moved. In other embodiments, features other than or in addition to divot 113a can be provided on finger-receiving object 113 to allow the user's finger to cling to the object. For example, one or more bumps, apertures, or other projections can be provided. Also, other digits or appendages of the user can be received, such as a user's entire hand, foot, etc. The interface of FIG. 5g can be used to allow the user to move, point to, or otherwise manipulate computer generated objects in an easy, natural fashion.

Figure 6A:
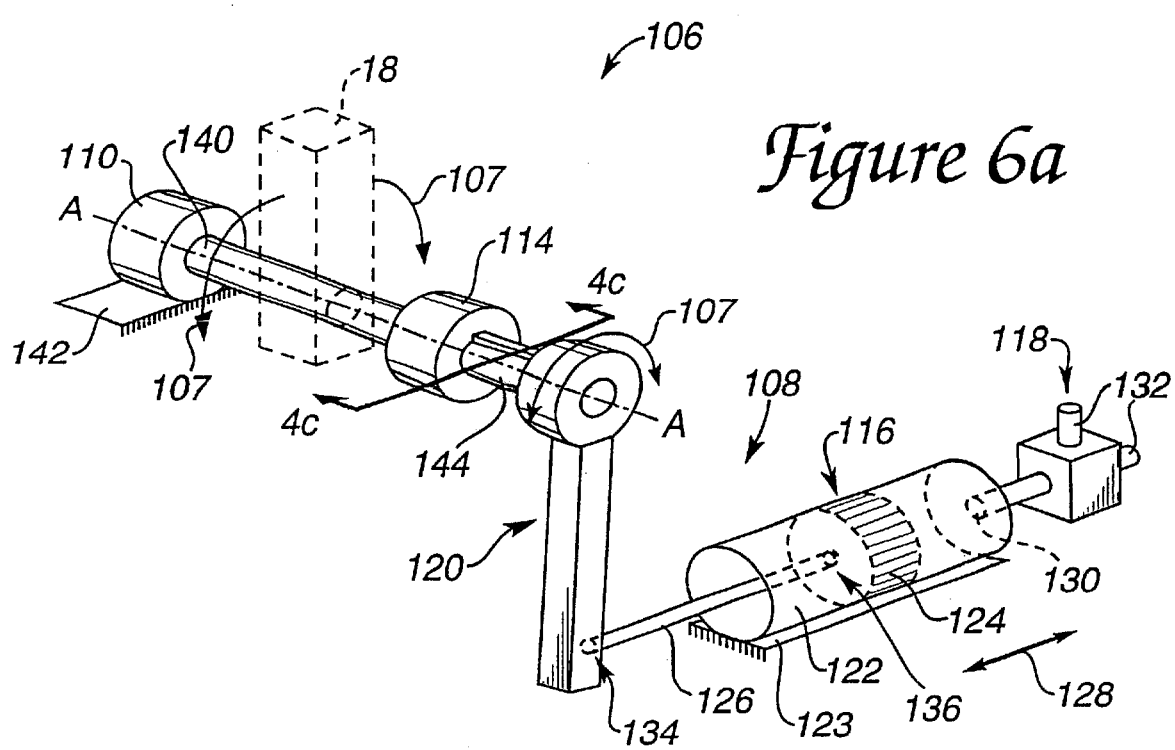
FIG. 6a is a schematic diagram of a transducer system in accordance with the present invention for providing passive force feedback to an object in a rotary degree of freedom.

FIG. 6a is a schematic illustration of a transducer system 106 sensing a rotary degree of freedom of an object and providing a passive damping resistance to the motion of the object. As shown in FIG. 4a, interface system 106 is applied to a mechanism having one degree of freedom, as shown by arrows 107. Embodiments in which system 106 is applied to systems having additional degrees of freedom are described subsequently. Transducer system 106 includes a passive damper assembly 108, a sensor 110, and an optional play mechanism 114. A computer system (not shown) is preferably coupled to the transducer system 106 similar to the embodiments shown in FIGS. 1–3.

Damper assembly 108 transmits a resistive force (i.e., drag) to an object 18 and includes a piston assembly 116, a valve 118, and a rotating member 120. Piston assembly 116 includes a cylinder 122, a piston 124, and a piston rod 126. Piston 124 moves along a linear degree of freedom within an interior of cylinder 122, as indicated by axis 128. Cylinder 122 is grounded, as shown by symbol 123. A fluid flows through an orifice 130 at the far end of cylinder 122 when piston 124 is moved within the cylinder. Valve 118 controls the fluid flow by selecting one of multiple ports 132 which provide orifice openings of varying widths. The movement of piston 124 can thus be influenced by a damping resistance related to the amount of fluid flow allowed through valve 118. Additional valves can be coupled to valve 118 in series or in parallel, as described above, to provide additional amounts of damping resistance to the movement of piston 124. Piston assembly 116 and valve 118 can thus be implemented as described above in any of the previous embodiments of FIGS. 1a, 1b, 2, 3a, or 3b. In addition, piston assembly 116 can be implemented using electrorheological fluids as described above with reference to FIG. 1c.

Rotating member 120 is coupled to piston 124 by piston rod 126. In the described embodiment, piston rod 126 is coupled to piston 124 by a ball joint 134 at one end of the piston rod. Similarly, piston rod 126 is coupled to rotating member 120 by another ball joint 136 at the other end of the piston rod. The ball joints 134 and 136 allows the piston rod to move at an angle with respect to the surfaces to which it is attached, thus permitting rotational movement of rotating member 120 to be converted into the linear movement of piston 124, as demonstrated in FIG. 4b. Other types of connections can also be provided to rotatably connect the piston to the rotatable member, as is well known to those skilled in the art.

Rotating member 120 is rigidly coupled to a main shaft 140 which extends from rotating member 120 to sensor 110. Rotating member 120 and main shaft 140 can be rotated about an axis A. Damper assembly 108 provides a rotational damping resistance or frictional force (i.e. drag) on main shaft 140 in the provided rotary degree of freedom, shown by arrows 107. Damper assembly 108 is thus passive and cannot provide an active force to shaft 140 (i.e., damper assembly 108 cannot input energy into the system to cause shaft 140 to rotate). Thus, an external rotational force, such as a force generated by a user, is applied to shaft 140, and passive damper assembly 108 provides a damping resistance to that external rotational force.

Sensor 110 is preferably rigidly coupled to shaft 114 and senses bi-directional rotary motion of main shaft 114 about axis A. Sensor 110 preferably provides a electrical signal indicating the rotational position of shaft 114 and is preferably grounded as indicated by symbol 142. In the described embodiment, sensor 110 is a digital optical encoder which provide signals to measure the angular rotation of a shaft of the sensor. In alternate embodiments, sensor 110 can be separated from object 18 and shaft 114. For example, a sensor having an emitter and detector of electromagnetic energy might be disconnected from the rest of transducer system 106 yet be able to detect the rotational position of object 18 using a beam of electromagnetic energy, such as infrared light. Similarly, a magnetic sensor could detect the position of object 18 while being uncoupled to shaft 114 or object 18. The operation of such sensors are well-known to those skilled in the art. A suitable sensor for the transducer system 106 is optical encoder model EZ marketed by U.S. Digital of Vancouver, Wash.

Sensor 110 has a sensing resolution, which is the smallest change in rotational position of coupling shaft 114 that the sensor can detect. For example, an optical encoder of the described embodiment may be able to detect on the order of about 3600 equally-spaced "pulses" (described below) per revolution of shaft 114, which is about 10 detected pulses per degree of rotational movement. Thus, the sensing resolution of this sensor is about 1/10 degree in this example. In an alternate embodiment described below, it is desired to detect the desired play between damper assembly 108 and object 18, and this desired play should not be less than the sensing resolution of sensor 110 (e.g., 1/10 degree). Preferably, the desired play between damper and object would be at least 1/15 degree in this example, since the encoder could then detect two pulses of movement, which would provide a more reliable measurement and allow the direction of the movement to be more easily determined.

Object 18 is rigidly coupled to main shaft 114. Object 18 can take a variety of forms, as described in previous embodiments, and can be directly coupled to main shaft 114 or can be coupled through other intermediate members to shaft 114. As object 18 is rotated about axis A, shaft 114 is also rotated about axis A and sensor 110 detects the magnitude and direction of the rotation of object 18.

In an alternate embodiment, a coupling 114 for introducing a desired amount of "play" can be included in interface 106, preferably positioned between the sensor 110 and the damper assembly 108. In this embodiment, main shaft 140 extends from sensor 110 to coupling 114, and a separate damper shaft 144 extends from coupling 114 to rotating member 120. Coupling 114 is rigidly coupled to main shaft 140 and non-rigidly coupled to damper shaft 144. Coupling 114 can be considered to be part of damper assembly 108 (i.e., a "braking mechanism"). Rotating member 120 is rigidly coupled to damper shaft 144.

Coupling 114 is not rigidly coupled to damper shaft 144 and thus allows an amount (magnitude) of "play" between damper shaft 144 and coupling 114. The term "play," as used herein, refers to an amount of free movement or "looseness" between a transducer and the object transduced, so that, for instance, the object can be moved a short distance by externally-applied forces without being affected by forces applied to the object by a damper. In the preferred embodiment, the user can move object 18 a short distance without fighting the drag induced by passive damper assembly 108. For example, damper assembly 108 can apply a damping resistance to damper shaft 144 so that damper shaft 144 is locked in place, even when force is applied to the shaft. Coupling 114 and main shaft 140, however, can still be freely rotated by an additional distance in either rotational direction due to the play between coupling 114 and shaft 144. This play is intentional in this embodiment for purposes that will be described below, and is thus referred to as a "desired" amount of play. Once coupling 114 is rotated to the limit of the allowed play, it either forces shaft 144 to rotate with it further; or, if damper assembly 108 is holding (i.e., locking) shaft 144, the coupling cannot be further rotated in that rotational direction. The amount of desired play between damper assembly 108 and object 18 greatly depends on the resolution of the sensor 110 being used, and is described in greater detail below. Examples of types of play include rotary backlash, such as occurs in gear systems as described in the above embodiments, and compliance or torsion flex, which can occur with flexible, rotational and non-rotational members. An embodiment including backlash is described in greater detail below with reference to FIG. 4c. Coupling 114 and/or shaft 144 can be considered a "play mechanism" for providing the desired play between damper assembly 108 and object 18. Object 18 can also be coupled directly to coupling 114. Alternatively, sensor 110 can be positioned between coupling 114 and object 18 on main shaft 140. Shaft 140 would extend through sensor 110 and can be rigidly coupled to object 18 at the end of the shaft.

In this alternate embodiment including coupling 114, sensor 110 should be as rigidly coupled to main shaft 140 as possible so that the sensor can detect the desired play between shaft 144 and object 18. Any play between sensor 110 and object 18 should be minimized so that such play does not adversely affect the sensor's measurements. Typically, any inherent play between sensor 110 and object 18 should be less than the sensing resolution of the sensor, and preferably at least an order of magnitude less than the sensing resolution. Thus, in the example above, the play between sensor and object should be less than 1/10 degree and preferably less than 1/100 degree. Use of steel or other rigid materials for shaft 114 and other components, which is preferred, can allow the play between sensor 110 and object 18 to be made practically negligible for purposes of the present invention. As referred to herein, a sensor that is "rigidly" coupled to a member has a play less than the sensing resolution of the sensor (preferably a negligible amount). The play between damper assembly 108 and object 18 is described in greater detail below. A suitable encoder to be used for sensor 110 is the "Softpot" from U.S. Digital of Vancouver, Wash.

As stated above, coupling 114 is suited for mechanical systems that include the low-cost damper assembly 108. If a controlling computer system, such as computer system 16, is to provide force feedback to object 18 being held and moved by a user, the computer system should be able to detect the direction that the user is moving the object even when the damper assembly is applying maximum force to the object to lock the object in place. However, when using pneumatic passive dampers of the present invention which do not inherently allow a measurable amount of play, such detection is difficult. The pneumatic dampers of FIG. 4a provide a resistive force or friction to motion in both rotational directions about axis A (i.e., bi-directional resistance). Thus, when force from a damper prevents movement of an object in one direction, it also prevents movement in the opposite direction. This typically does not allow the sensors to transduce movement of the object in the opposite direction, unless the user overpowers the damper by providing a greater force than the damper's resistive force. This also applies to the linear movement as shown with respect to FIGS. 1–3, i.e., linear play can be implemented instead of rotary play. Compliance or backlash can be implemented between linearly moving (i.e., translatable) components. For example, sensor 14 can be rigidly coupled to object 18 as shown in FIG. 1a, but the connection between piston 26 and object 18 can include an amount of play provided by a small spring, flexible member, etc. Or, a small amount of space can be provided between interlocked translatable components to provide play in accordance with the present invention.

For example, object 18 may be a one-degree-of-freedom joystick used for moving a video cursor that moves in the direction indicated by the joystick on a video screen. The user moves the cursor into a virtual (computer generated) "wall", which blocks the motion of the cursor in one direction. The controlling computer system also applies force feedback to the joystick by closing valve 118 to prevent the user from moving the joystick in the direction of the wall, thus simulating the surface of the wall. If sensor 110 is rigidly coupled to damper shaft 114, a problem occurs if the user wishes to move the joystick in the opposite direction to the wall. Since the damper has locked the joystick in both directions, the computer cannot detect when the user switches the joystick's direction unless the user overpowers the damper. Thus, to the user, the cursor feels like it is "stuck" to the wall.

Applicant's introduced ("desired") play between object 18 and damper assembly 108 solves this problem effectively and inexpensively. The play allows the joystick or other connected object to be moved slightly in the opposite direction even when the damper applies maximum resistance to the joystick's movement. The sensor, being rigidly attached to the joystick, is not locked by the damper and detects the change in direction. The sensor relays the movement to the computer, which opens valve 118 to allow the joystick to be moved freely in the opposite direction. Thus the play mechanism allows "uni-directional" resistance to be simulated on the user object. If the user should move the cursor into the wall again, the valve would be again be similarly closed. A method for controlling damper assembly 108 to provide such uni-directional resistance is described with reference to FIG. 16.

In many embodiments of the present invention, such desired play may not be necessary. For example, when using pneumatic piston assemblies, there is typically an amount of play that inherently exists when the valve is closed to due air leakages in the piston cylinder and the compressibility of air. Thus, the piston will be able to be moved a small amount when maximum damping resistance is applied. The sensor 14 or 110 can be rigidly coupled to the object to detect this play movement. This type and similar types of damper assemblies thus may not need coupling 114 and damper shaft 144 to provide the desired play and unidirectional resistance.

Other devices or mechanisms besides the use of play can be used in other embodiments to detect the direction of motion of object 18 while passive dampers are holding the object in place. For example, force sensors can be coupled to the object to measure the force applied to the object by the user along desired degrees of freedom, A force sensor can detect if a user is applying a force, for example, towards the virtual wall or away from the virtual wall, and the computer can activate or deactivate the passive dampers accordingly. Deliberately-introduced play between object and damper is thus not required in such an embodiment. However, such force sensors can be expensive and bulky, adding to the cost and size of the interface mechanism.

Figure 6B:
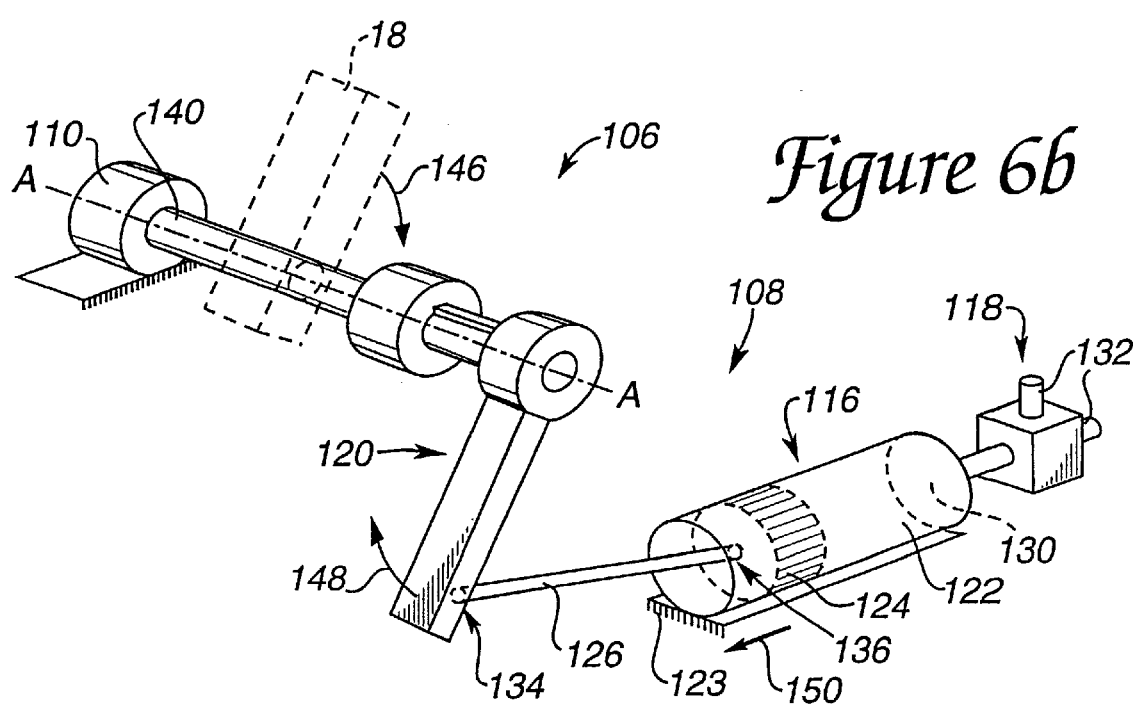
FIG. 6b is a schematic diagram of the transducer system of FIG. 4a where an object has been moved within the rotary degree of freedom.

FIG. 6b is a schematic diagram of transducer system 106. Object 18 has been moved by the user about axis A in the direction indicated by arrow 146. Accordingly, shaft 140 and thus rotating member 120 rotate in the same direction, as indicated by arrow 148. This causes piston 124 to move in the direction of arrow 150. As shown in FIG. 6b, ball joints 134 and 136 allow piston rod 126 to follow the rotational movement of rotating member 120 and cause the linear movement of piston 124 without any stress or bending of the piston rod.

Figure 6C:
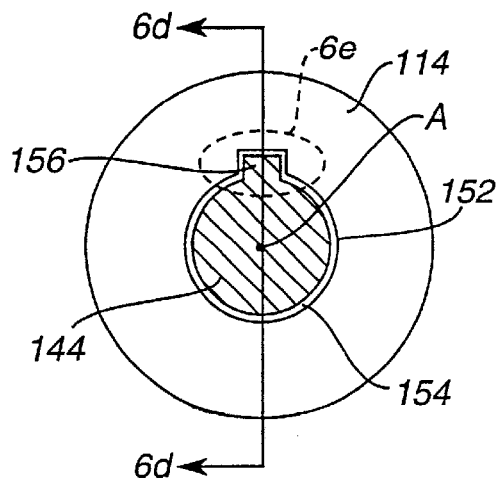

FIG. 6c is a side sectional view of damper shaft 144 and coupling 114 taken along line 6c—6c of FIG. 6a as used in the alternate embodiment in which a desired amount of play is provided between damper assembly 108 and object 18. In this described embodiment, rotary backlash is used to provide play between damper assembly 108 and coupling 114. In alternate embodiments, backlash can be provided between damper 108 and coupling 114 using different components, such as gears, pulleys, etc. Damper shaft 144 is keyed and is rigidly coupled to damper assembly 108 (rotating member 120). Keyed shaft 144 mates with keyed coupling 114. The cross-sectional diameter of keyed damper shaft 144 is preferably smaller than bore 152 of coupling 114, to provide the desired backlash. Keyed shaft 144 extends into keyed bore 152 of coupling 114. In FIG. 6c, gap 154 is provided around the entire perimeter of shaft 144. In alternate embodiments, gap 154 can be provided only between the sides of the keyed portion 156 of shaft 144, as described with reference to FIG. 6e.

Figure 6D:
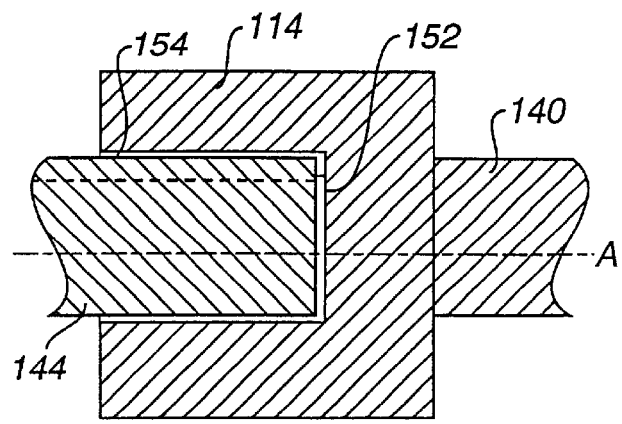
FIG. 6d is a sectional side view of the damper shaft and play mechanism of FIG. 6c.

FIG. 6d is a side sectional view of keyed damper shaft 144 and coupling 114 taken along line 6d—6d of FIG. 6c. Keyed shaft 144 is shown partially extending into coupling 114 shown in FIG. 6c, small gap 154 is preferably provided between coupling 114 and shaft When shaft 144 is rotated, coupling 114 is also rotated after the keyed portion of shaft 144 the keyed portion of bore 152, as described with reference to FIG. 6e. Main shaft 14 coupling 114 rotates, since it is rigidly attached.

Figure 6E:
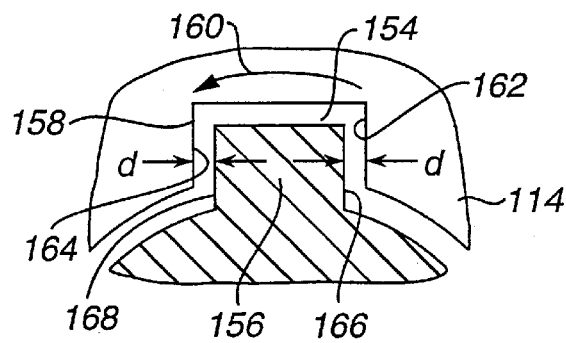
FIG. 6e is a detailed view of the keyed portions of the damper shaft and play mechanism of FIG. 6c.

FIG. 6e is a detailed view of FIG. 6c showing the keyed portions of shaft 144 and bore 152. Extended keyed portion 156 of shaft 152 protrudes into receiving keyed portion 158 of bore 152. In alternate embodiments, an extended keyed portion of coupling 114 can protrude into a receiving keyed portion of shaft 144. Gap 154 has a width d which determines how much desired backlash (play) is introduced between damper assembly 108 and object 18. (Additional unintentional backlash or other inherent play can exist between the components of the system due to compliance of the shafts, etc.) In the described embodiment, in which sensor 110 has a sensing resolution of about $\frac{1}{10}$ degree, d is preferably about $\frac{1}{1000}$ inch. Note that the distance d can widely vary in alternate embodiments. The chosen distance d is preferably made small enough to prevent the user from feeling the backlash that exists in the system when handling object 18 and yet is large enough for the sensor to detect the play (i.e., greater than the sensing resolution of sensor 110) to allow the sensor to inform the computer the direction that the user is moving object 18. Thus, the distance d is highly dependent on the sensing resolution of sensor 110. For example, if a sensing resolution of $\frac{1}{100}$ degree is available, the distance d can be much smaller. The amount of backlash that a user can typically feel can depend on the size and shape of object 18; however, the backlash described above is not detectable by a user for the majority of possible objects. In other embodiments, it may be desirable to allow the user to feel the backlash or other play in the system, and thus a greater distance d can be implemented.

In the preferred embodiment, distance d allows rotational movement of coupling 114 at least equal to the sensing resolution of sensor 110 in either direction, thus allowing a total backlash of distance of 2d between surfaces 162 and 164 of coupling 114. Alternatively, a total backlash of distance d between surfaces 162 and 164 can be implemented (half of the shown distance). In such an embodiment, however, sensor 110 would only be able to detect movement from one limit of the backlash to the other limit, and, for example, movement of coupling 114 from a center position (as shown in FIG. 6e) would not be detected.

In the described embodiment, digital encoder sensors 110 are used, in which rotational movement is detected using a number of divisions on a wheel that are rotated past fixed sensors, as is well known to those skilled in the art. Each division causes a "pulse,", and the pulses are counted to determine the amount (magnitude) of movement. Distance d can be made as large or larger than the sensing resolution of the encoder so that the magnitude and direction of the movement within gap 154 can be detected. Alternatively, the resolution of the sensor can be made great enough (i.e., the distance between divisions should be small enough, in a digital encoder) to detect movement within gap 154. For example, two or more pulses should be able to be detected within distance d to determine the direction of movement of object 18 and coupling 114 using a digital encoder or the like.

When coupling 114 is initially rotated from the position shown in FIG. 6e in a direction indicated by arrow 160 (counterclockwise in FIG. 6c) as the user moves object 18, the coupling freely rotates. Coupling 114 can no longer be rotated when the inner surface 162 of keyed portion 158 engages surface 166 of keyed portion 156. Thereafter, external force (such as from the user) in the same direction will cause either both coupling 114 and shaft 144 to rotate in the same direction, or the external force will be prevented if damper assembly 108 is locking shaft 144 in place with high resistive force to prevent any rotational movement of shaft 144.

If the user suddenly moves object 18 in the opposite rotational direction after surface 162 has engaged surface 166, coupling 114 can again be rotated freely within gap 154 until surface 164 of bore 152 engages surface 168 of shaft 144, at which point both shaft and coupling are rotated (or no rotation is allowed, as described above). It is the magnitude and direction of the movement between the engagement of the surfaces of keyed portions 156 and 158 which can be detected by sensor 110, since sensor 110 is rigidly coupled to coupling 114. Sensor 110 can relay the direction which coupling 114 (and thus object 18) is moving to the controlling computer, and the computer can deactivate or activate damper assembly 108 accordingly, Even if object 18 is held in place by damper assembly 108, as when moving into a virtual "wall", the computer can detect the backlash movement of object 18 if the user changes the direction of the object and can remove the damper resistance accordingly. It should be noted that computer 16 should preferably deactivate the passive damper (e.g., open valve 118) before surface 164 engages surface 168 so that the user will not feel any resistance to movement in the opposite direction.

Instead of implementing play as rotary backlash, as described above, torsion flex or compliance can be provided in the shafts to provide the desired amount of play. A flexible coupling 114 can take many possible forms, as is well known to those skilled in the art. The flexible coupling can allow main shaft 140 to rotate independently of damper shaft 144 for a small distance, then force damper shaft 144 to rotate in the same direction as coupling shaft 140. Compliance or flex can be provided with spring members and the like. However, fluid resistance devices such as pneumatic piston/cylinders may include an amount of inherent compliance, so that a flexible coupling may not be needed.

Figure 7:
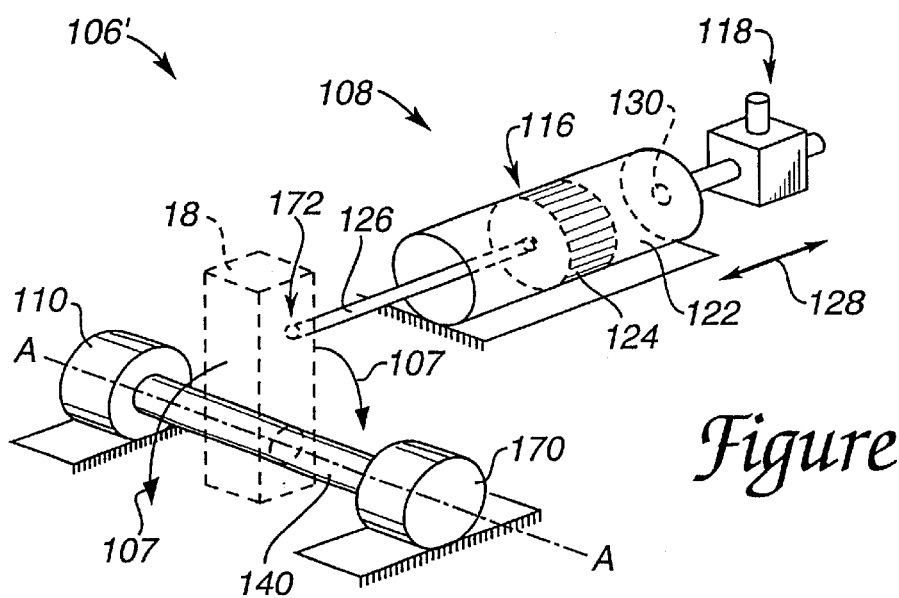

FIG. 7 is a schematic diagram of an alternate embodiment 106' of transducer system 106. Embodiment 106' is similar to system 106 except for the placement of the damper assembly 108. Object 18 is coupled to main shaft 140, which rotates about axis A. Sensor 110 is rigidly coupled to main shaft 140 and operates as described with respect to FIG. 6a. Opposite coupling 170 is provided at the end of main shaft 140 opposite to sensor 110 to provide support.

Damper assembly 108 is substantially similar to the damper assembly shown in FIG. 6a, and includes a piston assembly 116 and a valve 118. Piston assembly 116 includes a piston cylinder 122, a piston 124, and a piston rod 126 coupled to piston 124 at one end. However, instead of coupling the other end of piston rod 126 to a rotating member 120, the rod end is coupled to object 18 with a ball joint 172 similar to the ball joint 134 shown in FIG. 6a. When object 18 is rotated about axis A, as shown by arrows 107, piston rod 126 and piston 124 are also moved in a linear direction along axis 128. The fluid flow through orifice 130 and valve 118 is to the motion of object 18.

Figure 8:
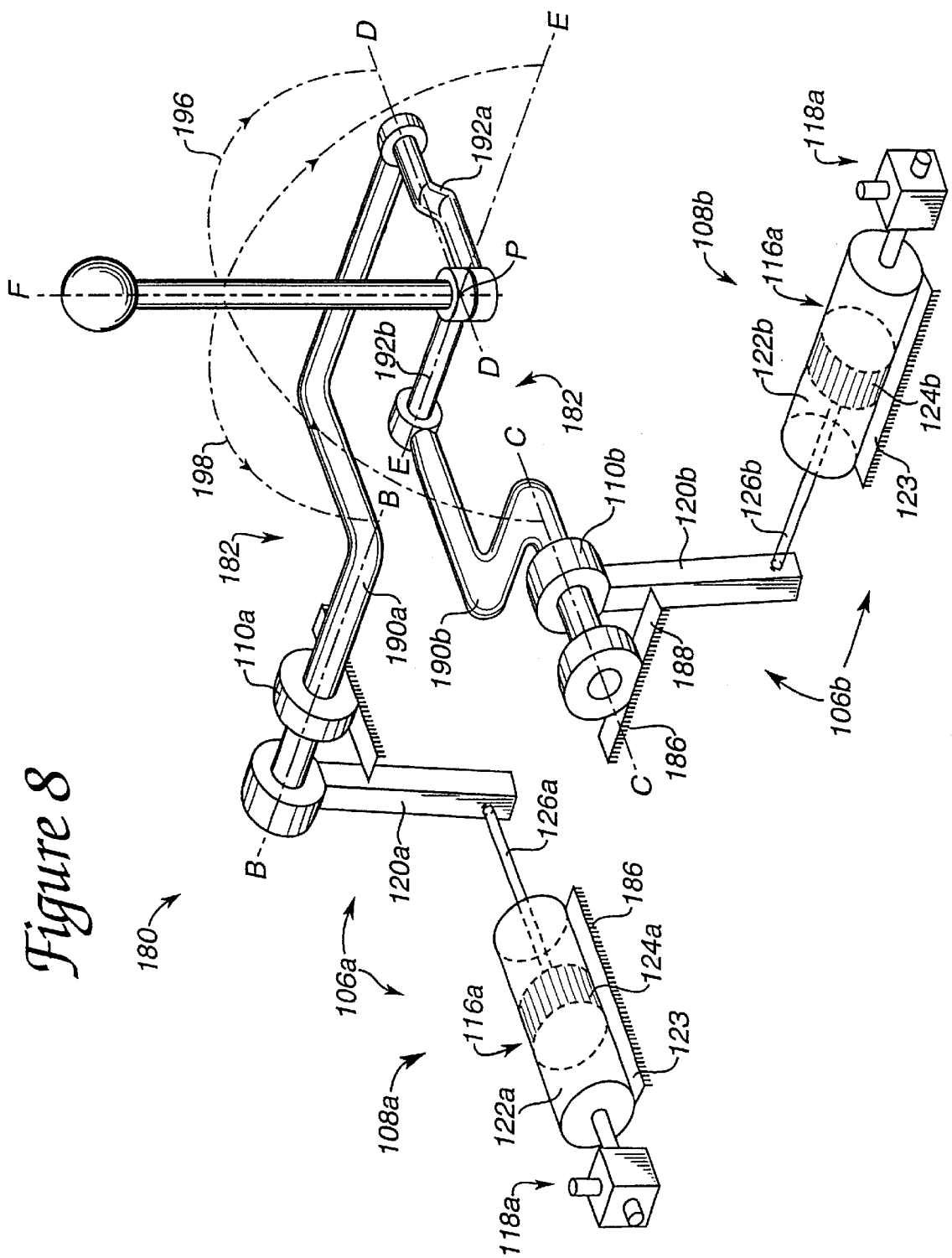

FIG. 8 is a schematic diagram of a preferred interface system 180 in accordance with the present invention that provides two or three degrees of freedom to user object 18 and mechanical input and output. System 180 includes a gimbal mechanism 182, optional linear axis member 184, transducer systems 106a and 106b, and user object 18.

Gimbal mechanism 182, in the described embodiment, provides support for system 180 on a grounded surface 186 (schematically shown as part of member 188). Gimbal mechanism 182 is preferably a five-member linkage that includes a ground member 188, extension members 190a and 190b, and central members 192a and 192b. Ground member 188 is coupled to a base or surface which provides stability for system 180. Ground member 188 is shown in FIG. 8 as two separate members coupled together through grounded surface 186. The members of gimbal mechanism 182 are rotatably coupled to one another through the use of bearings or pivots, wherein extension member 190a is rotatably coupled to ground member 188 and can rotate about an axis B, central member 192a is rotatably coupled to extension member 190a and can rotate about a floating axis D, extension member 190b is rotatably coupled to ground member 188 and can rotate about axis C, central member 192b is rotatably coupled to extension member 190b and can rotate about floating axis E, and central member 192a is rotatably coupled to central member 192b at a center point P at the intersection of axes D and E. The axes D and E are "floating" in the sense that they are not fixed in one position as are axes B and C. Axes B and C are substantially mutually perpendicular. As used herein, "substantially perpendicular" will mean that two objects or axis are exactly or almost perpendicular, i.e. at least within five degrees or ten degrees of perpendicular, or more preferably within less than one degree of perpendicular. Similarly, the term "substantially parallel" will mean that two objects or axis are exactly or almost parallel, i.e. are at least within five or ten degrees of parallel, and are preferably within less than one degree of parallel.

Gimbal mechanism 182 is formed as a five member closed chain. Each end of one member is coupled to the end of a another member. The five-member linkage is arranged such that extension member 190a, central member 192a, and central member 192b can be rotated about axis B in a first degree of freedom. The linkage is also arranged such that extension member 190b, central member 192b, and central member 192a can be rotated about axis B in a second degree of freedom.

Also preferably coupled to gimbal mechanism 182 are transducer systems 106a and 106b for transducing rotary degrees of freedom, including sensors and dampers as described in FIG. 6a. Such transducer systems are preferably coupled at the link points between members of the apparatus and provide input to and output from an electrical system, such as computer system 16. Transducer systems 106a and 106b preferably include damper assemblies 108a and 108b and sensors 110a and 110b, respectively. Damper assemblies 108a and 108b include piston assemblies 116a and 116b, respectively, and valves 118a and 118b, respectively. Piston assemblies 116a and 116b each include a cylinder 122, a piston 124, a piston rod 126, and a rotatable member 120, as described with reference to FIG. 6a. Ground member 123 of the piston assemblies can be the same as ground member 188, or a different ground member. A computer system 16 (not shown) is preferably electrically connected to sensors 110 and valves 118 to control the sensors and dampers with electrical signals, as described in the above transducer embodiments.

As described above in FIG. 6a, damper assemblies 108a and 108b are passive dampers that provide damping resistance to the motion of object 18 in a degree of freedom and sense the position of object 18 in that degree of freedom. Transducer system 106a transduces the motion of object 18 in the rotary degree of freedom about axis B (and/or floating axis E), and transducer system 106*b* transduces the motion of object 18 in the rotary degree of freedom about axis C (and/or floating axis D).

User object 18 is coupled to interface system 180. Object 18 can be coupled to central member 192*a* or 192*b*, for example, at intersection point P. Object 18 is preferably an interface object for a user to grasp or otherwise manipulate in three dimensional (3D) space. Suitable user objects are described with the transducer systems of FIGS. 1–5. User object 18 may be moved in the two degrees of freedom provided by gimbal mechanism 182. As user object 18 is moved about axis B, floating axis E varies its position, and as user object 18 is moved about axis C, floating axis F varies its position.

It should be noted that interface system 180 is only one particular embodiment of a mechanism for implementing two or more degrees of freedom. The passive transducer systems 10 and 106 of the present invention can be used with a variety of mechanical apparatuses, such as slotted yoke joystick mechanisms, other types of gimbal mechanisms, etc., which are well known to those skilled in the art. A slotted yoke joystick mechanism is described below with reference to FIG. 11.

In alternate embodiments, user object 18 can be provided with additional degrees of freedom using the gimbal mechanism of interface system 180. For example, a linear degree of freedom can be provided to joystick 18 in FIG. 8 by allowing the joystick to be linearly moved along floating axis F as shown in FIG. 8. Joystick 18 can be translatably coupled to the ends of central members 190*a* and 190*b*. Axis F can be rotated about axes B,C, D, and E as joystick 18 is rotated about these axes, A transducer system 10 or 106 can be provided to sense and/or dampen movement along axis F. Additional degrees of freedom can be provided to object 18 as well, for example, using a floating gimbal mechanism or other mechanical apparatus.

Figure 9:
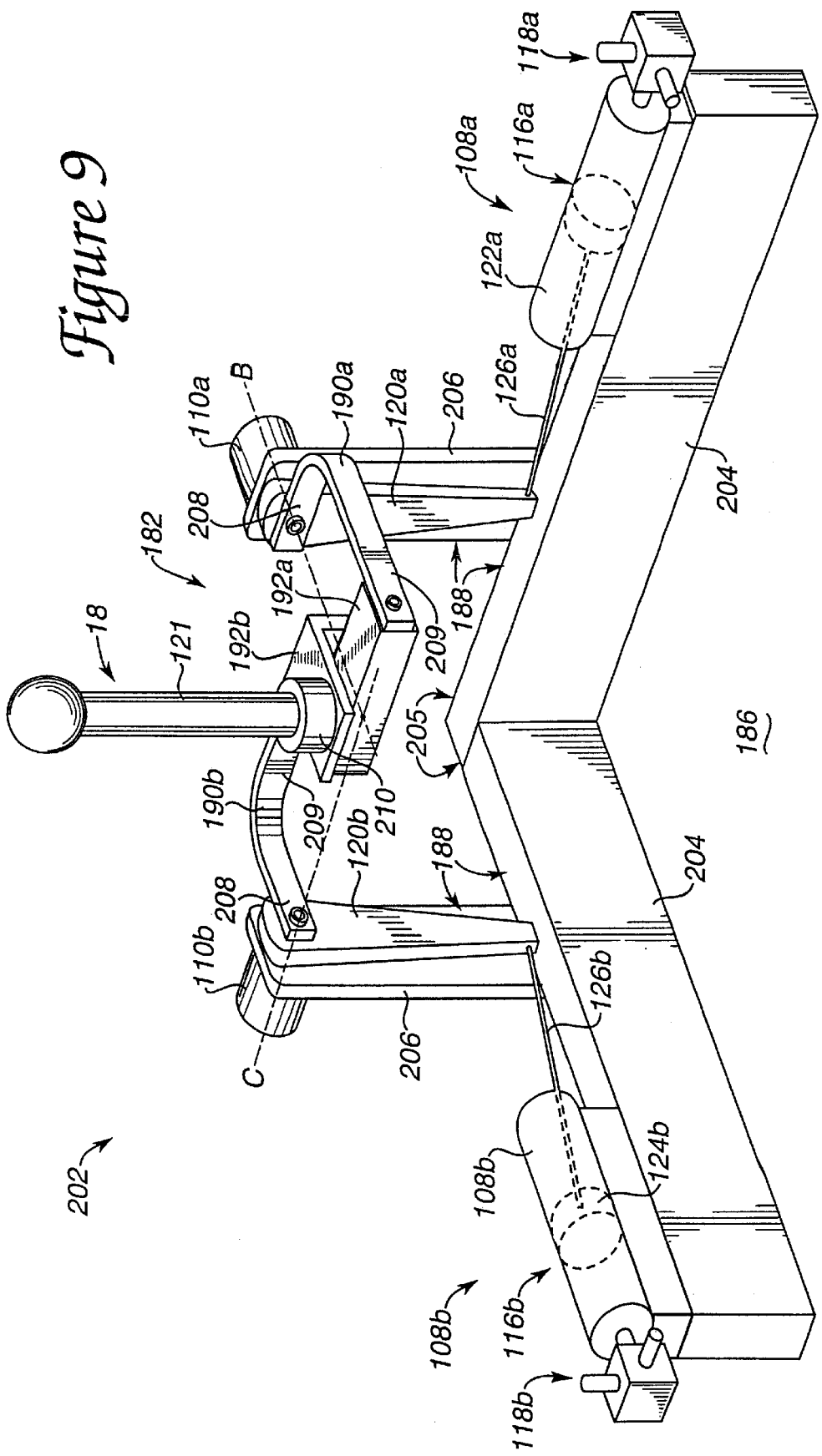
FIG. 9 is a perspective front view of a preferred embodiment of the interface system of FIG. 8 including a joystick object.
Figure 10:
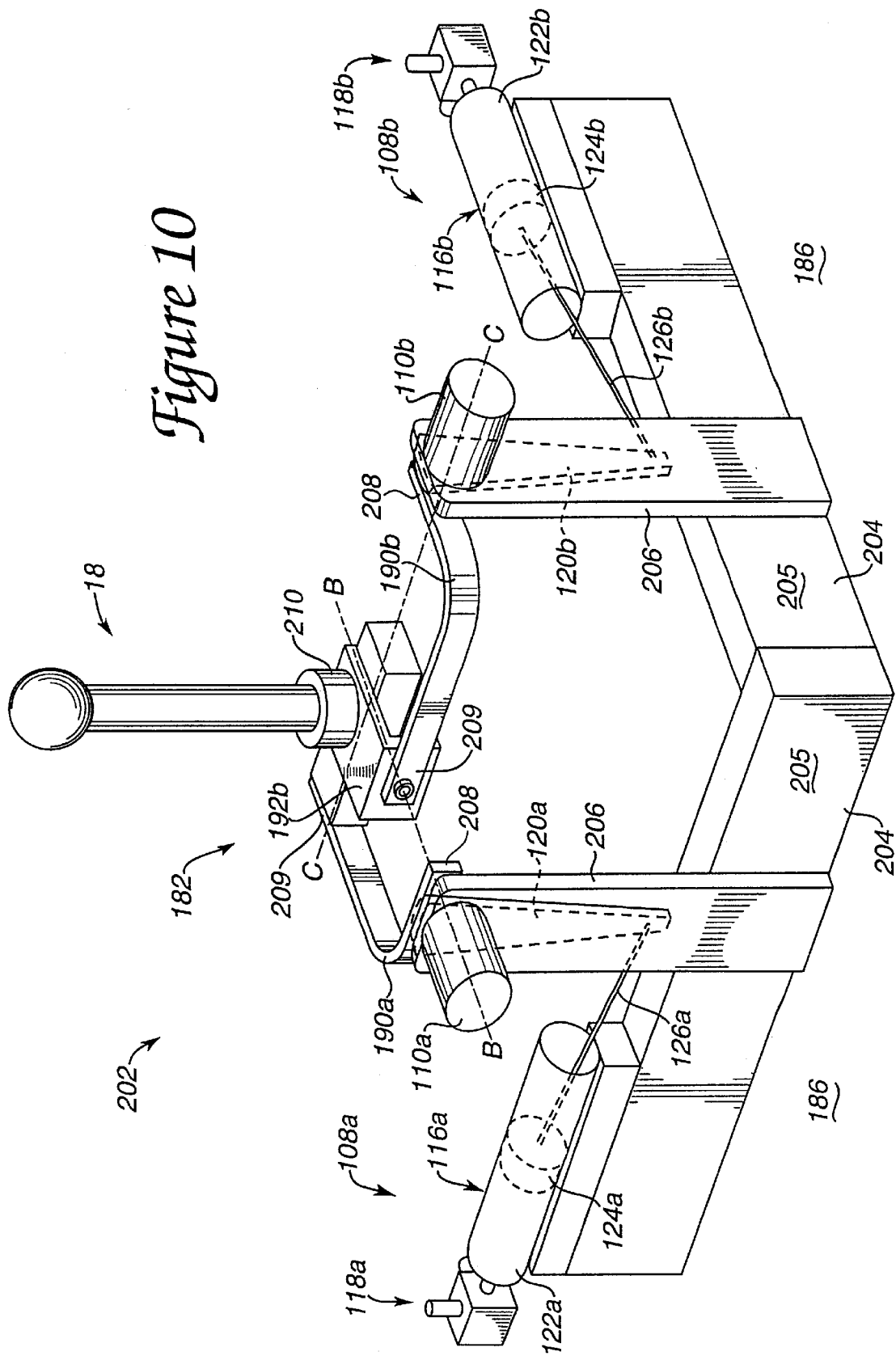
FIG. 10 is a perspective rear view of the embodiment of the interface system of FIG. 9.

FIGS. 9 and 10 are perspective views of a specific embodiment 202 of interface system 180 for providing two degrees of freedom to object 18 and mechanical input and output to a computer system in accordance with the present invention. FIG. 9 shows a front view of system 202, and FIG. 10 shows a rear view of the system. System 202 includes a gimbal mechanism 182, sensors 110, damper assemblies 108, and user object 18. Object 18 is shown in this embodiment as a joystick handle which can be moved in two degrees of freedom. Interface system 202 operates in substantially the same fashion as system 180 described with reference to FIG. 8.

Gimbal mechanism 182 provides support for system 202 on a grounded surface 186, such as a table top or similar surface. The members and joints ("bearings") of gimbal mechanism 182 are preferably made of a lightweight, rigid, stiff metal, such as aluminum, but can also be made of other rigid materials such as other metals, plastic, etc. Gimbal mechanism 182 includes a ground member 188, extension members 190*a* and 190*b*, central drive member 192*a*, and central link member 192*b*. Ground member 188 includes a base member 204 and vertical support members 206. Base member 204 can be coupled to grounded surface 186 (or may rest on grounded surface 186) and provides two outer vertical surfaces 205 which are in a substantially perpendicular relation which each other. A vertical support member 206 is coupled to each of these outer surfaces of base member 204 such that vertical members 206 are in a similar substantially 90-degree relation with each other.

Rotating members 120*a* and 120*b* are each preferably rotatably coupled to a vertical member 206. Member 120*a* rotates about axis B and member 120*b* rotates about axis C. Rotating members 120*a* and 120*b* function as described above with reference to FIGS. 6*a* and 8.

Extension member 190*a* is rigidly coupled to rotating member 120*a* and is rotated about axis B as the rotating member is rotated. Likewise, extension member 190*b* is rigidly coupled to the other rotating member 120*b* and can be rotated about axis C. Both extension members 190*a* and 190*b* are formed into a substantially 90-degree angle with a short end 208 coupled to rotating members 120*a* and 120*b*. Central drive member 192*a* is rotatably coupled to a long end 209 of extension member 190*a* and extends at a substantially parallel relation with axis C. Similarly, central link member 192*b* is rotatably coupled to the long end of extension member 190*b* and extends at a substantially parallel relation to axis B (as better viewed in FIG. 10). Central drive member 192*a* and central link member 192*b* are rotatably coupled to each other at the center of rotation of the gimbal mechanism, which is the point of intersection P of axes B and C. Bearing 210 connects the two central members 192*a* and 192*b* together at the intersection point P.

Gimbal mechanism 182 provides two degrees of freedom to an object positioned approximately at or coupled to the center point P of rotation. An object approximately at or coupled to point P can be rotated about axis B or C or have a combination of rotational movement about these axes (when a combination of rotational movement is implemented, the object actually rotates about the floating axes D and/or E instead of axes C and/or B, respectively, as shown and described with reference to FIG. 8).

Damper assemblies 108*a* and 108*b* are preferably coupled to gimbal mechanism 182 to provide input and output signals between interface system 202 and computer system 16 (not shown). Damper assembly 108*a* is coupled to ground member 204 and to extension member 190*a*, and likewise damper assembly 108*b* is coupled to ground member 204 and to extension in member 190*b*. As described in the above embodiments, damper assemblies 108*a* and 108*b* each preferably include a piston assembly 116 and a valve 118, where the piston assembly includes a cylinder, piston, and piston rod which couples the piston to a corresponding rotating member 120. Computer system 16 can control the flow of a fluid through the piston cylinders and valves by sending and receiving electrical signals to the valves, as described above. Damper assembly 108*a* thus provides damping resistance to the motion of object 18 in the first degree of freedom about axis B (or floating axis E), and damper assembly 108*b* provides damping resistance to the motion of object 18 in the second degree of freedom about axis C (or floating axis D).

Sensors 110*a* and 110*b* are provided to detect the position of the object 18 about the two degrees of freedom and relay this position to computer system 16. The cylinder of grounded sensor 110*a* is preferably coupled to the outside surface of a vertical support member 206 and measures the position of object 18 in the first degree of freedom about axis B (or axis E), i e, sensor 110*a* is "associated with" or "related to" the first degree of freedom. A rotational shaft of sensor 110*a* is coupled to main shaft 140 which extends from extension member 190*a*, through rotating member 120*a*, through vertical member 206, to sensor 110 to transmit rotational movement along the first degree of freedom. Sensor 110*b* preferably corresponds to sensor 110*a* in function and operation, except that sensor 110*b* is associated with a second degree of freedom about axis C (or axis D). Sensor 110*b* is coupled to the other vertical support member 206. In alternate embodiments, sensors 110*a* and 110*b* can be positioned in other locations on gimbal mechanism 182. For example, the sensors can be coupled to their corresponding extension members 190a and 190b on the opposite side of vertical members 206 shown in FIGS. 9 and 10.

Sensors 110a and 110b are preferably relative optical encoders which provide signals to measure the angular rotation of a shaft extending through the sensor. The electrical outputs of the encoders are routed to computer system 16 via buses as detailed with reference to FIGS. 1a, 12, and 13. Other types of sensors can also be used, such as potentiometers, linear encoders, etc.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system power-up wherein the sensor's shaft is placed in a known position within the interface system 202 and a calibration signal is provided to the system to provide the reference position mentioned above. All angles provided by the sensors are thereafter relative to that reference position. Such calibration methods are well known to those skilled in the art and, therefore, will not be discussed in any great detail herein.

The transducer assemblies 108a and 108b of the described embodiment are advantageously positioned to provide a very low amount of inertia to the user handling object 18. Transducer assemblies 108a and 108b are decoupled, meaning that the transducers are both directly coupled to ground member 204 which is coupled to ground surface 186, i.e. the ground surface carries the weight of the dampers, not the user handling object 18. Similarly, sensors 110a and 110b are coupled to vertical members 206 which are coupled to ground surface 186. The weights and inertia of the dampers and sensors are thus substantially negligible to a user handling and moving object 18. This provides a more realistic interface to a virtual reality system, since the computer can control the dampers to provide substantially all of the damping resistances felt by the user in these degrees of motion. Interface system 202 is a high bandwidth force feedback system, meaning that high frequency signals can be used to control damper assemblies 108 and these high frequency signals will be applied to the user object with high precision, accuracy, and dependability. The user feels very little compliance or "mushiness" when handling object 18 due to the high bandwidth. In contrast, in typical prior art arrangements of multi-degree of freedom interfaces, one transducer "rides" upon another transducer in a serial chain of links and transducer. This low bandwidth arrangement causes the user to feel the inertia of coupled transducers when manipulating an object.

In addition, play mechanisms 114 as shown above in FIG. 6a can be added to the damper assemblies of FIGS. 9–10 to provide an desired amount of play.

User object 18 is a joystick handle 121 in the described embodiment of FIGS. 9 and 10 that a user can move in two degrees of freedom. The position of joystick 121 can be sensed and damping resistance can be applied in both degrees of freedom by computer system 16. In the described embodiment, joystick 121 is fastened to central member 210 so that the user can move the joystick in the two degrees of freedom provided by gimbal mechanism 182 as described above. In alternate embodiments, a linear axis F can be provided and a transducer can be coupled to the linear axis to provide a third and fourth degrees of freedom. In yet other embodiments, a floating gimbal mechanism, or a different mechanism, can be added to the joystick to provide six degrees of freedom.

Joystick 121 can be used in virtual reality simulations in which the user can move the joystick to move a computer-generated object in a simulation, move a simulated vehicle, point to objects on a screen, control a mechanism, etc. For example, a user can view a virtual environment generated on a computer screen or in 3D goggles in which joystick 121 controls an aircraft. The computer system tracks the position of the joystick as the user moves it around with sensors and updates the virtual reality display accordingly to make the aircraft move in the indicated direction, etc. The computer system also provides passive damping force feedback to the joystick, for example, when the aircraft is banking or accelerating in a turn or in other situations where the user A may experience resistances on the joystick and find it more difficult to steer the aircraft. In other simulations, joystick 121 can be provided with a pulsed (on and off) damping resistance to simulate a "bumpy" feel to the user grasping the joystick. This can simulate, for example, a vehicle moving over a bumpy road.

Figure 11:
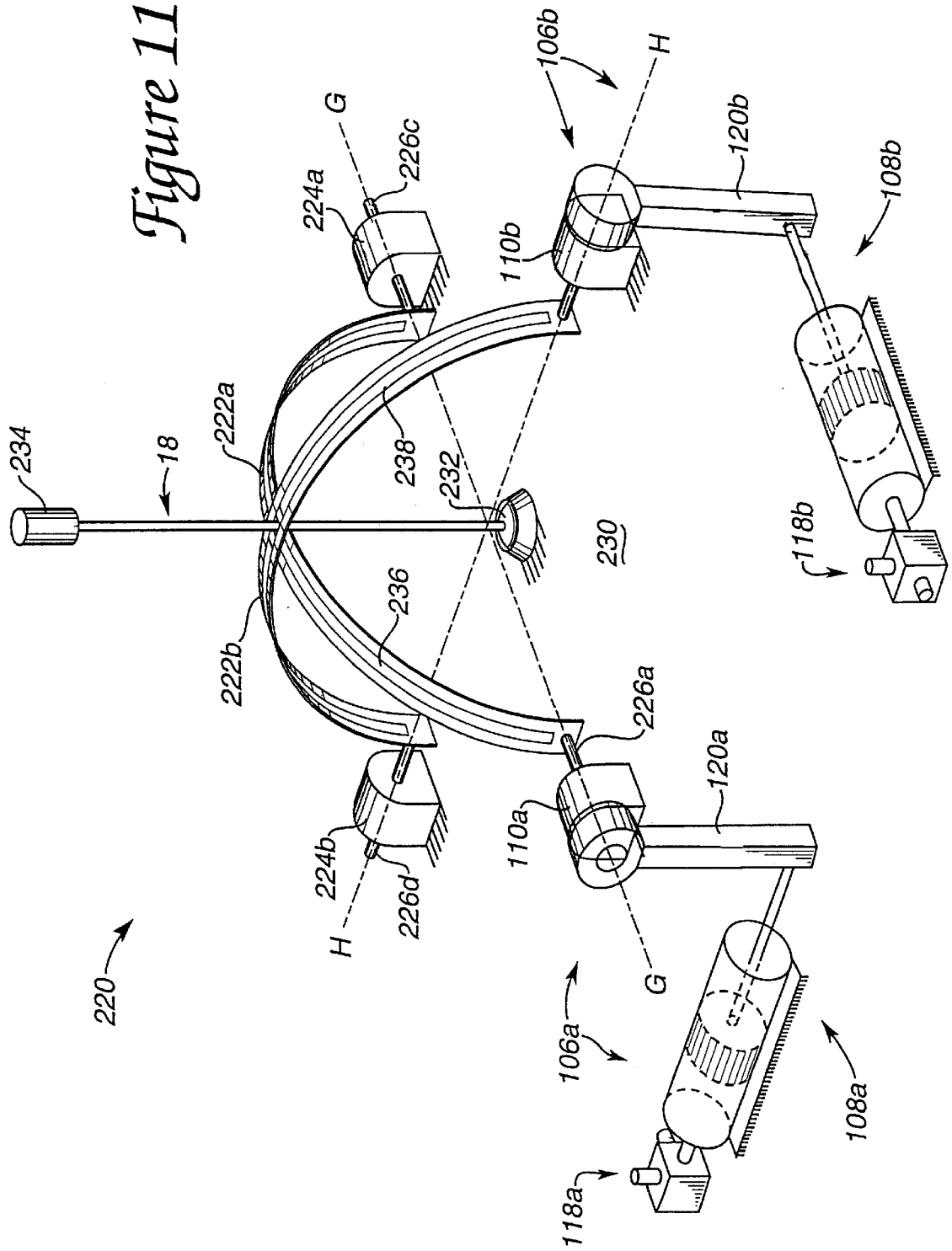

FIG. 11 is a perspective view of alternate interface system 220 suitable for use with transducer system 10 or 106. Interface system 220 includes a slotted yoke configuration for use with joystick controllers that is well-known to those skilled in the art. System 220 includes slotted yoke 222a, slotted yoke 222b, sensors 110a and 110b, bearings 224a, and 224b, damper assemblies 106a and 106b, and joystick 18. Slotted yoke 222a is rigidly coupled to shaft 226a that extends through and is rigidly coupled to sensor 110a at one end of the yoke. Slotted yoke 222a is similarly coupled to shaft 226c and bearing 224a at the other end of the yoke. Slotted yoke 222a is rotatable about axis L in a first degree of freedom and this movement is detected by sensor 110a. Sensors 110a and 110b and bearings 224a and 224b are grounded.

Damper assembly 108a is preferably a pneumatic damper as described above with reference to FIG. 6a. In alternate embodiments, damper assembly 108a can be instead coupled to shaft 226c next to bearing 224a. In yet other embodiments, sensor 110a can be coupled to shaft 226c or bearing 224a can be implemented as another sensor like sensor 110a.

Similarly, slotted yoke 222b is rigidly coupled to shaft 226b and sensor 110b at one end and shaft 226d and bearing 224b at the other end. Yoke 222b can rotated about axis H and this movement can be detected by sensor 110b. Damper assembly 108b is coupled to shaft 226b and is described in greater detail above with reference to FIG. 6a. Damper assemblies 108a and 108b are grounded as shown.

Alternatively, the linear damper assembly 10 of FIG. 1a can be used in place of the rotary actuator assemblies 106 shown in FIG. 11. In a different embodiment, the damper assemblies 108a and 108b can be coupled directly to object 18 as shown in FIG. 7.

Object 18 is a joystick that is pivotally attached to ground surface 230 at one end 232 so that the other end 234 typically can move in four 90-degree directions from its center position above surface 230 (and additional directions in other embodiments). Joystick 18 extends through slots 236 and 238 in yokes 222a and 222b, respectively. Thus, as joystick 18 is moved in any direction, yokes 222a and 222b follow the joystick and rotate about axes G and H. Sensors 110a–d detect this rotation and can thus track the motion of joystick 18. The addition of damper assemblies 108a and 108b allows the user to experience force feedback when handling joystick 18. Other types of objects 18 can also be used in place of a joystick, or additional objects can be coupled to joystick 18.

In alternate embodiments, dampers and couplings can be coupled to shafts 226c and 226d to provide additional force to joystick 112. Damper 108a and a damper coupled to shaft 226c can be controlled simultaneously by a computer or other electrical system to apply or release force from bail 222a. Similarly, damper assembly 108b and a damper coupled to shaft 226dcan be controlled simultaneously.

In a different embodiment, a play mechanism 114 as shown in FIG. 6a can also be rigidly coupled to shaft 226a and damper assembly 108a to provide a desired amount of play between damper assembly 108a and shaft 226a. Similarly, a coupling can be rigidly coupled to shaft 226b and damper 108b. Note that the slotted yoke configuration typically introduces some inherent play (such as compliance or backlash) to the mechanical system. Couplings can be added to provide an additional amount of play, if desired. Similarly, other interface mechanisms that typically provide an amount of inherent play can be used such that the inherent play is measured by sensor 110 and no play mechanism is required.

Figure 12:
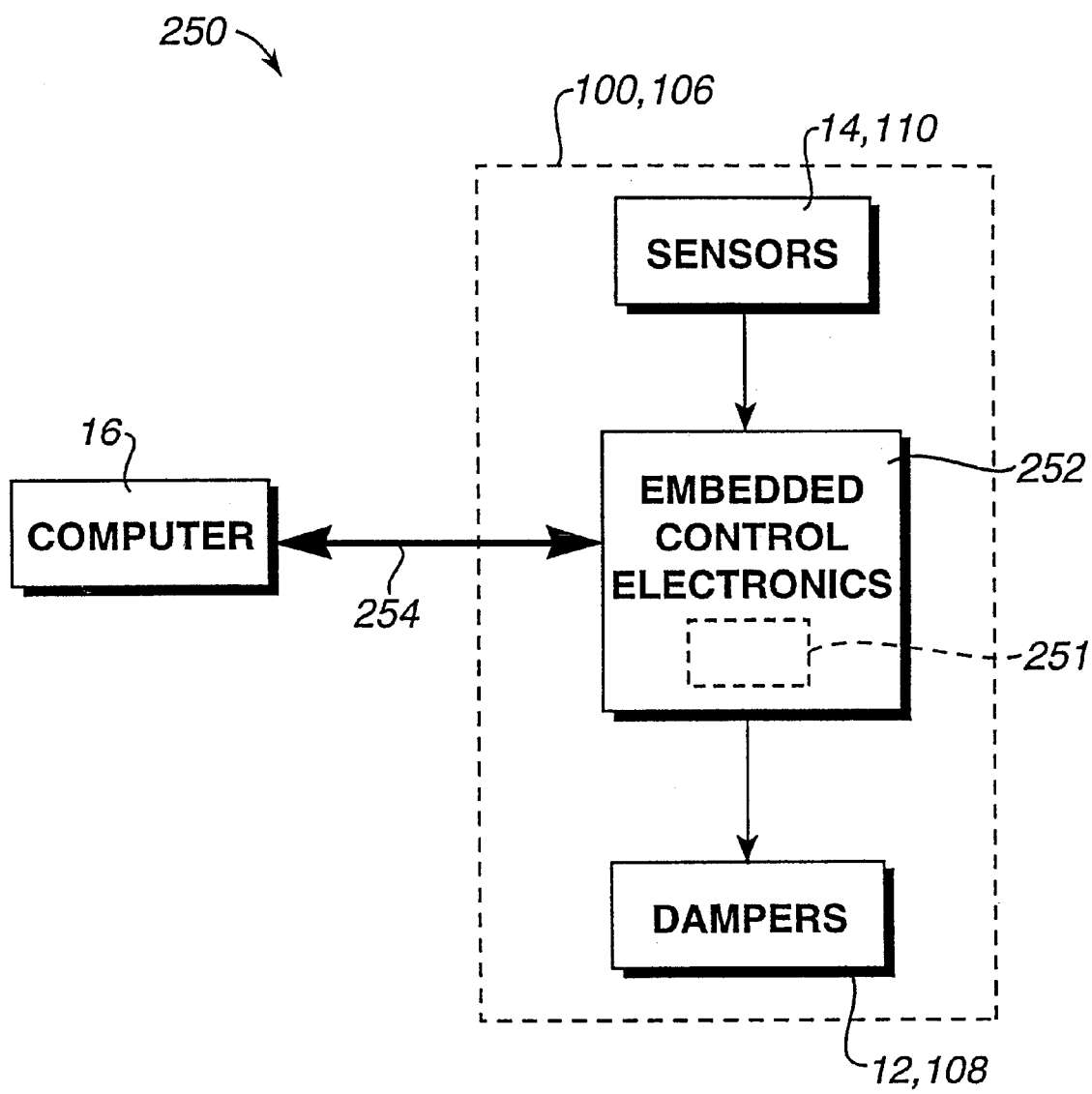
FIG. 12 is a block diagram of a control system for the interface systems of the present invention.

FIG. 12 is a block diagram illustrating a generic control system 250 for the interface apparatuses of the present invention. Control system 250 includes computer system 16, sensors 14 or 110, dampers 12 or 108, and control electronics 252. Computer system 16 sends signals to and receives signals from transducer systems included in an interface system. A bi-directional bus 254 is used to provide and receive these signals. In the preferred embodiment, a serial port of computer system 16, such as an RS232 port, connects the bi-directional bus to computer system 16. Alternatively, a parallel port of computer system 16 can be coupled to bus 254, or bus 254 can be connected directly to the data bus of computer system 16 using, for example, a plug-in card and slot or other access of computer system 16.

Computer system 16 can input a "sensor signal" on bus 254 from sensors 14 or 110 representing the position or motion of object 18. Computer system 16 can also output a "dampening signal" on bus 254 to dampers 12 or 108 to cause a damping resistance to user object 18. Sensors 14 or 110 and dampers 12 or 108 are described in the embodiments of FIGS. 1–11 and below in FIGS. 13 and 14. Control electronics 252 are positioned between computer system 16 and the sensors and dampers, and can include a variety of different components in different embodiments. For example, electronics 252 may just include bus wires connecting computer system 16 to the sensors and dampers. Or, electronics 252 may additionally include electronic components for communicating via standard protocols on bus 254. In addition, control electronics 252 can include signal conditioning/processing electronics for receiving signals from sensors 14 or 110 and/or power electronics for driving dampers 12 or 108.

Preferably, in the present invention, control electronics 252 includes a local embedded "control" microprocessor 251 to control sensors and dampers of the interface system independently of computer system 16. In such an embodiment, computer system 16 can issue high level supervisory commands to the local processor 251 over bus 254. The local processor 251 executes local control loops ("reflexes") for sensors and dampers in parallel with the high level control routines. Reflexes are useful when using a slower communication interface, such as a serial interface. For example, the local microprocessor 251 can be provided with instructions to wait for commands or requests from computer system 16, decode the commands or requests, and handle input and output signals according to the commands or requests. If computer system 16 sends a command to change the damping resistance provided by the dampers, the microprocessor can output signals to the damper representing the new damping force to be applied and can send an acknowledgment to computer system 16 that such output was sent. If computer system 16 sends a request for sensory input, the control microprocessor can send position data from the sensors to the computer 16. Processor 251 can also independently implement command routines to control dampers or sensors until a host command is received. Suitable microprocessors for use in such operations include the MC68HC711E9 by Motorola and the PIC16C74 by Microchip, for example.

Control electronics 252 can be provided as a component of the interface system, as shown in FIG. 12. Alternatively, the control electronics 252 can be included with computer system 16, such as on an interface card, peripheral, etc.

Figure 13:
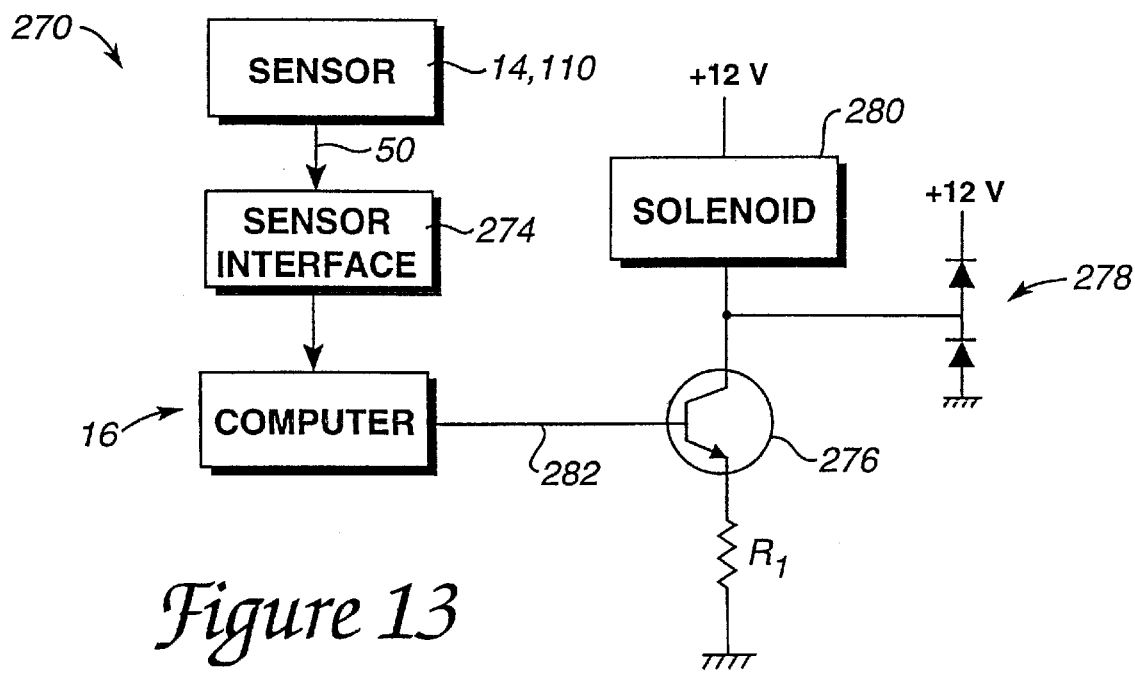
FIG. 13 is a schematic diagram of a first embodiment of the control system of FIG. 12.

FIG. 13 is a schematic illustration of a specific embodiment 270 of control system 250 as shown in FIG. 12. System 270 can send and receive signals to and from transducer system 10 or 106. System 270 is suitable for use with the dampers of the present invention which provide a passive fluid resistance to motion, and which include the two-state on/off valve as described with reference to FIG. 1a. System 270 includes digital sensor 14 or 110, sensor interface 274, transistor 276, voltage protector 278, and solenoid 280. Sensor interface 274, transistor 276, and voltage protector 278 can be considered part of the control electronics 252 of FIG. 12. A local processor 251 (not shown) can also be included in system 270 between computer system 16 and transistor 276/sensor interface 274.

Host computer system 16 receives sensor signals from one or more sensors 14 or 110 to determine the position of the object. The computer system preferably implements a simulation or similar virtual environment which a user is experiencing and moving object 18 in response to, as is well known to those skilled in the art. In the described embodiment, computer system 16 includes interface electronics, which preferably include a serial port, such as an RS-232 interface. This interface is suitable for controlling the passive dampers of the present invention.

Sensor 14 or 110 is preferably a digital sensor such as a relative optical encoder, as described above. Sensor 14 is preferably an electro-optical device that, for example, responds to a shaft's rotation by producing two phase-related signals (in a rotary degree of freedom); or produces these two signals in response to movement of a linear shaft (in a linear degree of freedom). In the described embodiment, a sensor interface 274 can be used to convert the sensor signals to signals that can be interpreted by the computer system. For example, sensor interface 274 receives the two phase-related signals from a sensor 14 or 110 and converts the two signals into another pair of clock signals, which drive a bi-directional binary counter. The output of the binary counter is received by computer system 16 as a binary number representing the angular position of the encoded shaft. Such circuits, or equivalent circuits, are well known to those skilled in the art; for example, the Quadrature Chip LS7166 from Hewlett Packard, California performs the functions described above. The position value signals are interpreted by computer system 16 which updates the virtual reality environment and controls damper 108 as appropriate. Other interface mechanisms can also be used to provide an appropriate signal to computer system 16. Sensor interface 274 can be included within computer system 16, such as on an interface board or card as used in typical personal computer systems. Alternatively, sensor interface 274 can be included within transducer system 10 or 106.

Alternatively, an analog sensor can be used instead of digital sensor 14 or 110 for all or some of the transducers of the present invention. For example, a strain gauge can be connected to measure forces. Analog sensors can provide an analog signal representative of the position of the user object in a particular degree of freedom. An analog to digital converter (ADC) can convert the analog signal to a digital signal that is received and interpreted by computer system 16, as is well known to those skilled in the art. The resolution of the detected motion of object 18 would then be limited by the resolution of the ADC. However, noise can sometimes mask small movements of object 18 from an analog sensor, which can potentially mask the play that is important to some embodiments of the present invention.

Transistor 276 is electrically coupled to computer system 16 at its base terminal and operates as an electrical switch for controlling the activation of solenoid 280. Solenoid 280 is coupled to the collector of transistor 276 and switches the valve 22 (as shown in FIG. 1) or 118 (as shown in FIG. 6a) between on and off states to control the damping resistance on the motion of object 18. Computer system 16 can send a dampening signal, such as a TTL logic signal, on bus 282 to control transistor 276 to either allow current to flow through the solenoid to activate it and open the valve, or to allow no current to flow to deactivate the solenoid and close the valve, as is well known to those skilled in the art. Resistor R1 is coupled between the emitter of transistor 276 and ground, and has a resistance adequate to cause the correct amount of current to flow through solenoid 280. Protection circuit 278 is coupled to the collector of transistor 276 and provides voltage spike protection to the circuitry and preferably includes two diodes or equivalent components.

Other type of interface circuitry can also be used. For example, an electronic interface is described in U.S. Pat. No. 5,576,727, issued Nov. 19, 1996 which is a continuation of U.S. patent application Ser. No. 08/092,974, filed Jul. 16, 1993 and entitled "3-D Mechanical Mouse" now abandoned assigned to the assignee of the present invention and incorporated herein by reference in their entirety. The electronic interface described therein was designed for the Immersion PROBE™ 3-D mechanical mouse and has six channels corresponding to the six degrees of freedom of the Immersion PROBE.

Figure 14:
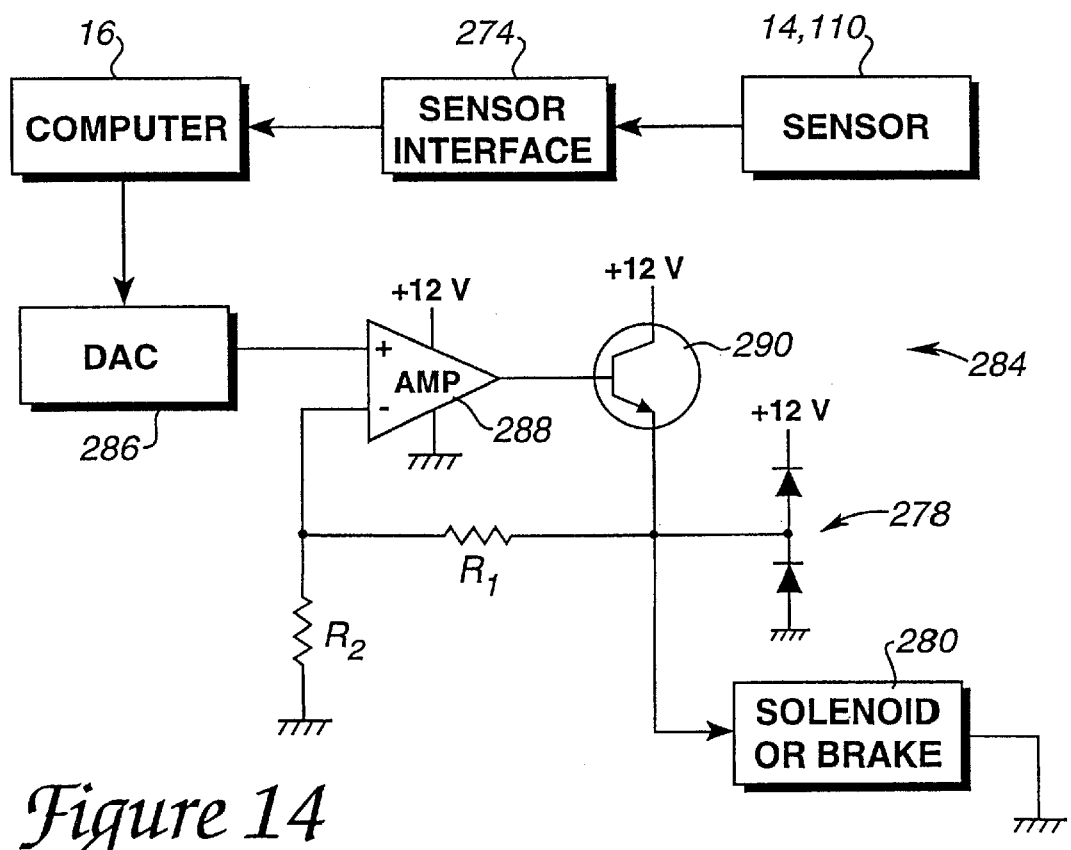
FIG. 14 is a schematic diagram of a second embodiment of the control system of FIG. 12.

FIG. 14 is a schematic illustration of circuitry 284 to send and receive signals from transducer system 10/106 and interface system 180. Circuitry 284 is suitable for use with passive dampers of the present invention which include a variable servo valve that is controlled with an analog voltage. Circuitry 284 can also be used to control other passive dampers or actuators, such as magnetic particle brakes and the like. Circuitry 284 includes computer system 16, digital sensor 14 or 110, sensor interface 274, digital to analog converter (DAC) 286, amplifier 288, transistor 290, voltage protector 278, and solenoid 280. All these components except the computer system 16 and sensors 14 or 110 can be considered as part of control electronics 252.

Sensor interface 274 receives a signal from sensor 14 or 110 and is coupled to computer system 16. These components are substantially similar to the equivalent components described with reference to FIG. 13. DAC 286 is coupled to computer system 16 and receives a digital signal from the computer system representing a resistive force value to be applied to user object 18. DAC 286 converts the digital signal voltages to analog voltages which are then output to amplifier 288. A DAC suitable for use with the present invention is described with reference to FIG. 15. Amplifier 288 receives the analog voltage from DAC 286 on a positive terminal and scales the voltage signal to a range usable by solenoid 280. Amplifier 288 can be implemented as an operational amplifier or the like. Transistor 290 is coupled to the output of amplifier 288 and preferably operates as an amplifier to provide increased output current to solenoid 280. Resistor R1 is coupled between the negative terminal of amplifier 288 and the emitter of transistor 290, and resistor R2 is coupled between the negative terminal of amplifier 288 and ground. For example, resistors R1 and R2 can have values of 180 k$\Omega$ and 120 k$\Omega$, respectively, and provide the proper biasing in the circuit. Voltage protector 278 is coupled to the emitter of transistor 290 and provides protection from voltage spikes when using inductive loads, similar to protector 278 of FIG. 13. Solenoid 280 is coupled to the emitter of transistor 290 and to ground, and can be a standard solenoid for use in valves 22. Alternatively, a different passive damper, such as a magnetic particle brake, can be coupled to circuitry 284 in place of solenoid 280. A separate DAC and amplifier can be used for each solenoid or other actuator/damper implemented in the interface apparatus so the computer system 16 can control each damper separately for each provided degree of motion. Circuitry 284 (and 270 of FIG. 13) is intended as one example of many possible circuits that can be used to interface a computer system to sensors and dampers.

The computer system 16 shown in FIGS. 13 and 14 sends and receives signals preferably from a serial port, such as an RS-232 serial interface. An advantage of the present invention is that slower serial communication signals can be used to control the described passive damper, thus allowing a computer's built-in serial interface to be used directly. Alternatively, circuitry 284 can be provided on an interface card which can, for example, fit into an interface slot of computer system 16. For example, if computer 16 is an IBM AT compatible computer, the interface card can be implemented as an ISA, EISA, VESA local bus, or other well-known standard interface card which plugs into the motherboard of the computer and provides input and output ports connected to the main data bus of the computer.

Figure 15:
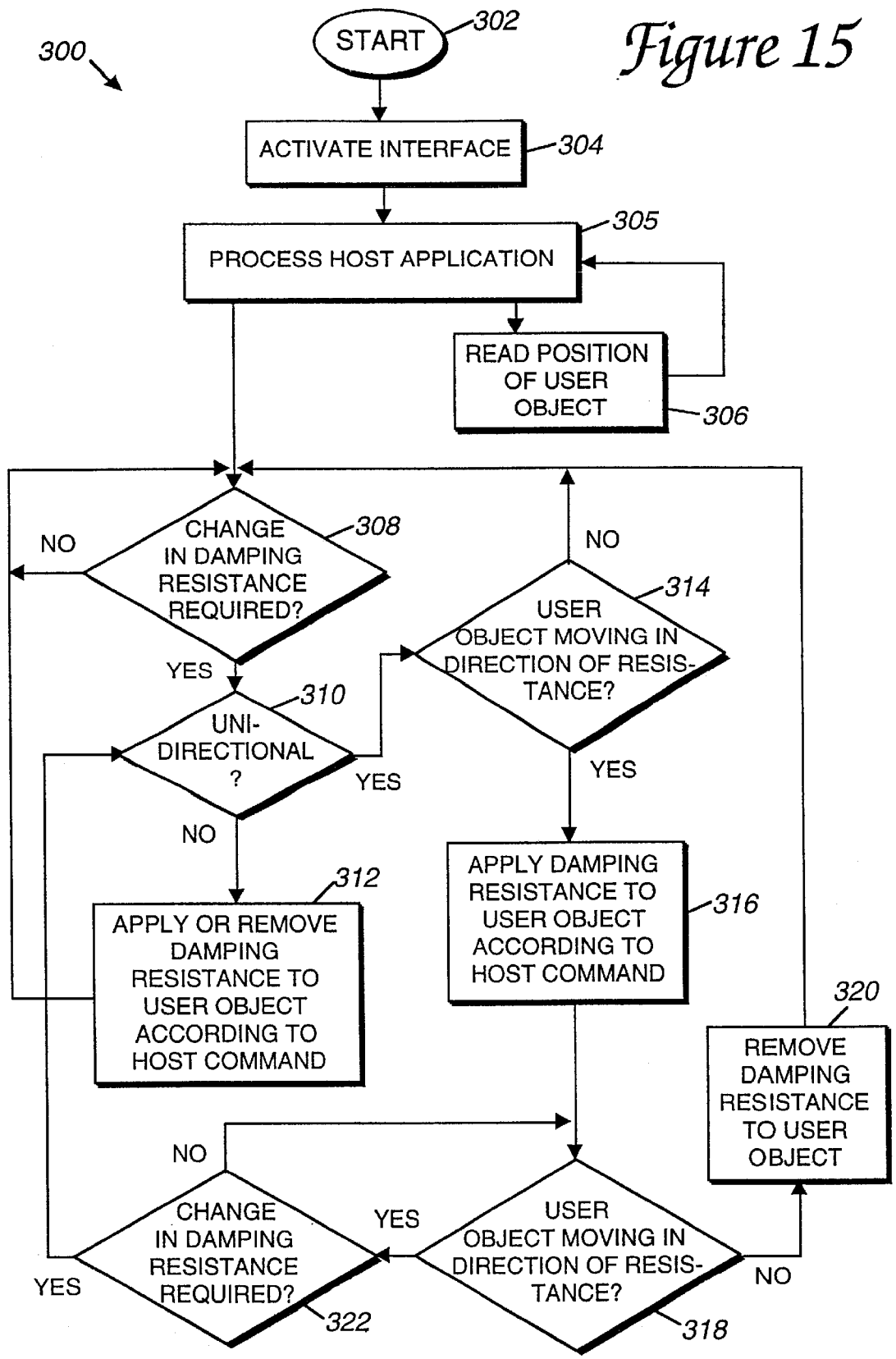
FIG. 15 is a flow diagram illustrating a method for controlling the transducer systems of the present invention.

FIG. 15 is a flow diagram illustrating a control process 300 for an interface system 100 or 106 of the present invention. This process can be used generically to provide force feedback to a user of the interface. In the preferred embodiment, a local processor is included in control electronics 252 as described above. The steps of process 300 can be implemented from host computer 16 or a local processor.

The process begins at 302, and in a step 304, the interface system is activated. This step is the equivalent of powering up the interface so that it can be commanded by host computer 16 and/or processor 251. In step 305, a process on computer system 16, such as a simulation, video game, etc., is begun or continued. In the process of step 305, images can be displayed for a user on an output display device and other feedback can be presented.

Two branches exit step 305 to indicate that there are two processes running simultaneously, i.e. in parallel. Step 306 is implemented in one of the parallel processes, in which the position of the user object is read in by the host computer. Preferably, the local processor continually receives commands from the host computer 16 to read signals from sensors 14 or 110 and to send those signals to the host computer 16. After the sensors are read in step 306, the host computer can update a game or virtual reality environment in response to the user's movements of object 18 in step 305. For example, if the user moves a steering wheel object 18, the computer system 16 can move the point of view of the user as if looking out a vehicle and turning the vehicle. Steps 305 and 306 are repeated continuously and in parallel with other interface processes so that the host computer receives the most recent position or change in position of object 18.

The second branch from step 304 is concerned with the process of controlling the dampers of the present invention to provide force feedback to the user manipulating object 18. The second branch starts with step 308, in which the host computer (and/or local microprocessor 251) check if a change in damping resistance is required to be applied to user object 18. This can be determined by several types of criteria. For example, if the host computer is implementing a video game, the position of a computer generated object within the game may determine if a change in force feedback (damping resistance) is called for. If the user is controlling a space ship in the game and the space ship collides with an object such as an asteroid, then damping resistance should be applied to the user object 18. In many cases, the current position of the user object, as detected in step 306, determines whether a change in damping resistance is required. In addition, other parameters in the game, simulation, or other process implemented by the computer system 16 can determine if a change in damping resistance to the user object is necessary. For example, the computer system 16 may randomly determine that the user's space ship is impacted with an object due to "environmental" conditions which are not dependent on the position of the user object, such as a meteor storm, in which a greater damping resistance should be applied to simulate the impact.

If no change in damping resistance is currently required, then the process continuously returns to step 308 until such a change in damping resistance is required, When such a change is required, step 310 is implemented, in which computer system 16/local processor checks if the new damping resistance is to be uni-directional or bi-directional. Uni-directional damping resistance is applied in only one specified direction along a degree of freedom. Thus, the user would feel resistance to the motion of the user object 18 is one direction, such as clockwise or left, but would be able to freely move the object (or move the object with a different degree of resistance) in the opposite direction of that degree of freedom (or dimension), such as counterclockwise or right. Bi-directional damping resistance is applied to both directions along a degree of freedom so that the user would feel the same magnitude of resistance in either direction. Uni- and bi-directional resistances can be determined by the game or other process implemented by computer system 16. For example, if a user's simulated race car collides into a wall, then uni-directional damping resistance should be applied only in the direction of the wall, since the user would be able to freely move in the reverse direction to the wall. However, if the simulated car is stuck in a simulated pool of mud, then bi-directional resistance should be applied, since the car will feel the same resistance to motion in any direction.

If the required damping resistance is unidirectional, step 314 is implemented as described below. If the required damping resistance is bi-directional, then step 312 is implemented, in which the desired amount of damping resistance is applied or removed to the user object as specified by a command from the host computer. Preferably, the host computer sends a command to the local microprocessor 251 indicating the magnitude of damping resistance and the degree of freedom that the resistance is to be applied (such as "horizontal" or "vertical"). If a single on-off valve is being used in the desired degree of freedom, then the magnitude of resistance can be specified as an "on" signal (maximum resistance applied) or an "off" signal (no resistance applied). If variable resistance can be applied, then a number from the host computer can indicate the magnitude of damping resistance. The local processor, in turn, implements the command by sending an appropriate signal to the appropriate damper.

After the resistance has been applied, the process returns to step 308 to determine if there is a change in the applied damping resistance. Preferably, the host computer system 16 only sends a command to change the magnitude of the resistance. Thus, if no change in damping resistance is required at step 308, the local processor will continue to command the dampers to apply the magnitude of resistance that was last provided to the local processor. Once a change in damping resistance is required, then the process again implements step 310.

If the required damping resistance in step 310 is not bi-directional, then it is uni-directional. Preferably, the host computer system sends a command to the local processor indicating the magnitude of the damping resistance to be applied and the specific direction in a degree of freedom in which the resistance is to be applied. For example, if a joystick has two degrees of freedom of "horizontal" and "vertical", then the direction can be specified as "horizontal-left", "horizontal-right", "vertical-left" or "vertical-right." Step 314 is then implemented, in which the host computer/ local processor checks whether the user object is moving in the designated direction of resistance. Since the preferred dampers of the present invention provide resistance bi-directionally, as described in the embodiments above, a desired amount of "play" may be implemented to detect movement in the direction opposite to the direction of resistance, as explained above with reference to FIGS. 6a–6e. Preferably, the local processor implements step 314 autonomously as a "reflex" to remove processing burdens from the host computer, remove communication lag from the computer system 16 to the user object, and improve system performance. Such a reflex is most appropriate when using a serial interface to communicate with the host computer.

If the user is not moving in the direction of resistance, then the user object can be moved freely and the process returns to step 308 to check if a change in the applied damping resistance (or lack in applied resistance) is required. If the user is moving in the direction of resistance in step 314, then step 316 is implemented, in which the specified magnitude of damping resistance is applied to the user object. As explained above, the preferred dampers of the present invention always apply bi-directional resistance to the user object. Thus, to simulate uni-directional resistance, the computer or processor should be able to detect movement opposite to the direction of resistance. This is the reason for the inclusion of the play mechanism described with reference to FIGS. 6a–6e.

After step 316, step 318 is implemented, in which the host computer/local processor again checks if the user object is being moved in the designated direction of resistance. If not, then local processor (or host computer) removes the applied damping resistance in step 320. The process then returns to step 308 to check if a change in damping resistance is required. If the user object is being moved in the direction of resistance in step 318, then step 322 is implemented, in which the local processor (or host computer) checks if a change in damping resistance is required. This can occur if the computer process of step 305 requires a different resistance to be applied, etc., as described above with reference to step 308; the host computer can issue a command to processor 251 to change the applied damping resistance (or remove the applied resistance; a removal command can be considered a bi-directional resistance command). If change in resistance is not required, then the process returns to step 318 to again check the direction of the user object. If a change in resistance is required, the process returns to step 310 to determine if the required resistance is bi-direction or unidirectional, as described above.

A Steps 314–322 are preferably implemented as a "reflex" executed autonomously by the local processor 251. The local processor can independently check the direction of the movement of the user object and apply a uni-directional resistance when appropriate, thus freeing the host computer to run the application process of step 305. When a different resistance is to be applied, or a resistance removed, the host computer can issue a command to do so at the appropriate time.

The above-described process can be used to provide a variety of haptic sensations to the user through the user object 18 to simulate many different types of tactile events. Three typical haptic sensations include a virtual obstruction, a virtual texture, and virtual damping.

Virtual obstructions are provided to simulate walls and other uni-directional forces in a simulation, game, etc. For example, the movement of a cursor displayed on a display screen can be controlled by a force feedback joystick. An obstruction, like a brick wall, can also be displayed on the screen. The user moves the cursor left until the cursor encounters the obstruction. The user then feels a physical resistance as he or she continues to move the joystick left, since the local processor (receiving a command from the computer system 16) has applied maximum unidirectional resistance in the direction of the obstruction in step 320 of FIG. 16 above. If the user moves the cursor away from the obstruction (right), the processor removes the resistance in step 318 of FIG. 16. Thus the user is given a convincing sensation that the virtual obstruction displayed on the screen has physical properties.

Virtual textures can be used to simulate a surface condition or similar texture. For example, as the user moves a joystick or other user object along an axis, the host computer sends a rapid sequence of commands informing the local processor to repetitively 1) apply bi-directional resistance along that axis, and 2) to then immediately apply no resistance along that axis. This causes an on-off valve, for example, to open and close at a desired frequency. This frequency is based upon the travel of the joystick handle and is thus correlated with spatial position. Thus, the user feels a physical sensation of texture, which can be described as the feeling of dragging a stick over a grating.

Virtual damping can be used to simulate motion through a viscous fluid, wind, or a similar resistive or "damping" environment. For example, a cursor controlled by a joystick is moved through a region that simulates a thick liquid, such as syrup. The host computer 16 commands that a bi-directional horizontal and vertical resistance be applied to the joystick when the cursor enters the region. The user feels the physical resistance as the cursor moves through the region. The resistance is immediately removed when the cursor exits the region. Thus the user is given a convincing sensation that the region displayed on the screen has physical properties.

While this invention has been described in terms of several preferred embodiments, it is contemplated that alterations, modifications and permutations thereof will become apparent to those skilled in the art upon a reading of the specification and study of the drawings. For example, the linked members of gimbal apparatus 182 can take a number of actual physical sizes and forms while maintaining the disclosed linkage structure. In addition, other gimbal mechanisms can also be provided with a linear axis member 184 to provide three degrees of freedom. A variety of devices can also be used to sense the position of an object in the provided degrees of freedom. Other pneumatic (or hydraulic) devices can also be used to provide a passive resistance to a user object in accordance with the present invention. Furthermore, certain terminology has been used for the purposes of descriptive clarity, and not to limit the present invention. It is therefore intended that the following appended claims include all such alterations, modifications and permutations as fall within the true spirit and scope of the present invention.

What is claimed is:

1. A force feedback interface device for use with a host computer displaying a graphical environment, said force feedback interface device providing force feedback sensations to a user, said interface device comprising:

a user manipulatable object contacted by a user and moveable in two linear degrees of freedom, said two linear degrees of freedom substantially defining a plane, said user manipulatable object including a recess for contacting a tip portion of at least one finger of said user or a tip portion of a stylus;

at least one sensor in communication with said host computer and coupled to said user manipulatable object for sensing positions of said user manipulatable object along at least one of said degrees of freedom; and a first and a second actuator, each in communication with said host computer, said first actuator comprising a first linear member mechanically coupled to said user manipulatable object to apply a force to said object along a first linear degree of freedom, and said second actuator comprising a second linear member mechanically coupled to said user manipulatable object to apply a force to said object along a second linear degree of freedom, wherein said first linear member is a flexible member that flexes when said user manipulatable object is moved in said second degree of freedom, and wherein said second linear member is a flexible member that flexes when said user manipulatable object is moved in said first degree of freedom.

2. A force feedback interface device as recited in claim 1 wherein said recess comprises a finger-receiving portion including a divot for holding said tip portion of said at least one finger of said user.

3. A force feedback interface device as recited in claim 1 wherein said recess is for contacting a tip portion of at least one finger of said user, and wherein said recess includes a surface that is substantially planar on which said tip portion of said at least one finger rests and wherein said surface includes a means for preventing said tip portion of said finger from slipping on said surface.

4. A force feedback interface device as recited in claim 3 wherein said means for preventing said tip portion of said finger from slipping on said surface includes at least one bump.

5. A force feedback interface device as recited in claim 4 wherein said means for preventing said tip portion of said finger from slipping on said surface includes a plurality of bumps and wherein said recess receives a plurality of fingers of said user.

6. A force feedback interface device as recited in claim 1 wherein said actuators provide said force as a resistance to motion by changing the flow rate of a fluid.

7. A force feedback interface device as recited in claim 6 wherein said fluid is an electrorheological fluid having a viscosity changed by applying an electric field to said fluid.

8. A force feedback interface device as recited in claim 7 further comprising a local microprocessor separate from said host computer and coupled between said actuators and said host computer, said microprocessor controlling said electric field with at least one electrode and controlling said resistance on said user manipulatable object based on commands received from said host computer.

9. A force feedback interface device as recited in claim 1 further comprising a local microprocessor separate from said host computer and coupled between said actuators and said host computer, said microprocessor controlling said force output by said actuators.

10. A force feedback interface device as recited in claim 1 wherein said first and second linear members are substantially in said plane.

11. A force feedback interface device as recited in claim 1 wherein said first and second linear members are substantially perpendicular.

12. An interface device for use with a host computer updating a graphical environment in response to user manipulation of said interface device, said host computer commanding said computer interface device to generate force feedback sensations in coordination with events within said graphical environment, said interface device comprising:

a user object contacted by a user;

a support mechanism which supports said user object while allowing a degree of freedom of motion of said object with respect to a grounding surface;

an actuator for providing resistance to motion of said user object along said degree of freedom of said user object, said actuator including a grounded portion and a non-grounded portion, wherein said grounded portion of said actuator remains stationary with respect to said grounding surface, and wherein said resistance to motion is varied by said actuator in response to commands from said host computer;

a slotted yoke mechanism provided between said actuator and said user object, said slotted yoke mechanism allowing an inherent amount of play between said user object and said non-grounded portion of said actuator; and a sensor system, said sensor system being grounded wherein a portion of said sensor system remains stationary with respect to said grounding surface, and wherein a different portion of said sensor system is coupled to said user object and moves with respect to said grounding surface when said user object moves along said degree of freedom, wherein no substantial play is allowed between said user object and said portion of said grounded sensor system coupled to said user object, said motion of said coupled sensor portion resulting in signals representing a position of said user object along said degree of freedom, and wherein said inherent amount of play is detectable within a sensing resolution of said sensor system.

13. An interface device as recited in claim 12 wherein said user object is moveable in a plurality of degrees of freedom, and wherein said slotted yoke mechanism includes a plurality of slotted yokes, each yoke provided for an associated degree of freedom, and wherein said user object includes a portion extending through a slot of each of said yokes.

14. An interface device as recited in claim 12 wherein one of said portions of said sensor system includes an emitter of electromagnetic energy and another of said portions of said sensor system includes a detector of said electromagnetic energy.

15. An interface device as recited in claim 12 further comprising a local microprocessor separate from said host computer, said local microprocessor electrically coupled to said actuator and to said sensor system such that said local microprocessor is operative to control said actuator and read said sensor, said local microprocessor coupled to said host computer by a communication interface and executing a local process in parallel with host execution of said graphical simulation.

16. An interface device as recited in claim 15 wherein said local microprocessor reads said sensor system locally to detect free motion of said user object within a play region defined by said play and adjust resistance applied by said actuator based on said motion in said play region.

17. An interface device as recited in claim 12 wherein said actuator includes a fluid that changes its viscous properties in response to an electromagnetic field.

18. A force feedback interface device for use with a host computer displaying a graphical environment, said force feedback interface device providing force feedback sensations to a user, said interface device comprising:

a user manipulatable object contacted by a user and moveable in two linear degrees of freedom, said two linear degrees of freedom substantially defining a plane, said user manipulatable object including a recess for contacting a tip portion of at least one finger of said user or a tip portion of a stylus;

at least one sensor in communication with said host computer and coupled to said user manipulatable object for sensing positions of said user manipulatable object along at least one of said degrees of freedom; and a first and a second actuator, each in communication with said host computer, said first actuator comprising a first linear member mechanically coupled to said user manipulatable object to apply a force to said object along a first linear degree of freedom, and said second actuator comprising a second linear member mechanically coupled to said user manipulatable object to apply a force to said object along a second linear degree of freedom, wherein said actuators provide said forces as a resistance to motion by changing the flow rate of an electrorheological fluid having a viscosity changed by applying an electric field to said fluid.

* * * * *